(12) United States Patent
Chambers et al.

(10) Patent No.: US 12,084,509 B2
(45) Date of Patent: Sep. 10, 2024

(54) GENE SIGNATURES FOR MONITORING ACUTE REJECTION AND METHODS OF USING SAME

(71) Applicant: Duke University, Durham, NC (US)

(72) Inventors: Eileen Chambers, Durham, NC (US); Qing Cheng, Durham, NC (US); Allan Kirk, Durham, NC (US)

(73) Assignee: Duke University, Durham, NC (US)

( * ) Notice: Subject to any disclaimer, the term of this patent is extended or adjusted under 35 U.S.C. 154(b) by 42 days.

(21) Appl. No.: 17/245,794

(22) Filed: Apr. 30, 2021

(65) Prior Publication Data

US 2021/0340269 A1 Nov. 4, 2021

Related U.S. Application Data

(60) Provisional application No. 63/017,695, filed on Apr. 30, 2020.

(51) Int. Cl.

| | | |
|---|---|---|
| *C07K 16/28* | (2006.01) | |
| *A61K 31/573* | (2006.01) | |
| *A61K 45/06* | (2006.01) | |
| *C12Q 1/6876* | (2018.01) | |

(52) U.S. Cl.
CPC ........ *C07K 16/2887* (2013.01); *A61K 31/573* (2013.01); *A61K 45/06* (2013.01); *C07K 16/2809* (2013.01); *C07K 16/2893* (2013.01); *C12Q 1/6876* (2013.01)

(58) Field of Classification Search
CPC ............ C07K 16/2887; C07K 16/2809; C07K 16/2893; C07K 2319/30; C07K 16/2866; A61K 31/573; A61K 45/06; A61K 2039/505; A61K 39/39541; A61K 31/436; A61K 31/52; A61K 31/5377; A61K 2300/00; C12Q 1/6876; C12Q 1/6883; C12Q 2600/106; G01N 33/6893; G01N 2800/245; A61P 13/12
See application file for complete search history.

(56) References Cited

U.S. PATENT DOCUMENTS

| | | | |
|---|---|---|---|
| 3,710,795 | A | 1/1973 | Higuchi et al. |
| 4,863,457 | A | 9/1989 | Lee |
| 5,501,856 | A | 3/1996 | Ohtori et al. |
| 2008/0241223 | A1 | 10/2008 | Nivaggioli et al. |
| 2017/0191128 | A1 | 7/2017 | Salomon et al. |

FOREIGN PATENT DOCUMENTS

| | | |
|---|---|---|
| EP | 0430539 | 6/1991 |
| EP | 0488401 | 6/1992 |

OTHER PUBLICATIONS

Flechner et al., Kidney Transplant Rejection and Tissue Injury by Gene Profiling of Biopsies and Peripheral Blood Lymphocytes, 2004.*
Shihab et al., Transforming Growth Factor-Beta and Matrix Protein Expression in Acute and Chronic Rejection of Human Renal Allografts, 1995.*
Lymphocyte-depleting induction therapy lowers the risk of acute rejection in African American pediatric kidney transplant recipients, 2016.*
Sabek et al. Transplantation 74(5):701-707 (2002) (Year: 2002).*
Affymetrix GeneChip Human Genome U95 Set (2002) (Year: 2002).*
HG_U95B Affymetrix Human Genome U95B Array (2002) (Year: 2002).*
The GeneChip System Affymetrix (2001) (Year: 2001).*
Altschul et al., "Basic Local Alignment Search Tool", Journal of Molecular Biology, vol. 215, No. 3, Oct. 5, 1990, pp. 403-410.
Altschul et al., "Gapped BLAST and PSI-BLAST: A New Generation of Protein Database Search Programs", Nucleic Acids Research, vol. 25, No. 17, Sep. 1, 1997, pp. 3389-3402.
Berglund et al., "Characteristics and Validation Techniques for PCA-Based Gene-Expression Signatures", International Journal of Genomics, vol. 2017, Feb. 6, 2017, 13 pages.
Cooper, "Evaluation and Treatment of Acute Rejection in Kidney Allografts", Clinical Journal of the American Society of Nephrology : CJASN, vol. 15, No. 3, Mar. 2020, pp. 430-438.
Gibson et al., "A Novel Method for Real Time Quantitative RT-PCR", Genome Research, vol. 6, No. 10, Oct. 1996, pp. 995-1001.
Halloran, "Immunosuppressive Drugs for Kidney Transplantation", The New England Journal of Medicine, vol. 351, No. 26, Dec. 23, 2004, pp. 2715-2729.
Hames et al., "Nucleic Acid Hybridization: A Practical Approach", IRL Press Limited, 1985, 16 pages.
Held et al., "Real Time Quantitative PCR", Genome Research, vol. 6, No. 10, Oct. 1996, pp. 986-994.
Karlin et al., "Applications and Statistics for Multiple High-Scoring Segments in Molecular Sequences", Proceedings of the National Academy of Sciences USA, vol. 90, No. 12, Jun. 15, 1993, pp. 5873-5877.
Shaw et al., "An Age-Independent Gene Signature for Monitoring Acute Rejection in Kidney Transplantation", Theranostics, vol. 10, No. 15, May 25, 2020, pp. 6977-6986.
4 Facts You Need to Know About Kidney Transplants and Dialysis, Health Essentials from Cleveland Clinic, Available Online at: web.archive.org/web/20201001131150/https://health.clevelandclinic.org/4-facts-you-need-to-know-about-kidney-transplants-and-dialysis/, Jul. 28, 2014, 2 pages.
Natera Develops Powerful Kidney Transplant Rejection Biomarker, Natera, Available Online at: www.natera.com/company/news/natera-develops-powerful-kidney-transplant-rejection-biomarker-2/, Jun. 21, 2018, 4 pages.
Alelign et al., Kidney Transplantation: The Challenge of Human Leukocyte Antigen and Its Therapeutic Strategies, Journal of Immunology Research, vol. 2018, Article ID 5986740, Mar. 5, 2018, 18 pages, doi: 10.1155/2018/5986740.

(Continued)

*Primary Examiner* — Jessica H Roark
*Assistant Examiner* — Francesca Edgingtongiordan
(74) *Attorney, Agent, or Firm* — Kilpatrick Townsend & Stockton LLP

(57) ABSTRACT

The present disclosure provides methods and compositions for detecting and treating acute transplant rejection.

14 Claims, 10 Drawing Sheets

Specification includes a Sequence Listing.

(56) References Cited

OTHER PUBLICATIONS

Azad et al., Inflammatory Macrophage-associated 3-Gene Signature Predicts Subclinical Allograft Injury and Graft Survival, JCI Insight, vol. 3, No. 2, Article e95659, Jan. 25, 2018, 12 pages, doi: 10.1172/jci.insight.95659.

Bajpai et al., Interventions for Treating Antibody-mediated Acute Rejection in Kidney Transplant Recipients, Cochrane Database of Systematic Reviews, Issue 5, Article No. CD013033, May 19, 2018, 12 pages, , DOI: 10.1002/14651858.CD013033.

Eikmans et al., Non-Invasive Biomarkers of Acute Rejection in Kidney Transplantation: Novel Targets and Strategies, Frontiers in Medicine (Lausanne), vol. 5, Article 358, Jan. 8, 2019, pp. 1-7, doi: 10.3389/fmed.2018.00358.

Kim et al., Gene Expression Profiles for Predicting Antibody-Mediated Kidney Allograft Rejection: Analysis of GEO Datasets, International Journal of Molecular Medicine, vol. 42, No. 4, Jul. 31, 2018, pp. 2303-2311, doi: 10.3892/ijmm.2018.3798.

Maier, Blood Test Predicts Signs of Acute Rejection in Kidney Transplants, Finding Could Lead to Earlier Detection, Treatment and Organ Survival, UC San Francisco Press Release, Available Online at www.ucsf.edu/news/2014/U.S. Appl. No. 11/120,761/blood-test-predicts-signs-acute-rejection-kidney-transplants, Nov. 11, 2014, 6 pages.

Maluf et al., Molecular Pathways Involved in Loss of Kidney Graft Function with Tubular Atrophy and Interstitial Fibrosis, Molecular Medicine, vol. 14, Nos. 5-6, May-Jun. 2008, Published online Feb. 7, 2008, pp. 276-285, doi: 10.2119/2007-00111.Maluf.

Menon et al., Moving Biomarkers toward Clinical Implementation in Kidney Transplantation, Journal of the American Society of Nephrology, vol. 28, No. 3, Mar. 2017, pp. 735-747, doi: 10.1681/ASN.2016080858.

Roedder et al., The kSORT Assay to Detect Renal Transplant Patients at High Risk for Acute Rejection: Results of the Multicenter AART Study, PLOS Medicine, vol. 11, No. 11, Article No. e1001759, Nov. 11, 2014, 15 pages, doi: 10.1371/journal.pmed. 1001759.

Sanders et al., Drugs in Development for Prophylaxis of Rejection in Kidney-Transplant Recipients, Transplant Research and Risk Management, Dovepress, vol. 2015, No. 7, Aug. 18, 2015, pp. 59-69, doi: 10.2147/TRRM.S61446.

Sindhi et al., Profile of the Pleximmune blood test for transplant rejection risk prediction, Expert Rev Mol Diagn., 16(4), 2016, pp. 387-393, doi: 10.1586/14737159.2016.1139455.

Tushla, When a Transplant Fails, National Kidney Foundation, Available Online at: www.kidney.org/transplantation/transaction/TC/summer09/TCsm09_TransplantFail, Accessed from Internet on Jul. 19, 2023, 2 pages.

The Gene Ontology Resource: 20 years and still Going strong, Nucleic Acids Research, vol. 47, Nov. 5, 2018, pp. D330-D338.

Ali et al., Post Renal Biopsy Complication Rate and Diagnostic Yield Comparing Hands Free (Ultrasound-assisted) and Ultrasound-guided Biopsy Techniques of Renal Allografts and Native Kidney, Springerplus, vol. 4, No. 1, Sep. 12, 2015, pp. 1-6.

Ashburner et al., Gene Ontology: Tool for the Unification of Biology. The Gene Ontology Consortium, Nature Genetics, vol. 25, No. 1, May 2000, pp. 1-9.

Edgar et al., Gene Expression Omnibus: NCBI Gene Expression and Hybridization Array Data Repository, Nucleic Acids Research, vol. 30, No. 1, Jan. 1, 2002, pp. 207-210.

Einecke et al., A Molecular Classifier for Predicting Future Graft Loss in Late Kidney Transplant Biopsies, The Journal of Clinical Investigation, vol. 120, No. 6, Jun. 2010, pp. 1862-1872.

El Ters et al., Kidney Allograft Survival After Acute Rejection, the Value of Follow-Up Biopsies, American Journal of Transplantation, vol. 13, No. 9, Sep. 2013, pp. 2334-2341.

Fan et al., USP4 targets TAK1 to downregulate TNFa-induced NF-КВ activation, Cell Death and Differentiation, vol. 18, Oct. 2011, pp. 1547-1560.

Flechner et al., Kidney Transplant Rejection and Tissue Injury by Gene Profiling of Biopsies and Peripheral Blood Lymphocytes, American Journal of Transplantation, vol. 4, No. 9, Sep. 2004, pp. 1-24.

Graziotto et al., Perforin, Granzyme B, and Fas Ligand for Molecular Diagnosis of Acute Renal-Allograft Rejection: Analyses on Serial Biopsies Suggest Methodological Issues, Transplantation, vol. 81, Apr. 27, 2006, pp. 1125-1132.

Grigoryev et al., Deconvoluting Post-transplant Immunity: Cell Subset-specific Mapping Reveals Pathways for Activation and Expansion of Memory T, Monocytes and B Cells, PLOS One, vol. 5, No. 10, Oct. 14, 2010, pp. 1-14.

Guberina et al., Association of High HLA-E Expression During Acute Cellular Rejection and Nos. of HLA Class I Leader Peptide Mismatches with Reduced Renal Allograft Survival, Immunobiology, vol. 222, Mar. 2017, pp. 536-543.

Gunther et al., Novel Multivariate Methods for Integration of Genomics and Proteomics Data: Applications in a Kidney Transplant Rejection Study, Omics, A Journal of Integrative Biology, vol. 18, No. 11, Nov. 2014, pp. 682-695.

Halloran, Identifying Subphenotypes of Antibody-Mediated Rejection in Kidney Transplants, American Journal of Transplantation, vol. 16, No. 3, Mar. 2016, pp. 908-920.

Halloran et al., Real Time Central Assessment of Kidney Transplant Indication Biopsies by Microarrays: The INTERCOMEX Study, American Journal of Transplantation, vol. 17, No. 11, Nov. 2017, pp. 2851-2862.

Halloran et al., Review: The Transcripts Associated with Organ Allograft Rejection, American Journal of Transplantation, vol. 18, Nov. 17, 2017, pp. 785-795.

Hans et al., Shotgun Stochastic Search for "Large p" Regression, Journal of the American Statistical Association, vol. 102, No. 478, Jun. 2007, pp. 507-516.

Hart et al., OPTN/SRTR 2017 Annual Data Report: Kidney, American Journal of Transplantation, vol. 19, Feb. 2019, pp. 1-105.

Hayden et al., Regulation of NF-KB by TNF Family Cytokines, Seminars in Immunology, vol. 26, No. 3, Jun. 2014, pp. 253-266.

Hourmant, Frequency and Clinical Implications of Development of Donor-Specific and Non-Donor-Specific HLA Antibodies after Kidney Transplantation, Journal of the American Society of Nephrology, vol. 16, No. 9, Sep. 2005, pp. 2804-2812.

Jassal et al., The Reactome Pathway Knowledgebase, Nucleic Acids Research, vol. 48, Nov. 6, 2019, pp. D498-D503.

Kalliolias et al., TNF Biology, Pathogenic Mechanisms and Emerging Therapeutic Strategies, Nature Reviews Rheumatology, vol. 12, Jan. 2016, pp. 49-62.

Keslar et al., Multicenter Evaluation of a Standardized Protocol for Noninvasive Gene Expression Profiling, American Journal of Transplantation, vol. 13, No. 7, Jun. 26, 2013, pp. 1891-1897.

Khatri et al., A Common Rejection Module (CRM) for Acute Rejection Across Multiple Organs Identifies Novel Therapeutics for Organ Transplantation, Journal of Experimental Medicine, vol. 210, No. 11, Oct. 21, 2013, pp. 2205-2221.

Kramer et al., Polymorphism in NFKBIA Gene is Associated with Recurrent Acute Rejections in Liver Transplant Recipients, Tissue Antigens, vol. 84, No. 4, Oct. 2014, pp. 370-377.

Kuleshov et al., Enrichr: A Comprehensive Gene Set Enrichment Analysis Web Server 2016 Update, Nucleic Acids Research, vol. 44, May 3, 2016, pp. W90-W97.

Kurian et al., Molecular Classifiers for Acute Kidney Transplant Rejection in Peripheral Blood by Whole Genome Gene Expression Profiling, American Journal of Transplantation, vol. 14, No. 15, May 2014, pp. 1164-1172.

Kurian et al., Orthogonal Comparison of Molecular Signatures of Kidney Transplants with Subclinical and Clinical Acute Rejection: Equivalent Performance Is Agnostic to Both Technology and Platform, American Journal of Transplantation, vol. 17, No. 8, Aug. 2017, pp. 2103-2116.

Lamb et al., Long-Term Renal Allograft Survival in the United States: A Critical Reappraisal, American Journal of Transplantation, vol. 11, No. 3, Mar. 2011, pp. 450-462.

(56) References Cited

OTHER PUBLICATIONS

Leek et al., The sva Package for Removing Batch Effects and Other Unwanted Variation in High-Throughput Experiments, Bioinformatics, vol. 28, No. 6, Mar. 15, 2012, pp. 882-883.

Li et al., A Peripheral Blood Diagnostic Test for Acute Rejection in Renal Transplantation, American Journal of Transplantation, vol. 12, No. 10, Jun. 12, 2012, pp. 2710-2718.

Loupy et al., Subclinical Rejection Phenotypes at 1 Year Post-Transplant and Outcome of Kidney Allografts, Journal of the American Society of Nephrology, vol. 26, No. 7, Jul. 2015, pp. 1721-1731.

Mas et al., Targeted Degradation of TOC1 by ZTL Modulates Circadian Function in Arabidopsis Thaliana, Nature, vol. 426, Dec. 4, 2003, pp. 567-570.

McShane et al., In Pursuit of Greater Reproducibility and Credibility of Early Clinical Biomarker Research, Clinical and Translational Science, vol. 10, No. 2, Jan. 16, 2017, pp. 58-60.

Meier-Kriesche et al., Long-Term Renal Allograft Survival: Have We Made Significant Progress or Is It Time to Rethink Our Analytic and Therapeutic Strategies?, American Journal of Transplantation, vol. 4, No. 8, Aug. 2004, pp. 1289-1295.

Meng et al., Comparison of Rejection-Specific Genes in Peripheral Blood and Allograft Biopsy from Kidney Transplant, Transplantation Proceedings. vol. 50, Jan.-Feb. 2018, pp. 115-123.

Morey et al., Microarray Validation: Factors Influencing Correlation Between Oligonucleotide Microarrays and Real-time PCR, Biological Procedures Online, vol. 8, Feb. 2006, pp. 175-193.

Naesens et al., Progressive Histological Damage in Renal Allografts is Associated with Expression of Innate and Adaptive Immunity Genes, Kidney International, vol. 80, No. 12, Dec. 2011, pp. 1-26.

Nankivell et al., The Causes, Significance and Consequences of Inflammatory Fibrosis in Kidney Transplantation: The Banff i-IFTA Lesion, American Journal of Transplantation, vol. 18, No. 2, Dec. 2017, pp. 364-376.

Park et al., A Meta-analysis of Kidney Microarray Datasets: Investigation of Cytokine Gene Detection and Correlation with rt-PCR and Detection Thresholds, BMC Genomics, vol. 8, No. 1, Mar. 30, 2007, pp. 1-9,.

Park et al., Fibrosis with Inflammation at One Year Predicts Transplant Functional Decline, Journal of the American Society of Nephrology, vol. 21, Nov. 2010, pp. 1987-1997.

Reeve et al., Assessing Rejection-related Disease in Kidney Transplant Biopsies Based on Archetypal Analysis of Molecular Phenotypes, JCI Insight, vol. 2, No. 12, Jun. 15, 2017, pp. 1-14.

Reeve et al., Molecular Diagnosis of T Cell-mediated Rejection in Human Kidney Transplant Biopsies, American Journal of Transplantation, vol. 13, No. 3, Mar. 2013, pp. 645-655.

Roedder et al., The kSORT Assay to Detect Renal Transplant Patients at High Risk for Acute Rejection: Results of the Multicenter AART Study, PLOS Medicine, vol. 11, No. 11, Nov. 2014, pp. 1-15.

Rush et al., Beneficial Effects of Treatment of Early Subclinical Rejection: A Randomized Study, Journal of the American Society of Nephrology, vol. 9, No. 11, Nov. 1998, pp. 2129-2134.

Saint-Mezard et al., Analysis of Independent Microarray Datasets of Renal Biopsies Identifies a Robust Transcript Signature of Acute Allograft Rejection, Transplant International, vol. 22, No. 3, Mar. 2009, pp. 293-302.

Seifert et al., Subclinical Inflammation Phenotypes and Long-term Outcomes After Pediatric Kidney Transplantation, American Journal of Transplantation, vol. 18, No. 9, Sep. 2018, pp. 2189-2199.

Selleck et al., Making Meaningful Clinical Use of Biomarkers, Biomarker Insights, vol. 12, Nos. 1-7, Jun. 19, 2017, pp. 1-7.

Shen-Orr et al., Cell Type-Specific Gene Expression Differences in Complex Tissues, Nature Methods, vol. 7, No. 4, Apr. 2010, pp. 287-289.

Sidgel et al., A Rapid Noninvasive Assay for the Detection of Renal Transplant Injury, Transplantation, vol. 96, No. 1, Jul. 15, 2013, pp. 1-10.

Stegall et al., Developing New Immunosuppression for the Next Generation of Transplant Recipients: The Path Forward, American Journal of Transplantation, vol. 16, No. 4, Apr. 2016, pp. 1094-1101.

Szklarczyk et al., STRING v11: Protein-protein Association Networks with Increased Coverage, Supporting Functional Discovery in Genome-wide Experimental Datasets, Nucleic Acids Research, vol. 47, Nov. 22, 2018, pp. D607-D613.

Ventura et al., Discovery and Cross-Validation of Peripheral Blood and Renal Biopsy Gene Expression Signatures from Ethnically Diverse Kidney Transplant Populations, American Journal of Transplantation, vol. 19, No. 12, Dec. 2019, pp. 3356-3366.

Vincenti et al., A Phase III Study of Belatacept-Based Immunosuppression Regimens Versus Cyclosporine in Renal Transplant Recipients (BENEFIT Study), American Journal of Transplantation, vol. 10, No. 3, Mar. 2010, pp. 535-546.

Vyas et al., The Known Unknowns of Antigen Processing and Presentation, Nature Reviews Immunology, vol. 8, Aug. 2008, pp. 607-618.

Wiebe et al., Evolution and Clinical Pathologic Correlations of De Novo Donor-Specific HLA Antibody Post Kidney Transplant, American Journal of Transplantation, vol. 12, No. 5, May 2012, pp. 1157-1167.

* cited by examiner

GENE SIGNATURES FOR MONITORING ACUTE REJECTION AND METHODS OF USING SAME

PRIOR RELATED APPLICATION

This application claims the benefit of and priority to U.S. Provisional Application No. 63/017,695 filed on Apr. 30, 2020, which is hereby incorporated by reference in its entirety.

FIELD

This disclosure describes compositions and methods for monitor and treating acute transplant rejection.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 106707-1244770_seqlist.txt, created on Apr. 30, 2021, and having a size of 109 kb, and is filed concurrently with the specification. The sequence listing contained in this ASCII formatted document is part of the specification and is herein incorporated by reference in its entirety.

BACKGROUND

Despite advancements in clinical care for kidney transplant patients, long term outcomes remain sub-optimal. The reported incidence of acute rejection (AR)—including antibody mediated rejection (ABMR) and T cell mediated rejection (TCMR)—in the first year after transplantation varies depending on the immunosuppression utilized. It is typically higher with steroid and calcineurin inhibitor minimization or Belatacept-based regimens, though these regimens are often preferred for younger recipients as the reduction in long-term side effects is thought to offset the increased risk of early, treatable AR. Regardless, AR has been associated with decreased long-term allograft survival in both pediatric and adult studies. Additionally, TCMR has been correlated with formation of de novo donor specific antibody (dnDSA) which is strongly associated with premature allograft loss. Finally, AR is often associated with inflammation within areas of interstitial fibrosis and tubal atrophy (i-IFTA) at one year that is also correlated with decreased allograft survival. Immune monitoring to detect AR allows for early intervention and decreased graft damage, but diagnostic methods, particularly those relying on molecular signatures, are lacking, as these methods can be influenced by differences in the immunosuppressive strategies used, and these differences are non-uniformly distributed by recipient age. There is a need for compositions and methods for detection of both TCMR and ABMR in pediatric and adult patients, regardless of immunosuppression regimen utilized.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the findings by the inventors of a unique age-independent gene signature for acute transplant rejections that is effective across a broad array of immunosuppressive regimens.

Provided herein is a method for treating acute rejection (AR) of a transplant in a subject comprising: (a) measuring expression levels of two or more genes selected from the group consisting of DIP2C, ENOSF1, FBXO21, KCTD6, PDXDC1, REXO2, HLA-E, and RAB31 in a biological sample from a subject having a transplant, wherein differential expression of two or more genes selected from the group consisting of DIP2C, ENOSF1, FBXO21, KCTD6, PDXDC1, REXO2, HLA-E, and RAB31, as compared to control, indicates the subject has an increased likelihood of AR of the transplant; and (b) administering an effective amount of corticosteroid or antibody therapy to the subject.

In some embodiments, the expression levels of DIP2C, ENOSF1, FBXO21, KCTD6, PDXDC1, REXO2, HLA-E, and RAB31 are measured. In some embodiments, differential expression results in a genetic signature wherein DIP2C, ENOSF1, FBXO21, KCTD6, PDXDC1 and REXO2 are downregulated, and wherein HLA-E and RAB31 are upregulated.

In some embodiments, mRNA expression levels are measured. In some embodiments, protein expression levels are measured.

In some embodiments, the acute cellular rejection is T cell-mediated rejection (TCMR) or antibody-mediated rejection (ABMR).

In some embodiments, the transplant is a kidney transplant. In some embodiments, the subject is an adult. In some embodiments, the subject is a pediatric subject.

In some embodiments, the antibody is selected from the group consisting of a lymphocyte-depleting antibody, an anti-thymoglobin antibody, an anti-CD52 antibody, for example, alemtuzumab, and an anti-CD3 antibody.

In some embodiments, the method further comprises performing a biopsy on transplant tissue from the subject. In some embodiments, the method further comprises administering plasma exchange therapy, intravenous immunoglobulin (Ig) therapy, anti-IL-6 therapy, or a proteosomal inhibitor, if the biopsy shows antibody-mediated damage in the subject. In some embodiments, intravenous Ig therapy, an anti-IL-6 therapy, or a proteosomal inhibitor is administered in combination with rituximab.

Also provided is a kit comprising: (a) primers or probes for detection of two or more genes selected from the group consisting of DIP2C, ENOSF1, FBXO21, KCTD6, PDXDC1, REXO2, HLA-E, and RAB31.

DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A and FIG. 1C are PCA plots before and after normalization among renal samples. FIG. 1B and FIG. 1D are PCA plots before and after normalization among blood cell samples. These plots show the gene expression profiles of the samples plotted on the first two principal components.

Each point represents a sample, and samples from the same data set have the same color. These figures demonstrate there are no batch effects.

Figures 2A, 2B:
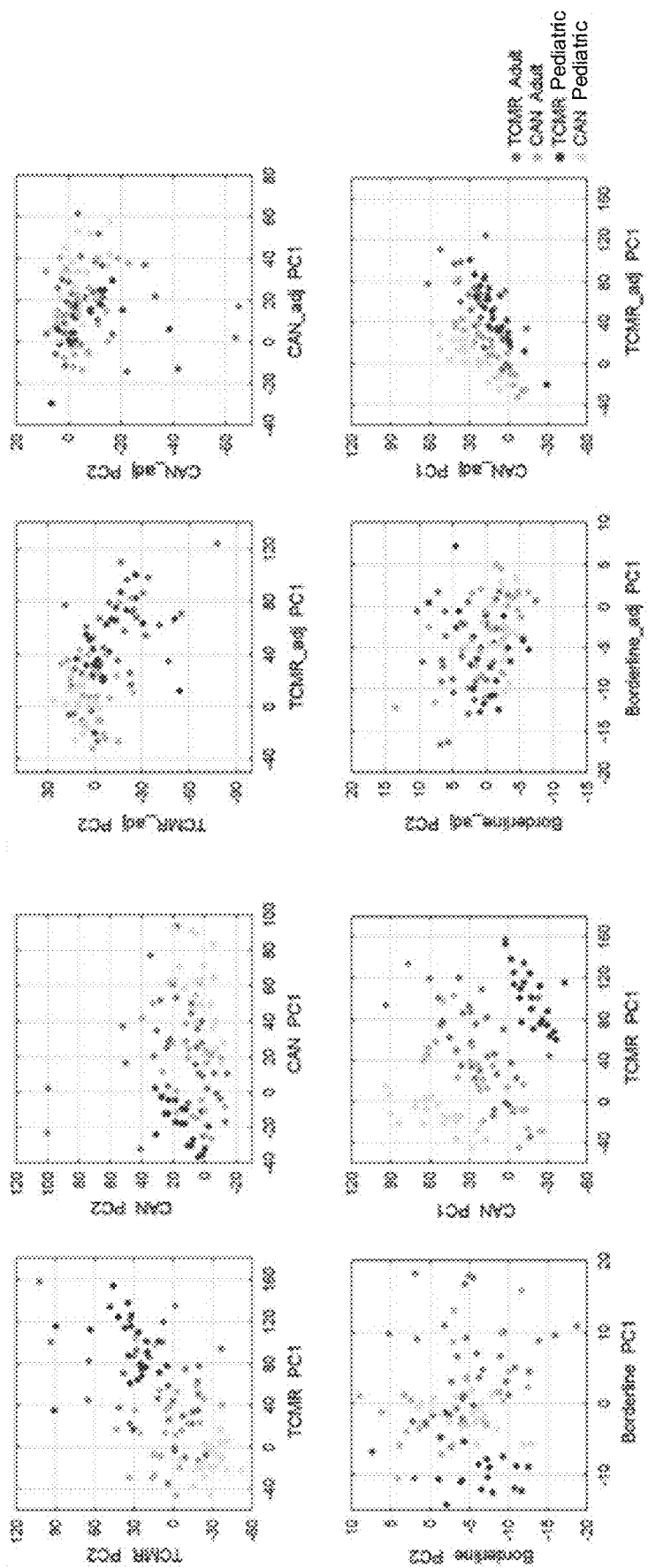
Figure 2D:
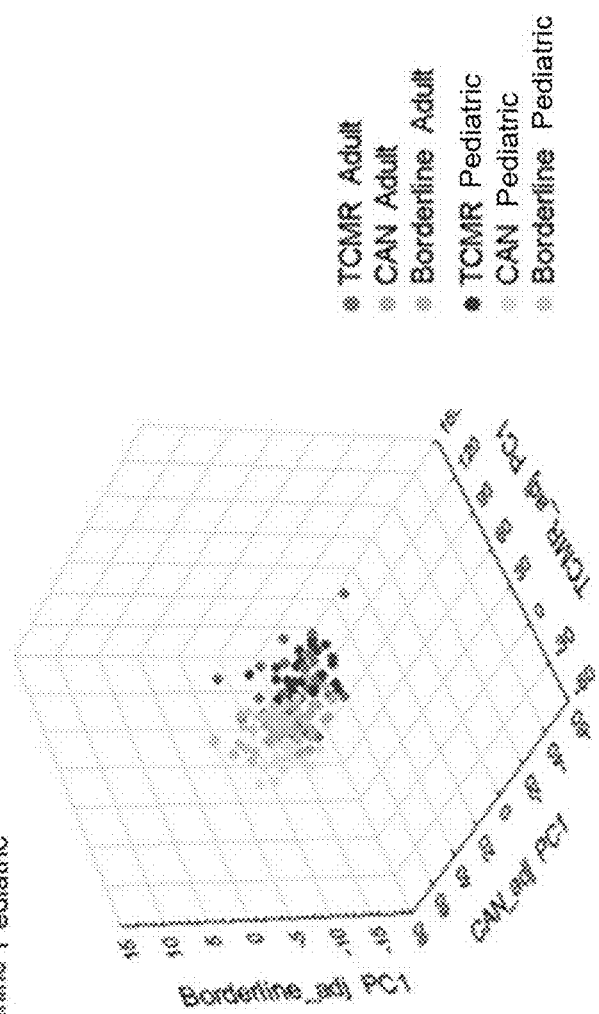
Figure 2C:
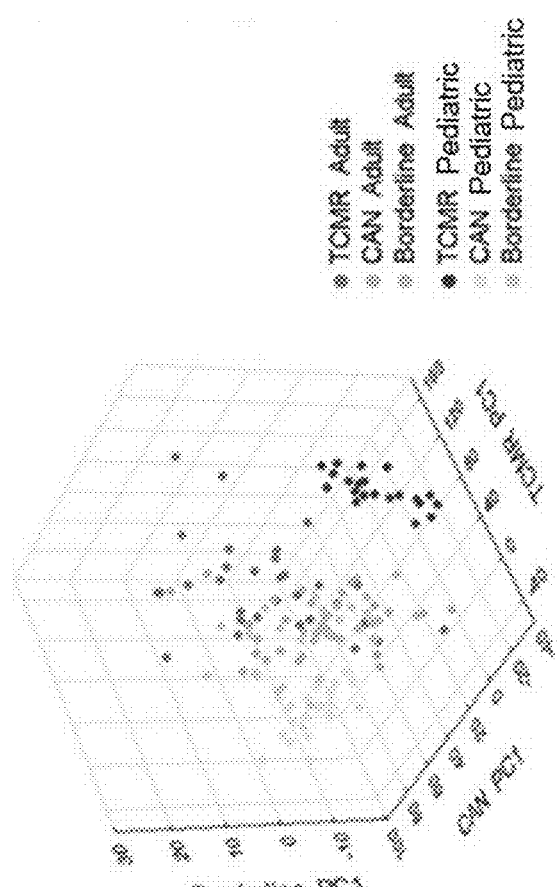

FIGS. 2A-2D are discordant gene expression profiles between adult and pediatric cases with renal allograft rejection according to certain embodiments of this disclosure. FIG. 2A shows PCA of TCMR, CAN and borderline associated genes reveal significant differences in TCMR and CAN gene profiles between adult and pediatric patients, but not in borderline samples. The upper left panel shows PCA of TCMR using first two principle components (PC1 and PC2) of differentially expressed probe sets between TCMR and STA. The bottom left panel shows PCA of borderline samples using first two principle components (PC1 and PC2) of differential expressed probe sets between borderline and STA. The upper right panel shows PCA of CAN using the first two principle components (PC1 and PC2) of differentially expressed probe sets between CAN and STA. The bottom right panel shows sample distribution defined using PC1 of TCMR associated probe sets and PC1 of CAN associated probe sets, colored by sample type. FIG. 2B shows PCA of TCMR, CAN, and borderline rejection after removal of Age-related differentially expressed genes. FIG. 2C shows 3D PCA of TCMR, CAN and borderline associated genes prior to removing differentially expressed genes between children and adults. FIG. 2D shows 3D PCA of TCMR, CAN and borderline associated genes after removing differentially expressed genes between children and adults yields.

Figure 3:
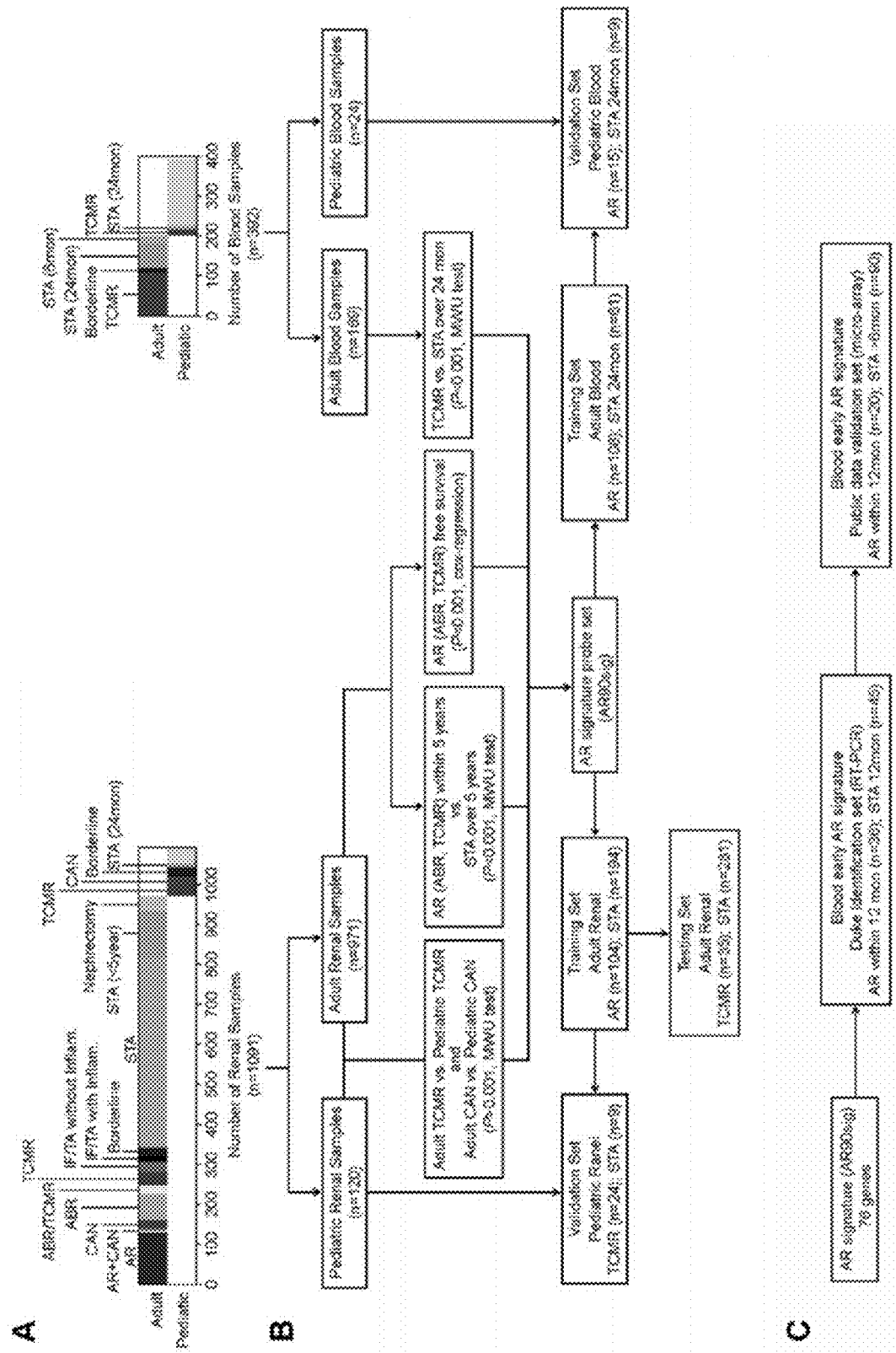

FIG. 3 are schematics showing a workflow for developing age-independent signature of AR using both renal and blood cell samples according to certain embodiments of this disclosure. Part A across the top of the drawing shows a description of clinical samples used in creation of an initial 90 probe set signature. Part B across the middle of the drawing illustrates a workflow showing the multiple comparisons made to identify the initial 90 probe sets. Part C across the bottom of the drawing shows a workflow for identifying early AR predictor.

Figure 4A:
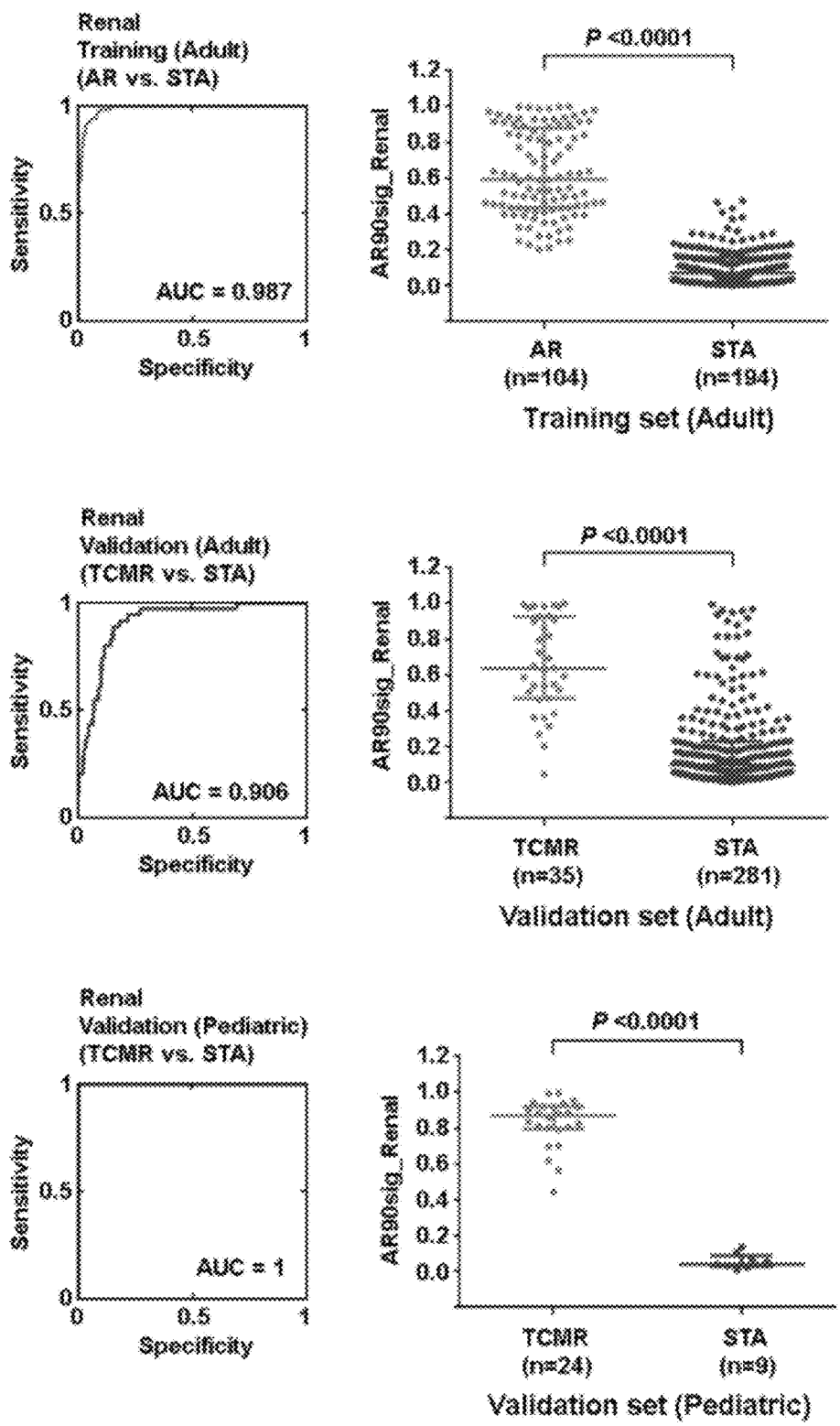
Figure 4B:
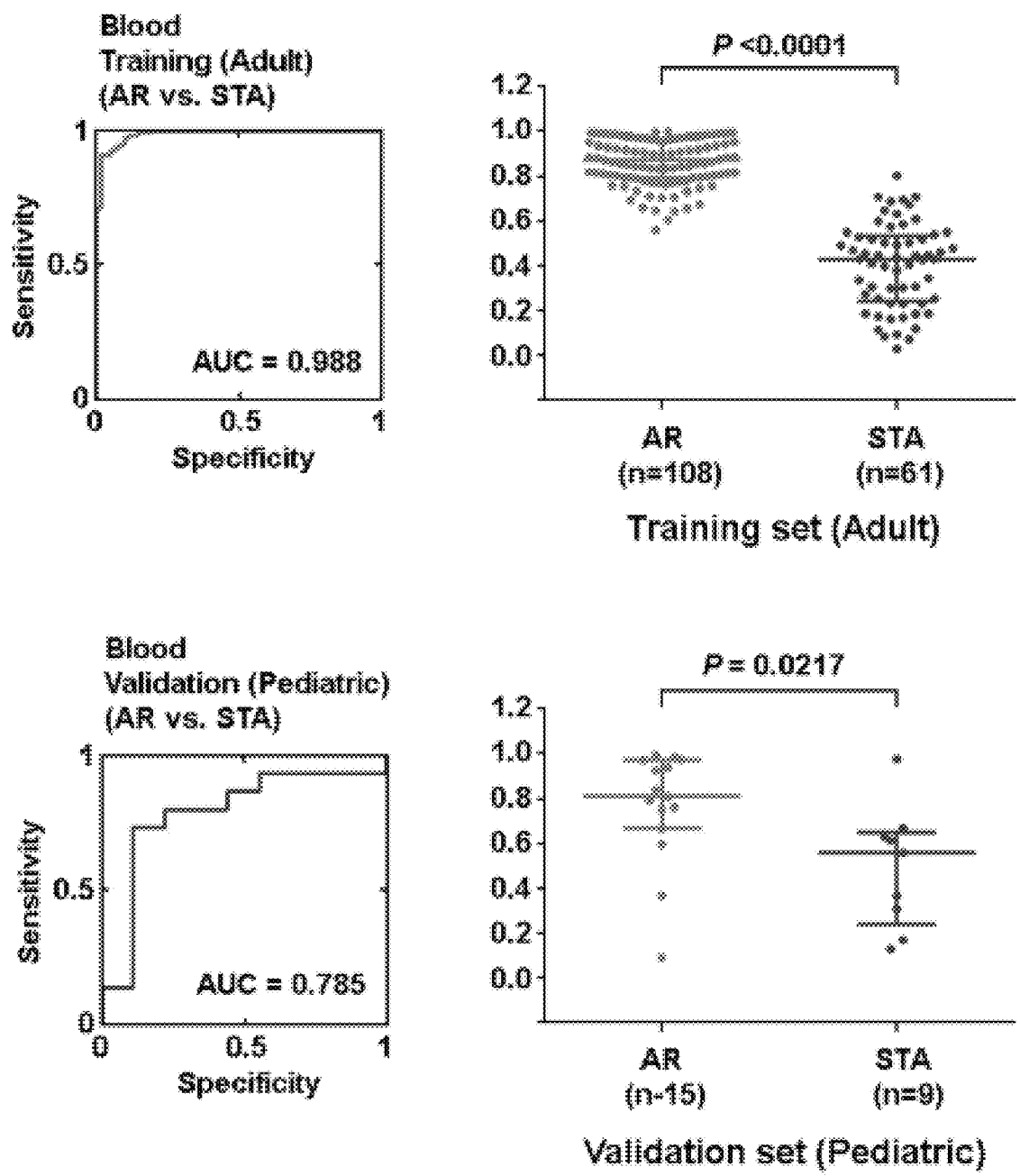
Figure 4C:
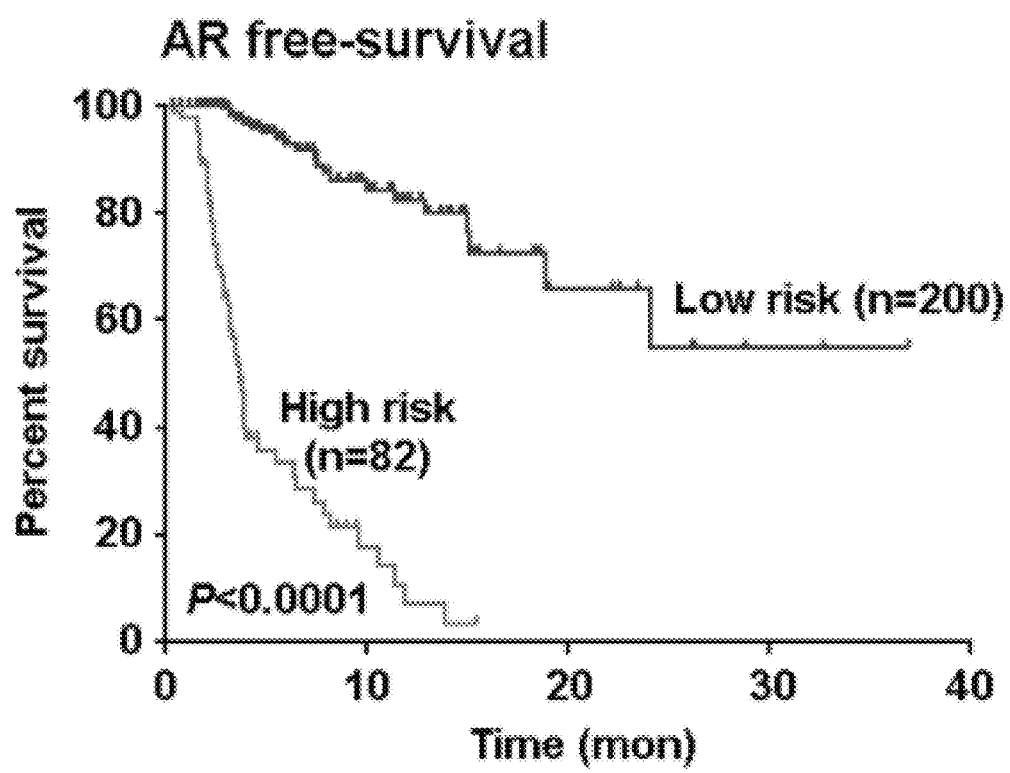

FIGS. 4A-4C are graphs showing an age-independent signature AR in renal parenchymal and peripheral blood samples according to certain embodiments of this disclosure. (A) 90-probe set model for the identification of AR event 5 years post-transplant using renal tissue samples. (B) 90-probe sets model for the identification of AR event 5 years post-transplant using blood cells. (C) AR-free survival between high and low AR risk groups defined by renal AR signature. ROC curves are plotted with AUCs noted (left panel). Logistic regression analysis was performed using non-parametric Mann-Whitney U test, lines represent median and interquartile range.

Figure 5A:
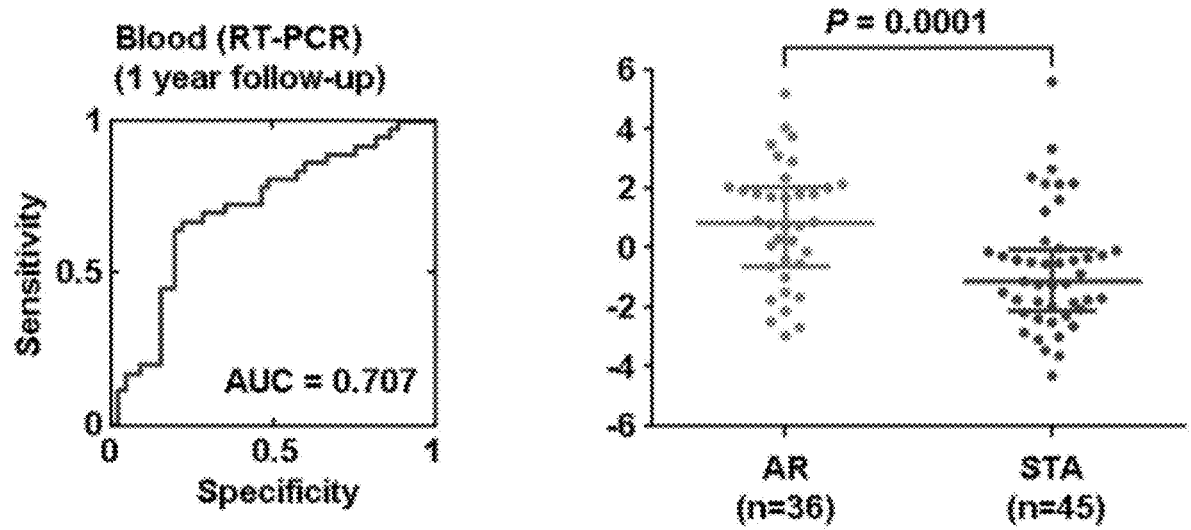
Figure 5B:
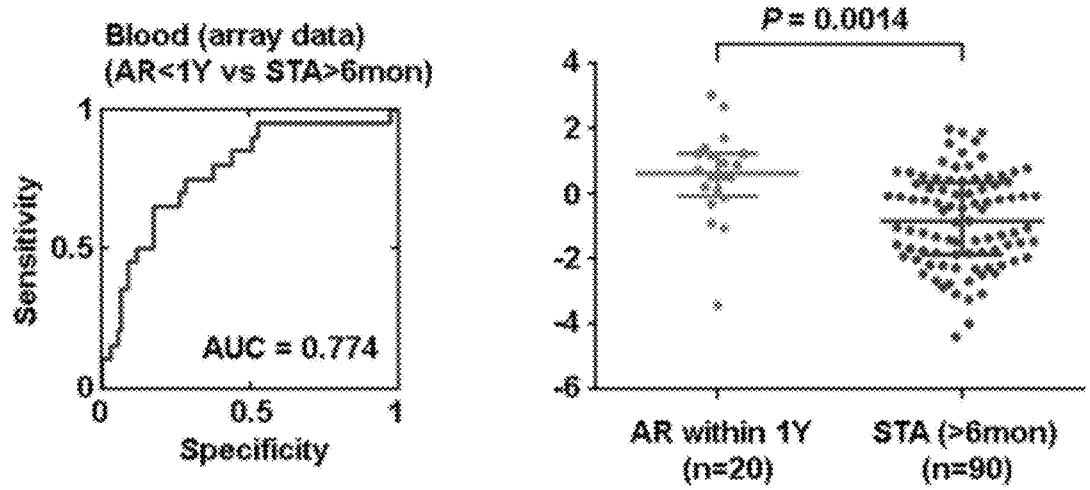

FIGS. 5A-5B are graphs showing validation of AR signature in vitro and in silico using independent data sets according to certain embodiments of this disclosure. FIG. 5A shows a ROC curve of 8-gene indentifier of AR event within 1 year after kidney transplant using Duke blood cell samples(training set). FIG. 5B shows a ROC curve of 8-gene identifier of AR event within 1 year after kidney transplant by in silico analysis (testing set). Logistic regression analysis was performed using non-parametric Mann-Whitney U test, lines represent median and interquartile range.

Figure 6:
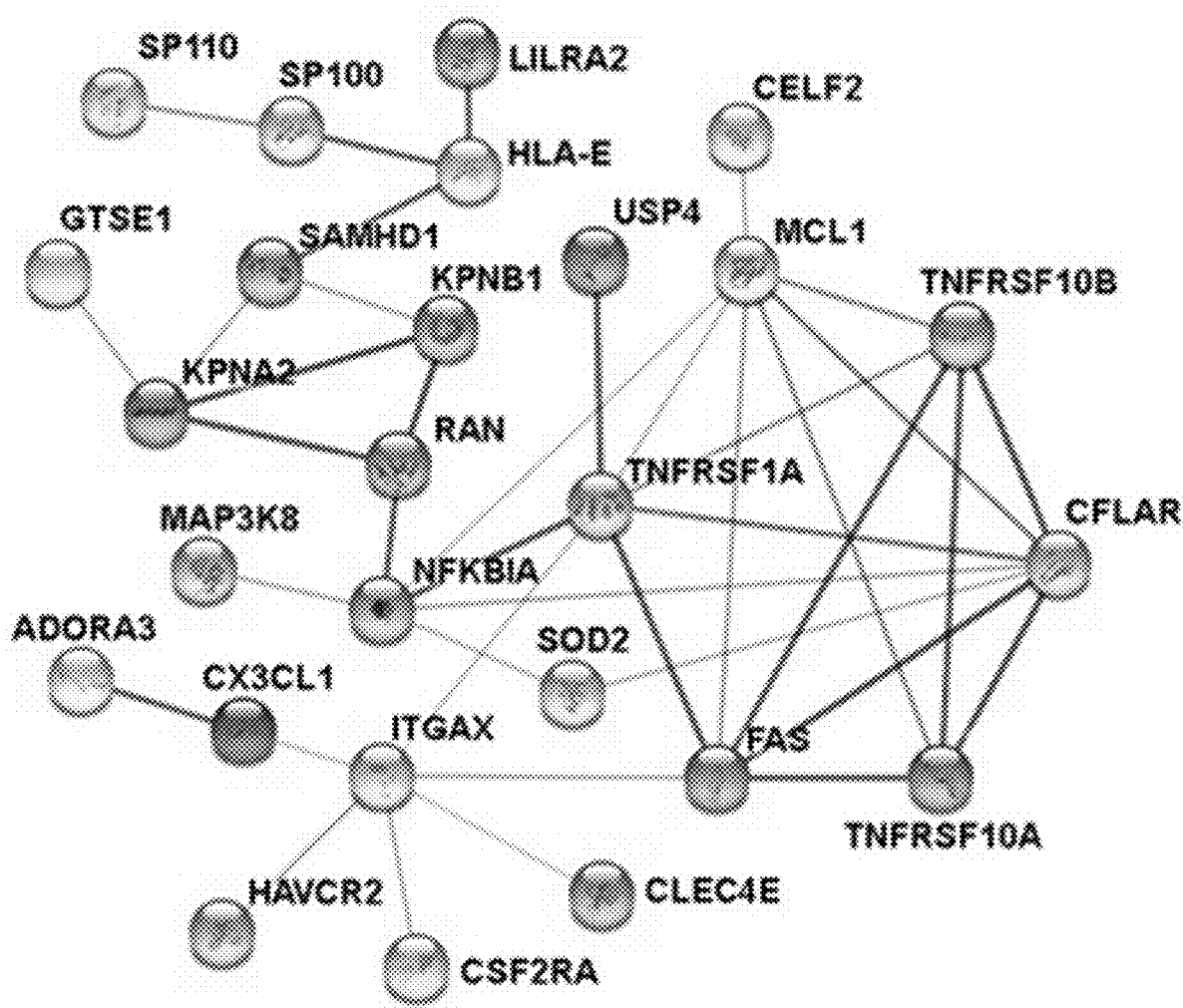

FIG. 6 is a schematic showing a novel gene network using STRING v11 that included the pathways noted in Example 1 in accordance with an embodiment of the present disclosure.

DETAILED DESCRIPTION

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Organ transplantation or the transfer of an organ from one human to another continues to rise throughout the world as the treatment of choice when an organ is irreversibly damaged or organ function is severely impaired. Organ transplantation is not without complications, not only from the transplant surgery itself, but also from the transplant recipient's own immune system and this process, if it happens suddenly, is called acute rejection. For example, when acute rejection of a kidney transplant occurs, it manifests itself by a sudden deterioration in kidney transplant function. About 30 percent of transplant recipients experience an episode of acute rejection. Acute rejection can be associated with reduction in the one-year survival rate of kidney grafts from a deceased donor of about 20 percent, and the projected half-life is about four years shorter in patients who have had an episode of acute rejection compared to patients who have not had an episode of acute rejection.

Sometimes, acute rejection can result from the activation of recipient's T cells and/or B cells. The rejection primarily due to T cells is classified as T cell mediated acute rejection or acute cellular rejection (ACR) and the rejection in which B cells are primarily responsible is classified as antibody mediated acute rejection (AMR). Often times, acute rejection of either type can result in the complete loss of transplant function and transplant failure.

An increase in the level of serum creatinine, a clinically used measure of kidney function, is often the first clinical indicator of acute rejection, and is currently the best surrogate marker of acute rejection of either type. However, this biomarker lacks sensitivity and specificity because graft dysfunction can occur due to non-immunological causes. Further, numerous therapies are used to prevent AR that differ by center and recipient age. This variability confounds diagnostic methods.

Currently, acute rejection is diagnosed by performing an invasive core needle biopsy procedure, which obtains a biopsy of the kidney graft. The histological features in the allograft biopsy tissues are then observed. However, this invasive biopsy procedure is associated with complications such as bleeding, arteriovenous fistula, graft loss, and, in severe cases, even death. Development of a noninvasive and/or minimally invasive test either to anticipate an episode of acute rejection or to diagnose acute rejection without performing the transplant biopsy procedure is a major and an unmet goal in organ transplantation.

Provided herein is a age-independent gene signature for AR effective across a broad array of immunosuppressive regimens. As described in the Examples, kidney transplant biopsy and peripheral blood gene expression profiles from twelve independent public datasets were compiled. After removing genes differentially expressed in pediatric and adults, gene expression profiles from biopsy and peripheral blood samples of patients with AR were compared to those who were stable (STA), using Mann-Whitney U Tests with validation in independent testing datasets. A novel age-independent gene network that identified AR from both kidney and blood samples, irrespective of immunosuppression regimen or recipient age, was identified. This signature was confirmed in pediatric and adult patients.

Methods

Provided herein is a method for treating acute rejection (AR) of a transplant in a subject comprising, consisting essentially of, or consisting of: (a) measuring expression levels of two or more genes selected from the group consisting of DIP2C, ENOSF1, FBXO21, KCTD6, PDXDC1, REXO2, HLA-E, and RAB31 in a biological sample from a subject having a transplant, wherein differential expression of two or more genes selected from the group consisting of DIP2C, ENOSF1, FBXO21, KCTD6, PDXDC1, REXO2, HLA-E, and RAB31, as compared to control, indicates the subject has an increased likelihood of AR of the transplant; and (b) administering an effective amount of a corticosteroid or antibody therapy to the subject.

In some embodiments, the expression levels of two or more, three or more, four or more, five or more, six or more, or seven or more genes selected from the group consisting of DIP2C, ENOSF1, FBXO21, KCTD6, PDXDC1, REXO2, HLA-E, and RAB31 are measured. In some embodiments, the expression levels of DIP2C, ENOSF1, FBXO21, KCTD6, PDXDC1, REXO2, HLA-E, and RAB31 are measured. In some embodiments, differential expression results in a genetic signature wherein DIP2C, ENOSF1, FBXO21, KCTD6, PDXDC1 and REXO2 are downregulated, and wherein HLA-E and RAB31 are upregulated. In some embodiments, differential expression results in a genetic signature wherein DIP2C, ENOSF1, FBXO21, KCTD6, PDXDC1 and REXO2 are downregulated, and wherein HLA-E and RAB31 are upregulated.

Also provided is a method for treating AR of a transplant in a subject comprising, consisting essentially of, or consisting of: administering an effective amount of a corticosteroid or antibody therapy to a subject having differential expression of two or more genes selected from the group consisting of DIP2C, ENOSF1, FBXO21, KCTD6, PDXDC1, REXO2, HLA-E, and RAB31, as compared to control. In some embodiments, the subject has differential expression of two or more, three or more, four or more, five or more, six or more, or seven or more genes selected from the group consisting of DIP2C, ENOSF1, FBXO21, KCTD6, PDXDC1, REXO2, HLA-E, and RAB31. In some embodiments, differential expression results in a genetic signature wherein DIP2C, ENOSF1, FBXO21, KCTD6, PDXDC1, and/or REXO2 are downregulated, and wherein HLA-E and/or RAB31 are upregulated. In some embodiments, differential expression results in a genetic signature wherein DIP2C, ENOSF1, FBXO21, KCTD6, PDXDC1 and REXO2 are downregulated, and wherein HLA-E and RAB31 are upregulated.

Also provided is a method for identifying an increased likelihood of acute rejection (AR) of a transplant in a subject comprising, consisting essentially of, or consisting of: measuring expression levels of two or more genes selected from the group consisting of DIP2C, ENOSF1, FBXO21, KCTD6, PDXDC1, REXO2, HLA-E, and RAB31 in a biological sample from a subject having a transplant, wherein differential expression of two or more of genes selected from the group consisting of DIP2C, ENOSF1, FBXO21, KCTD6, PDXDC1, REXO2, HLA-E, and RAB31, as compared to control, indicates the subject has an increased likelihood of AR of the transplant.

In some embodiments, the expression levels of two or more, three or more, four or more, five or more, six or more, or seven or more genes selected from the group consisting of DIP2C, ENOSF1, FBXO21, KCTD6, PDXDC1, REXO2, HLA-E, and RAB31 are measured to determine the likelihood of AR of a transplant in the subject. In some embodiments, the expression levels of DIP2C, ENOSF1, FBXO21, KCTD6, PDXDC1, REXO2, HLA-E, and RAB31 are measured to determine the likelihood of AR of a transplant in the subject. In some embodiments, differential expression results in a genetic signature wherein DIP2C, ENOSF1, FBXO21, KCTD6, PDXDC1 and/or REXO2 are downregulated, and wherein HLA-E and/or RAB31 are upregulated. In some embodiments, differential expression results in a genetic signature wherein DIP2C, ENOSF1, FBXO21, KCTD6, PDXDC1 and REXO2 are downregulated, and wherein HLA-E and RAB31 are upregulated.

As used throughout, by "subject" is meant an individual. The term "subject" and "patient" are used interchangeably herein and refer to both human and nonhuman animals The subject can be an adult subject or a pediatric subject. Adult subjects include subjects older than eighteen years of age. Pediatric subjects include subjects ranging in age from birth to eighteen years of age. Preferably, the subject is an animal, for example, a mammal such as a primate, and, more preferably, a human. Non-human primates are subjects as well. The term subject includes cats, dogs, reptiles, amphibians, livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

As used herein, a "biological sample" includes any sample obtained from a subject. A sample may contain tissue, cells, proteins, nucleic acids or other cellular matter. A sample may also be the liquid phase of a body fluid from which sedimentary materials have been substantially removed. Exemplary samples include, but are not limited to, blood samples containing peripheral blood mononuclear cells (PBMCs), plasma, urine samples containing urinary cells, fluid "supernatant" that is substantially free of cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft. A sample may also be obtained from essentially any body fluid including: blood (including peripheral blood), lymphatic fluid, sweat, peritoneal fluid, pleural fluid, bronchoalveolar lavage fluid, pericardial fluid, gastrointestinal juice, bile, urine, feces, tissue fluid or swelling fluid, joint fluid, cerebrospinal fluid, or any other named or unnamed fluid gathered from the anatomic area in proximity to the allograft or gathered from a fluid conduit in fluid communication with the allograft. For example, the sample can be a urinary cell sample. A "post-transplantation sample" refers to a sample obtained from a subject after the transplantation has been performed.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "recipient" (or "host"). An organ, or graft, transplanted between two genetically different individuals of the same species is called an "allograft." A graft transplanted between individuals of different species can be referred to as a "xenograft."

As used herein, "transplant rejection" refers to a functional and structural deterioration of the organ due to an active immune response expressed by the recipient, and independent of non-immunologic causes of organ dysfunction. Acute transplant rejection (AR) can result from the activation of recipient's T cells and/or B cells. A rejection primarily due to T cells is classified as T cell mediated acute rejection (TCR) (also known as acute cellular rejection (ACR)), and a rejection in which B cells are primarily responsible is classified as antibody mediated acute rejection (AMR). In some embodiments, the methods and compositions provided can detect and/or predict acute cellular rejection.

As used throughout, the term "gene" refers to a nucleic acid, DNA or RNA, involved in producing or encoding a polypeptide. It may include non-coding regions preceding and following the coding region (leader and trailer) as well as intervening sequences (introns) between individual coding segments (exons). As used throughout, the term "nucleic acid" or "nucleotide" refers to deoxyribonucleic acids (DNA) or ribonucleic acids (RNA) and polymers thereof in either single- or double-stranded form. It is understood that when a DNA sequence is described, its corresponding RNA is also described, wherein thymidine is represented as uridine. Unless otherwise indicated, a particular nucleic acid sequence also implicitly encompasses modified variants thereof, alleles, orthologs, SNPs, and complementary sequences as well as the sequence explicitly indicated.

Disco-interacting protein 2 homolog C (DIP2C) is a protein that shares a strong similarity with a Drosophila protein which interacts with transcription factor disco and is expressed in the nervous system. SEQ ID NO: 1, set forth under GenBAnk Accession No. NM_014974.3, is a representative nucleotide sequence encoding DIP2C. The nucleotide sequence of SEQ ID NO: 1 encodes a DIP2C polypeptide (SEQ ID NO: 2).

Homo sapiens enolase superfamily member 1 (ENOSF1) plays a role in catabolism of L-fucose, a sugar that is part of the carbohydrates attached to cellular glycoproteins. SEQ ID NO: 3, set forth under GenBAnk Accession No. NM_017512.7, is a representative nucleotide sequence encoding ENOSF1. The nucleotide sequence of SEQ ID NO: 3 encodes an ENOSF1 polypeptide (SEQ ID NO: 4).

F-box protein 21 (FBXO21) plays a role in phosphorylation-dependent ubiquitination. SEQ ID NO: 5, set forth under GenBAnk Accession No. NM_033624.3, is a representative nucleotide sequence encoding FBXO21. The nucleotide sequence of SEQ ID NO: 5 encodes a FBXO21 polypeptide (SEQ ID NO: 6).

Homo sapiens potassium channel tetramerization domain containing 6 (KCTD6) is a protein involved in activation of cAMP-dependent Protein Kinase A and the innate immune-system. SEQ ID NO: 7, set forth under GenBAnk Accession No. NM_153331.3, is a representative nucleotide sequence encoding KCTD6. The nucleotide sequence of SEQ ID NO: 7 encodes a KCTD6 polypeptide (SEQ ID NO: 8).

RNA exonuclease 2 (REXO2) is a 3'-to-5' exonuclease specific for small (primarily 5 nucleotides or less in length) single-stranded RNA and DNA oligomers. This protein may have a role in DNA repair, replication, and recombination, and in RNA processing and degradation. SEQ ID NO: 9, set forth under GenBAnk Accession No. NM_015523.4, is a representative nucleotide sequence encoding REXO2. The nucleotide sequence of SEQ ID NO: 9 encodes a REXO2 polypeptide (SEQ ID NO: 10).

Homo sapiens major histocompatibility complex, class I, E (HLA-E) is a non-classical MHC class 1 molecule that plays a role in cell recognition by natural killer cells. SEQ ID NO: 11, set forth under GenBAnk Accession No. NM_005516.6, is a representative nucleotide sequence encoding HLA-E. The nucleotide sequence of SEQ ID NO: 11 encodes a HLA-E polypeptide (SEQ ID NO: 12).

Homo sapiens RAB31, member RAS oncogene family (RAB31) is a small GTPases that is a key regulator of intracellular membrane trafficking, from the formation of transport vesicles to their fusion with membrane. SEQ ID NO: 13, set forth under GenBAnk Accession No. NM_006868.4, is a representative nucleotide sequence encoding RAB31. The nucleotide sequence of SEQ ID NO: 13 encodes a RAB31 polypeptide (SEQ ID NO: 14).

Homo sapiens pyridoxal dependent decarboxylase domain containing 1 (PDXDC1) is a protein having carboxy-lyase activity and is associated with pyridoxal phosphate binding. SEQ ID NO: 15, set forth under GenBAnk Accession No. NM_015027.4, is a representative nucleotide sequence encoding PDXDC1. The nucleotide sequence of SEQ ID NO: 15 encodes a PDXDC1 polypeptide (SEQ ID NO: 16).

As used herein, the term "biomarker" includes a polynucleotide or polypeptide molecule which is differentially expressed, i.e., present, increased or decreased in quantity or activity, in subjects having acute rejection or likely to experience acute rejection.

As used herein, the term "gene signature" includes a group of biomarkers, the quantity or activity of each member of which is correlated with subjects having acute rejection or likely to experience acute rejection. In some embodiments, a panel of markers may include only those markers which are either increased in quantity or activity in those subjects. In some embodiments, the panel of markers include one, two, three, four, five, six, seven, or eight, of DIP2C, ENOSF1, FBXO21, KCTD6, PDXDC1, REXO2, HLA-E, and RAB31. In some embodiments, differential expression results in a gene signature wherein DIP2C, ENOSF1, FBXO21, KCTD6, PDXDC1 and REXO2 are downregulated, and wherein HLA-E and RAB31 are upregulated. In some embodiments, the signature is able to distinguish individuals having acute rejection or likely to experience acute rejection from individuals lacking acute rejection or unlikely to experience acute rejection.

As described in the Examples the gene signature provided herein distinguished acute rejection samples from non-acute rejection samples. Classification accuracy was determined using an area under the curve (AUC) measure. The "area under curve" or "AUC" refers to area under a receiver operating characteristic (ROC) curve. AUC under a ROC curve is a measure of accuracy. An area of 1 represents a perfect test, whereas an area of 0.5 represents an insignificant test. A preferred AUC may be between 0.700 and 1. For example, a preferred AUC may be at least approximately 0.700, at least approximately 0.750, at least approximately 0.750, at least approximately 0.800, at least approximately 0.810, at least approximately 0.820, at least approximately 0.830, at least approximately 0.840, at least approximately 0.850, at least approximately 0.860, at least approximately 0.870, at least approximately 0.880, at least approximately 0.890, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

As used herein, the "level" of expression means the amount of expression. The level or amount can be described as RNA copy number per microgram of total RNA in a sample or the amount of polypeptide in a sample. As used herein, a "control" or "Baseline level of gene expression" includes the particular gene expression level of a healthy subject or a subject with a well-functioning transplant. The baseline level of gene expression includes the gene expression level of a subject without acute rejection. The baseline level of gene expression can be a reference value, for example, a number on paper, or the baseline level of gene expression from a healthy subject, a subject with a well-functioning transplant, or a subject successfully treated for AR. In some embodiments, the reference value or baseline level of gene expression is from a subject at risk for AR.

In the methods provided herein, the level of expression is determined for one or more of the foregoing genes in a sample obtained from a subject. For example, the quantity of expression of at least two of the foregoing genes, or at least three of the foregoing genes, or at least four of the foregoing genes, or at least five of the foregoing genes, or at least six of the foregoing genes, or at least seven of the foregoing genes, or at least eight of the foregoing gense is determined. In some instances, the quantity of expression of at least five, six, seven, or eight of the foregoing genes is determined. In some embodiments, the quantity of expression of all eight of the foregoing genes is determined.

The term "level of gene expression" as used herein refers to a quantified amount of gene expression. Any procedure available to those of skill in the art can be employed to determine the expression levels of DIP2C, ENOSF1, FBXO21, KCTD6, PDXDC1, REXO2, HLA-E, and RAB31 or a combination thereof. For example, probes, primers, and/or antibodies can be employed in quantitative nucleic acid amplification reactions (e.g., quantitative polymerase chain reaction (PCR)), TAQMAN® assay, primer extension, Northern blot, immunoassay, immunosorbant assay (ELISA), radioimmunoassay (RIA), immunofluorimetry, immunoprecipitation, equilibrium dialysis, immunodiffusion, immunoblotting, mass spectrometry and other techniques available to the skilled artisan. In another example, a microarray can be used. Microarrays are known in the art and consist of a surface to which probes that correspond in sequence to gene products (e.g. mRNAs, rRNAs, polypeptides, fragments thereof etc.) can be specifically hybridized or bound to a known position. Hybridization intensity data detected by the scanner are automatically acquired and processed by the Affymetrix Microarray Suite (MASS) software. Raw data is normalized to expression levels using a target intensity of 150.

A "probe or primer" as used herein refers to a group of nucleic acids where one or more of the nucleic acids can be used to detect one or more genes (e.g., DIP2C, ENOSF1, FBXO21, KCTD6, PDXDC1, REXO2, HLA-E, and RAB31). Exemplary primers and probes for detection of DIP2C, ENOSF1, FBXO21, KCTD6, PDXDC1, REXO2, HLA-E, or RAB31 are set forth in Table 6. It is understood that sequences complementary to the probe sequences set forth in Table 6 are also provided herein. Exemplary primers for amplification of DIP2C, ENOSF1, FBXO21, KCTD6, PDXDC1, REXO2, HLA-E, and RAB31 are set forth herein in Table 6. As set forth above, the nucleic acid sequences encoding DIP2C, ENOSF1, FBXO21, KCTD6, PDXDC1, REXO2, HLA-E, and RAB31 are provided herein. Numerous techniques for identifying probes and/or primers, based on these sequences, that specifically amplify any of the biomarkers set forth herein are known to those of skill in the art.

Detection may be, for example, through amplification as in PCR, QPCR, RT-PCR, or primer extension. Detection can also be through hybridization, or through selective destruction and protection, as in assays based on the selective enzymatic degradation of single or double stranded nucleic acids, or by detecting RNA affixed to a solid surface (e.g., a blot). Probes and/or primers may be labeled with one or more fluorescent labels, radioactive labels, fluorescent quenchers, enzymatic labels, or other detectable moieties. Probes may be any size so long as the probe is sufficiently large to selectively detect the desired nucleic acid or to serve as a primer for amplification.

Primers can be polynucleotides or oligonucleotides capable of being extended in a primer extension reaction at their 3' end. In order for an oligonucleotide to serve as a primer, it typically needs only be sufficiently complementary in sequence to be capable of forming a double-stranded structure with the template, or target, under the conditions employed. Establishing such conditions typically involves selection of solvent and salt concentration, incubation temperatures, incubation times, assay reagents and stabilization factors known to those in the art. The term primer or primer oligonucleotide refers to an oligonucleotide as defined herein, which is capable of acting as a point of initiation of synthesis when employed under conditions in which synthesis of a primer extension product that is complementary to a nucleic acid strand is induced, as, for example, in a DNA replication reaction such as a PCR reaction. Like non-primer oligonucleotides, primer oligonucleotides may be labeled according to any technique known in the art, such as with radioactive atoms, fluorescent labels, enzymatic labels, proteins, haptens, antibodies, sequence tags, mass label or the like. Such labels may be employed by associating them, for example, with the 5' terminus of a primer by a plurality of techniques known in the art. Such labels may also act as capture moieties. A probe or primer may be in solution, as would be typical for multiplex PCR, or a probe or primer may be adhered to a solid surface, as in an array or microarray. It is well known that compounds such as PNAs may be used instead of nucleic acids to hybridize to genes. In addition, probes may contain rare or unnatural nucleic acids such as inosine.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "Tm". The Tm of a particular nucleic acid duplex under specified conditions is the temperature at which on average half of the base pairs have disassociated.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide if hybridization can occur between one of the strands of the first polynucleotide and the second polynucleotide. "Complementarity" or "homology" is quantifiable in terms of the proportion of bases in opposing strands that are expected to hydrogen bond with each other, according to generally accepted base-pairing rules.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. It is well-known in the art that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al. (1989); Nucleic Acid Hybridization, A Practical Approach, IRL Press, Washington D.C. 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42° C. in a solution consisting of 5.times.SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 ug/ml denatured salmon sperm DNA followed by washing in a solution comprising 0.1× SSPE, 1.0% SDS at 42° C. when a probe of about 500 nucleotides in length is employed. In general, the stringency of hybridization is determined by the wash step. Hence, a wash step involving 0.1×SSPE, 1.0% SDS at a temperature of at least 42° C. can yield a high stringency hybridization product. In some instances, the high stringency hybridization conditions include a wash in 1×SSPE, 1.0% SDS at a temperature of at least 50° C., or at about 65° C.

"Medium stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 ug/ml denatured salmon sperm DNA followed by washing in a solution comprising 1.0× SSPE, 1.0% SDS at 42° C. when a probe of about 500 nucleotides in length is employed. Hence, a wash step involving 1.0×SSPE, 1.0% SDS at a temperature of 42° C. can yield a medium stringency hybridization product.

"Low stringency conditions" include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed. Hence, a wash step involving 5×SSPE, 1.0% SDS at a temperature of 42° C. can yield low stringency hybridization product.

As used herein, the term polynucleotide or nucleic acid includes nucleotide polymers of any number. The term polynucleotide can, for example, have less than about 200 nucleotides. However, other polynucleotides can have more than 200 nucleotides. Probes and primers are polynucleotides. Primers can, for example, have between 5 and 100 nucleotides, or have about 15 to 100 nucleotides. Probes can have the same or longer lengths. For example, probes can have about 16 nucleotides to about 10,000 nucleotides. The exact length of a particular polynucleotide depends on many factors, which in turn depend on its ultimate function or use. Some factors affecting the length of a polynucleotide are, for example, the sequence of the polynucleotide, the assay conditions in terms of such variables as salt concentrations and temperatures used during the assay, and whether or not the polynucleotide is modified at the 5' terminus to include additional bases for the purposes of modifying the mass: charge ratio of the polynucleotide, or providing a tag capture sequence which may be used to geographically separate a polynucleotide to a specific hybridization location on a DNA chip, for example.

As used throughout, the term "up-regulation," "up-regulated," "increased expression," "higher expression," and "higher levels of expression" are used interchangeably herein and refer to the increase or elevation in the amount of a target RNA or polypeptide. "Up-regulation," "up-regulated," "increased expression," "higher expression," and "increased levels of expression include increases above a baseline (e.g., a control, or reference) level of 10%, 15%, 20%, 25%, 30%, 35%, 40%, 45%, 50%, 55%, 60%, 65%, 70%, 75%, 80%, 85%, 90%, 95%, 100%, 200% or higher.

As used throughout, the term "down-regulation," "down-regulated," "decreased expression," "lower expression," and "lower levels of expression" are used interchangeably herein and refer to the increase or elevation in the amount of a target RNA or polypeptide. "Down-regulation," "down-regulated," "decreased expression," "lower expression," and "lower levels of expression" include decreases below a baseline (e.g., a control, or reference) level of 10%, 15%, 20%, 25%, 30%, 35%, 40%, 45%, 50%, 55%, 60%, 65%, 70%, 75%, 80%, 85%, 90%, 95%, 99% or 100%.

In some embodiments, the expression levels DIP2C, ENOSF1, FBXO21, KCTD6, PDXDC1, REXO2, HLA-E, and RAB31 or a combination thereof are determined using respective probes or primers that can hybridize to the DIP2C, ENOSF1, FBXO21, KCTD6, PDXDC1, REXO2, HLA-E, and RAB31 genes. Sequences for DIP2C, ENOSF1, FBXO21, KCTD6, PDXDC1, REXO2, HLA-E, and RAB31 are provided herein and are also readily available and can be used to make such probes and primers.

The mRNA for DIP2C, ENOSF1, FBXO21, KCTD6, PDXDC1, REXO2, HLA-E, and RAB31 that are quantified using the methods described herein have RNA sequences that are the same or complementary to those recited above, except that these RNAs have uracil-containing nucleotides instead of the thymine-containing nucleotides recited in the sequences described herein.

The quantities of RNA expression are conveniently expressed as RNA copies per microgram of total RNA. A standard curve of RNA copy numbers in the selected RNA measurement (e.g., PCR) assays can range, for example, from 25 to 5 million copies, 25 to 3 million copies, or from 25 to 2.5 million copies. When mRNA copy numbers are measured as less than 25 can be scored as 12.5 copies per microgram of total RNA.

The DIP2C, ENOSF1, FBXO21, KCTD6, PDXDC1, REXO2, HLA-E, and/or RAB31 quantified using the methods described herein, and the probes and primers described herein can exhibit some variation of sequence from those recited herein. For example, the DIP2C, ENOSF1, FBXO21, KCTD6, PDXDC1, REXO2, HLA-E, and RAB31 quantified using the methods described herein, and the probes and primers described herein, can have at least 60% sequence identity, or at least 65% sequence identity, or at least 70% sequence identity, or at least 80% sequence identity, or at least 90%, or at least 91% sequence identity, or at least 93% sequence identity, or at least 95% sequence identity, or at least 96%, or at least 97% sequence identity, or at least 98% sequence identity, or at least 99% sequence identity, or at least 99.5% sequence identity to the sequences described herein. For example, also provided herein are sequences having at least 60%, 65%, 70%, 754%, 80%, 85%, 90%, 95%, 99% identity to any one of SEQ ID NOs: 1-112.

The term "identity" or "substantial identity", as used in the context of a polynucleotide sequence described herein, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, about 20 to 50, about 20 to 100, about 50 to about 200 or about 100 to about 150, in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (e.g., BLAST), or by manual alignment and visual inspection.

Algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 10-5, and most preferably less than about 10-20.

An alternative method for determining the level of DIP2C, ENOSF1, FBXO21, KCTD6, PDXDC1, REXO2, HLA-E, and RAB31 or a combination thereof includes the use of molecular beacons and other labeled probes useful in, for example multiplex PCR. In a multiplex PCR assay, the PCR mixture contains primers and probes directed to the DIP2C, ENOSF1, FBXO21, KCTD6, PDXDC1, REXO2, HLA-E, and RAB31 or a combination thereof. Typically, a single fluorophore is used in the assay. The molecular beacon or probe is detected to determine the level of DIP2C, ENOSF1, FBXO21, KCTD6, PDXDC1, REXO2, HLA-E, and RAB31 or a combination thereof. Molecular beacons are described, for example, by Tyagi and Kramer (Nature Biotechnology 14, 303-308, (1996)) and by Andrus and Nichols in U.S. Patent Application Publication No. 20040053284.

Another method includes, for instance, quantifying cDNA (obtained by reverse transcribing the DIP2C, ENOSF1, FBXO21, KCTD6, PDXDC1, REXO2, HLA-E, and RAB31 or a combination thereof using a fluorescence based real-time detection method, such as the ABI PRISM 7500, 7700, or 7900 Sequence Detection System (TaqMan®) commercially available from Applied Biosystems, Foster City, Calif., or similar system as described by Heid et al., (Genome Res. 1996; 6:986-994) and Gibson et al. (Genome Res. 1996; 6:995-1001).

Generally, the level of DIP2C, ENOSF1, FBXO21, KCTD6, PDXDC1, REXO2, HLA-E, and RAB31 or a combination thereof in a sample is upregulated if the quantity of expression of DIP2C, ENOSF1, FBXO21, KCTD6, PDXDC1, REXO2, HLA-E, and RAB31 or a combination thereof is increased beyond a baseline level. In some embodiments, upregulation includes increases above a baseline level of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000% or higher. In some instances, the "increased expression" means detection of expression that is greater than a baseline level by 2-fold, 3-fold, 5-fold, 7-fold, 8-fold, 9-fold, 10-fold, or more. "Increased expression" can also mean the 8-gene signature score of patients is significantly higher than a healthy individual or another control. The signature score can be calculated using principal component analysis (PCA), where the score of the first principal component will be used as signature score. See, for example, Berglund et al. "Characteristics and Validation Techniques for PCT-Based Gene-Expression Signatures," Int. J. Genomics, 2017: 2354564. As used herein, "significantly higher" means a false discovery rate (FDR)<0.05, nonparametric Mann-Whitney U test.

The level of expression of DIP2C, ENOSF1, FBXO21, KCTD6, PDXDC1, REXO2, HLA-E, and RAB31, or a combination of any thereof, in a sample is down-regulated if the quantity of expression of DIP2C, ENOSF1, FBXO21, KCTD6, PDXDC1, REXO2, HLA-E, and RAB31, or a combination of any thereof, is decreased below a baseline. For example, down-regulation can include decreases below a baseline level by 10%, 15%, 20%, 25%, 30%, 35%, 40%, 45%, 50%, 55%, 60%, 65%, 70%, 75%, 80%, 85%, 90%, 95%, 100% or more below the baseline.

The level of expression of DIP2C, ENOSF1, FBXO21, KCTD6, PDXDC1, REXO2, HLA-E, and RAB31, or a combination of any thereof, in a sample is generally unchanged if the quantity of expression of DIP2C, ENOSF1, FBXO21, KCTD6, PDXDC1, REXO2, HLA-E, and RAB31, or a combination of any thereof, does not vary significantly from a baseline. In such instances, a sample from a a transplanted tissue in patient having unchanged level of measured expression of DIP2C, ENOSF1, FBXO21, KCTD6, PDXDC1, REXO2, HLA-E, and RAB31 or a combination thereof likely is not being rejected (e.g., no acute rejection), and will likely not be rejected. For example, variance from a baseline level of 0.1%, 0.2%, 0.5%, 1%, 2%, 3%, 4% or less is not sufficiently significant and the level of DIP2C, ENOSF1, FBXO21, KCTD6, PDXDC1, REXO2, HLA-E, and RAB31 or a combination thereof in a sample is generally unchanged if such variance is measured.

The term "hybridization" includes a reaction in which one or more nucleic acids or polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two single strands forming a duplex structure, three or more strands forming a multi-stranded complex, a single self-hybridizing strand, or any combination of these. A hybridization reaction may constitute a step in a more extensive process, such as the initiation of a PCR reaction, primer extension reaction, or the enzymatic cleavage of a polynucleotide by a ribozyme.

In some embodiments, to accurately assess whether increased or decreased mRNA or rRNA is significant, the measured expression is "normalized" against a selected normalizer. Normalization of gene expression can allow more accurate comparison of levels of expression between samples. In some instances, the method comprises the steps of (a) measuring the gene expression levels of two or more genes selected from the group consisting of DIP2C, ENOSF1, FBXO21, KCTD6, PDXDC1, REXO2, HLA-E, and RAB3 lin a biological sample obtained from the subject, (b) normalizing the gene expression levels of the two or more genes to generate normalized gene expression levels, (c) inputting the normalized gene expression values into a classifier that discriminates between a classification for AR or increased likelihood of developing AR and a non-AR classification, wherein the classifier comprises pre-defined weighting values for each of the genes, (d) calculating a probability for having or developing AR based on the normalized gene expression values, to thereby determine if the subject has or is likely to develop AR, and (e) administering an effective amount of a corticosteroid or antibody therapy to the subject if the subject has been determined to have AR or is likely to develop AR.

Treatment

Any of the methods for determining the likelihood of acute rejection can be performed at any time after an organ transplant. For example, the likelihood of acute rejection can be determined one or more times after about 4 hours, 8 hours, 12 hours, 24 hours, two days, three, days, four days, five days, six days, one week, two weeks, three weeks, one month, two months, three months, four months, five months, five months, six months, seven months, eight months, nine months, ten months, eleven months, one year, 1.5 years, 2 years or more, post-transplantation. In some embodiments, a subject that is likely to develop acute rejection, also has elevated creatinine levels indicate of acute rejection. In some embodiments, a subject that is likely to develop acute rejection, has normal levels of creatinine levels, i.e., a gene signature set forth herein indicates that acute rejection is likely before an increase in creatinine levels.

The methods for determining an increased likelihood of an acute rejection (e.g., acute kidney rejection) can further include informing medical personnel or the patient about the test results. Information about whether the patient will have acute rejection can also be communicated. If the patient is likely to develop a dysfunction (e.g., kidney dysfunction), the patient can be prescribed and/or administered an effective amount of a treatment to delay rejection of the transplanted organ.

The methods of assaying for acute rejection (e.g., kidney rejection) can further include treatment for an acute rejection, such as kidney transplant rejection, acute tubular injury, T cell mediated rejection (TCR) or antibody-mediated rejection (AMR). Such treatment can include administering an increased or decreased dose of an anti-rejection agent already being administered to the subject. In some embodiments, a different anti-rejection agent can be administered. In some embodiments, an anti-rejection agent can be added to the subject's treatment, if the subject is not currently receiving anti-rejection treatment.

Also provided is a method for treating acute rejection (AR) of a transplant in a subject comprising administering an effective amount of corticosteroid or antibody therapy to a subject who has had an organ transplant, wherein two or more genes selected from the group consisting of DIP2C, ENOSF1, FBXO21, KCTD6, PDXDC1, REXO2, HLA-E, and RAB31 exhibit differential expression in a biological sample obtained from the subject as compared to a control.

As used throughout, "effective amount" or "therapeutically effective amount" refers to an amount sufficient to effect beneficial or desirable biological and/or clinical results. The effective amount of any of the therapeutic agents described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Other factors that influence dosage can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject also depends upon the judgment of the treating medical practitioner. A therapeutically effective amount is also one in which any toxic or detrimental effects of the composition are outweighed by the therapeutically beneficial effects.

As used herein, administer or administration refers to the act of introducing, injecting or otherwise physically delivering a substance as it exists outside the body into a subject, such as by mucosal, intradermal, intravenous, intratumoral, intramuscular, intrathecal, intracranial, intrarectal, oral, subcutaneous delivery and/or any other method of physical delivery described herein or known in the art.

Any of the therapeutic agents described herein are administered in a number of ways depending on whether local or systemic treatment is desired, and on the area to be treated. The compositions are administered via any of several routes of administration, including orally, parenterally, intrathecally, intracranially, intramucosally, intravenously, intraperitoneally, intraventricularly, intramuscularly, subcutaneously, intracavity or transdermally. Administration can be achieved by, e.g., topical administration, local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; and European Patent Nos. EP488401 and EP 430539. In some methods, the therapeutic agent can be delivered to the subject by way of an implantable device based on, e.g., diffusive, erodible, or convective systems, osmotic pumps, biodegradable implants, electrodiffusion systems, electroosmosis systems, vapor pressure pumps, electrolytic pumps, effervescent pumps, piezoelectric pumps, erosion-based systems, or electromechanical systems. Effective doses for any of the administration methods described herein can be extrapolated from dose-response curves derived from in vitro or animal model test systems.

Any of the therapeutic agents described herein can be formulated as a pharmaceutical composition. In some embodiments, the pharmaceutical composition can further comprise a carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, a pharmaceutical composition comprising a therapeutic agent described herein, can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein the terms "treatment", "treat", or "treating" refers to a method of reducing one or more of the effects of the disease or one or more symptoms of the disease, for example, AR, in the subject. Thus, in the disclosed methods, treatment can refer to a 10%, 20%, 30%, 40%, 50%, 60%, 70%, 80%, 90%, or 100% reduction in the severity of AR. In addition to alleviation or prevention of symptoms, treatment can also slow or stop the progression or worsening of a disease, disorder, or condition and/or the remission of the disease, disorder or condition. For example, a method for treating AR is considered to be a treatment if there is a 10% reduction in one or more symptoms of AR in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease or symptoms of the disease.

An "anti-rejection agent" is any substance administered to a subject for the purpose of preventing or ameliorating a rejection state. Anti-rejection agents include, but are not limited to, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD 154, anti-CD3 antibody, thymoglobin, OKT3, corticosteroid, or a combination thereof.

In some embodiments, the acute rejection relates to acute kidney rejection. It is important to distinguish between acute rejection and drug toxicity. Two of the commonly used drugs prescribed to transplant recipients to prevent rejection, cyclosporine and tacrolimus, can cause kidney toxicity, and this complication is not readily identified solely on the basis of blood concentrations of cyclosporine/tacrolimus. In kidney transplant patients, the clinical importance of distinguishing acute rejection from cyclosporine/tacrolimus toxicity cannot be overemphasized because the treatment approaches are diametrically opposite. In one instance, continued administration of cyclosporine/tacrolimus for rejection is critical whereas, in the other instance, a reduction in dosage or discontinuation of cyclosporine/tacrolimus is indicated to prevent further kidney toxicity. Furthermore, deterioration in kidney function is not always available as a clinical clue to diagnose rejection because many of the kidney transplants suffer from acute (reversible) renal failure in the immediate post-transplantation period due to injury from organ procurement and the ex-vivo preservation procedures involved.

In instances where acute rejection is predicted, a steroid pulse therapy can be started and may include the administration for three to six days of a high dose corticosteroid (e.g., greater than 100 mg or 5-10 mg/kg per kg up to 1 gram). A maintenance regimen of prednisone doses (0.07 to 0.1 mg/kg for children and adults, with a maximum of 5 mg daily) can be used if the patient is not receiving steroid treatment. One or more antibody preparations can be administered for treatment of acute rejection (e.g., acute cellular rejection). Examples of antibody therapy that can be used for treatment of acute rejection include the administration for seven to fourteen days of a lymphocyte-depleting antibody, an anti-thymoglobulin antibody (for example, a polyclonal antibody), an anti-CD52 antibody (for example, alemtuzumab), and an anti-CD3 antibody (e.g., monoclonal antibody OT3). See, for example, Halloran "Immunosuppressive Drugs for Kidney Transplantation," NEJM 2004; 351: 2715-29; and Cooper "Evaluation and Treatment of Acute Rejection in Kidney Allografts," CJASN 15: 430-438 (2020), for additional information regarding treatment of acute rejection.

Another example of a treatment that can be administered, for example for antibody-mediated rejection, is plasmapheresis or plasma exchange. Plasmapheresis is a process in which the fluid part of the blood (i.e., plasma) is removed from blood cells. Typically, the plasma is removed by a device known as a cell separator. The cells are generally returned to the person undergoing treatment, while the plasma, which contains antibodies, is discarded. Other examples, of treatments for antibody mediated acute rejection include intravenous immunoglobulin, and/or anti-CD20 antibodies.

Any of the methods provided herein can further comprise performing a biopsy on transplant tissue from the subject, to determine if antibody-mediated damage has occurred in the subject. The term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

A biopsy can be performed before, concurrently with, or after an assessment of the likelihood of acute rejection of the transplant in the subject. One of skill in the art will appreciate that, in some embodiments, when any of the methods provided herein indicate that acute rejection of the transplant is unlikely, a biopsy is optional, but not necesssary until there is a likelihood of acute rejection based on a gene signature described herein and/or an increase in creatinine levels in the subject.

If the biopsy shows antibody-mediated damage, plasma exchange therapy or intravenous immunoglobulin (Ig) therapy can be administered to the subject. In some embodiments, the intravenous Ig therapy is administered in combination with rituximab. It is understood that, if the subject is likely to develop acute rejection, an effective amount of a corticosteroid or antibody (a lymphocyte-depleting antibody, an anti-thymoglobulin antibody (for example, a polyclonal antibody), an anti-CD52 antibody (for example, alemtuzumab), and an anti-CD3 antibody (e.g., monoclonal antibody OT3), as described above, can be administered to the subject prior to obtaining biopsy results. If the biopsy results show antibody-mediated damage, plasma exchange therapy, intravenous Ig therapy, anti-IL6 therapy (for example, tocilizumab), and/or proteosomal inhibitor therapy (for example, bortezomib or carfilzomib) can be administered to the subject, with or without rituximab.

Kits

Any of the methods provided herein can also be performed by use of kits that are described herein. Provided herein is a kit comprising: (a) agents for detection of two or more genes selected from the group consisting of DIP2C, ENOSF1, FBXO21, KCTD6, PDXDC1, REXO2, HLA-E, and RAB31. In some embodiments, the agents are nucleotide primers or probes. In general, kits can include a detection reagent that is suitable for detecting the presence of one or more RNA of interest. The kits can include a panel of probe and/or primer sets. Such probe and/or primer sets are designed to detect expression of one or more genes and provide information about the rejection of a transplant organ. Probe sets can include probes or primers that are labeled (e.g., fluorescer, quencher, etc.). Unlabeled probes or primers can also be provided in the kits.

The probes and primers are useful for detection of DIP2C, ENOSF1, FBXO21, KCTD6, PDXDC1, REXO2, HLA-E, and RAB31 or a combination thereof. The probe and/or primer sets are targeted at the detection of RNA transcripts and/or structural RNAs that are informative about acute rejection. Probe and/or primer sets may also comprise a large or small number of probes or primers that detect gene transcripts that are not informative about transplant rejection. Such probes and primers are useful as controls and for normalization. Probe and/or primer sets can be provided in the kits as a dry material or dissolved in solution. In some embodiments, probe and/or primer sets can be affixed to a solid substrate to form an array of probes. Probe and/or primer sets can be configured for multiplex PCR. The probes and/or primers can be nucleic acids (e.g., DNA, RNA, chemically modified forms of DNA and RNA), LNA, or PNA, or any other polymeric compound capable of specifically hybridizing with the desired nucleic acid sequences.

The kits can include components for isolating and/or detecting RNA in essentially any sample (e.g., urine, blood, etc.), and a wide variety of reagents and methods are, in view of this specification, known in the art. Hence, the kits can include vials, swabs, needles, syringes, labels, pens, pencils, or combinations thereof.

In some embodiments, commercially available components can also be included in the kits. For example, the kit can include components from QIAGEN, which manufactures a number of components for RNA isolation, including RNEASY, a Total RNA System (involving binding total RNA to a silica-gel-based membrane and spinning the RNA); OLIGOTEX® for isolation of RNA utilizing spherical latex particles; and QIAGEN total RNA kit for In Vitro Transcripts and RNA clean-up.

The kits can include components for fluorescence based real-time detection methods. For example, the kits can include primers for generating cDNA and/or for amplification of mRNA and rRNA. The kits can include components for 5' nuclease assays employ oligonucleotide probes labeled with at least one fluorescer and at least one quencher. Prior to cleavage of the probe, the fluorescer excites the quencher(s) rather than producing a detectable fluorescence emission. The oligonucleotide probe hybridizes to a target oligonucleotide sequence for amplification in PCR. The nuclease activity of the polymerase used to catalyze the amplification of the primers of the target sequence serves to cleave the probe, thereby causing at least one fluorescer to be spatially separated from the quencher so that the signal from the fluorescer is no longer quenched. A change in fluorescence of the fluorescer and/or a change in fluorescence of the quencher due to the oligonucleotide probe being digested can be used to indicate the amplification of the target oligonucleotide sequence. Although some primers and probes are described in the Examples, other suitable primers and probes can be employed. Probes and primers can be designed using techniques available to those of skill in the art.

The kits can also include any of the following components: materials for obtaining a sample, enzymes, buffers, probes, primers for generating cDNA, primers for amplifying RNA or cDNA, materials for labeling nucleic acids, microarrays, one or more microarray reader, competitor nucleic acids, probes and/or primers for a housekeeping gene for normalization, control nucleic acids, and antibodies.

In some embodiments, the agents for detection of two or more genes selected from the group consisting of DIP2C, ENOSF1, FBXO21, KCTD6, PDXDC1, REXO2, HLA-E, and RAB31, are antibodies. For antibody-based kits, the kit may comprise, for example: (1) a first antibody (e.g., attached to a solid support) which binds a polypeptide corresponding to a biomarker disclosed herein; and,optionally (2) a second, different antibody that binds to either the polypeptide or the first antibody and is conjugated to a detectablel label. The antibody-based kits described herein can be used in numerous protein detection methods, for example, immunoassay, immunosorbant assay (ELISA), radioimmunoassay (RIA), immunoblotting, and other techniques available to the skilled artisan.

In further embodiments, kits can include a biological sample collection system. In some embodiments, the biological sample comprises blood. Blood collection systems can include essentially any material useful for obtaining and/or holding a blood sample. Blood collection systems may include, for example, tubing, a beaker, a flask, a vial, a test tube, a container, and/or a lid for a vial, test tube or container (e.g., a plastic container with a snap-on or screw top lid).

In certain embodiments, kits can also include sample test system. A sample test system can include essentially any material that is useful for containing the sample and contacting the sample with the appropriate detection reagents. In some instances, the sample test system can include purification chambers and purification reagents. A sample test system can include, for example, a sample well, which may be part of a multi-well plate, a petri dish, a filter (e.g., paper, nylon, nitrocellulose, PVDF, cellulose, silica, phosphocellulose, or other solid or fibrous surface), a microchannel (which may be part of a microchannel array or a microfluidics device), a small tube such as a thin-walled PCR tube or a 1.5 ml plastic tube, a microarray to which cells or material obtained from the biological sample may be applied, a capillary tube or a flat or curved surface with detection reagent adhered thereto, or a flat or curved surface with material that adheres to proteins or nucleic acids present in the biological sample or in the cells contained in the biological sample.

Kits can include probes that may be affixed to a solid surface to form a customized array. The probes can be any probe that can hybridize to any of the nucleic acids described herein. In some instances, the probes hybridize under medium to high stringency conditions.

Kits may also include a sample preparation system. A sample preparation system comprises, generally, any materials or substances that are useful in preparing the biological sample to be contacted with the detection reagents. For example, a sample preparation system may include materials for separating sample sediments from the fluids, such as centrifuge tube, a microcentrifuge, or a filter (optionally fitted to a tube designed to permit a pressure gradient to be established across the filter). One example of a filter that can be used is a filter within a syringe, such as those available from Zymo Research (see website at zymoresearch.com/columns-plastics/column-filter-assemblies/zrc-gf-filter; e.g., ZRC-GF Filter™). Other components that can be included in the kit include buffers, precipitating agents for precipitating either wanted or unwanted materials, chelators, cell lysis reagents, RNase inhibitors etc.

Collection, presentation and preparation systems can be accomplished in various ways. For example, a filter can be used to separate sample sediments (e.g., cells) from the sample fluids, and the filter may be coated with antibodies suitable for specifically detecting the desired proteins. One of skill in the art would, in view of this specification, readily understand many combinations of components that a kit of the invention may comprise.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Figure 1B:
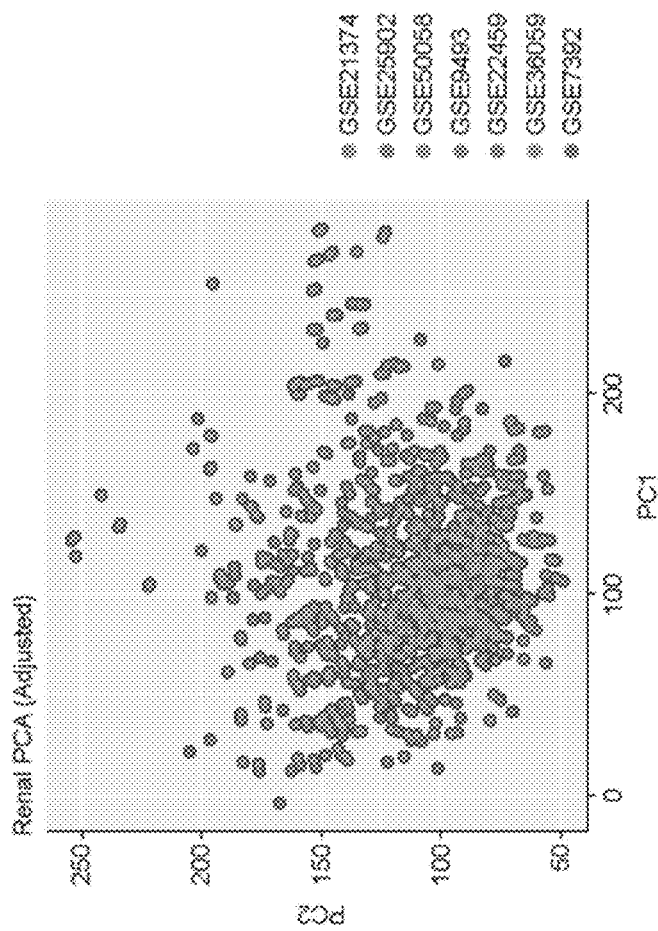
FIGS. 1A-1D are PCA plots of batch effect normalization, according to certain embodiments of this disclosure.
Figure 1A:
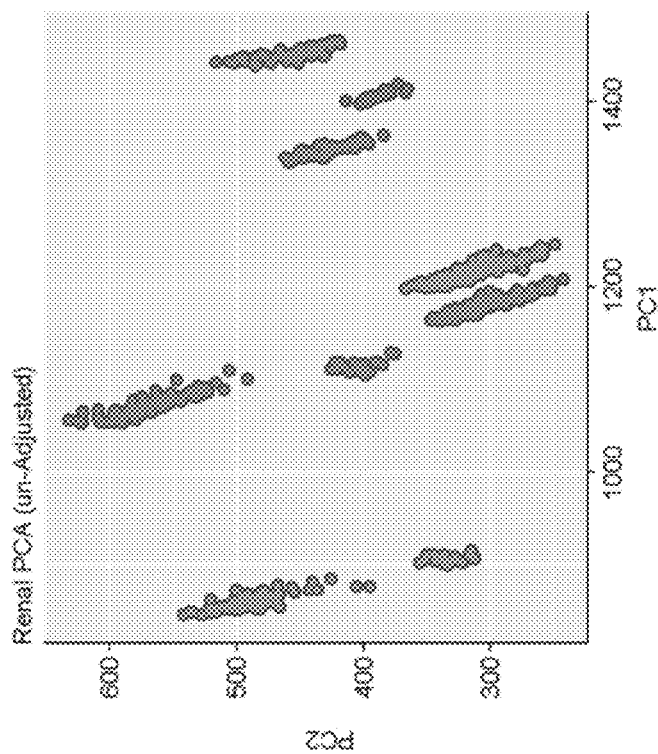
Figure 1D:
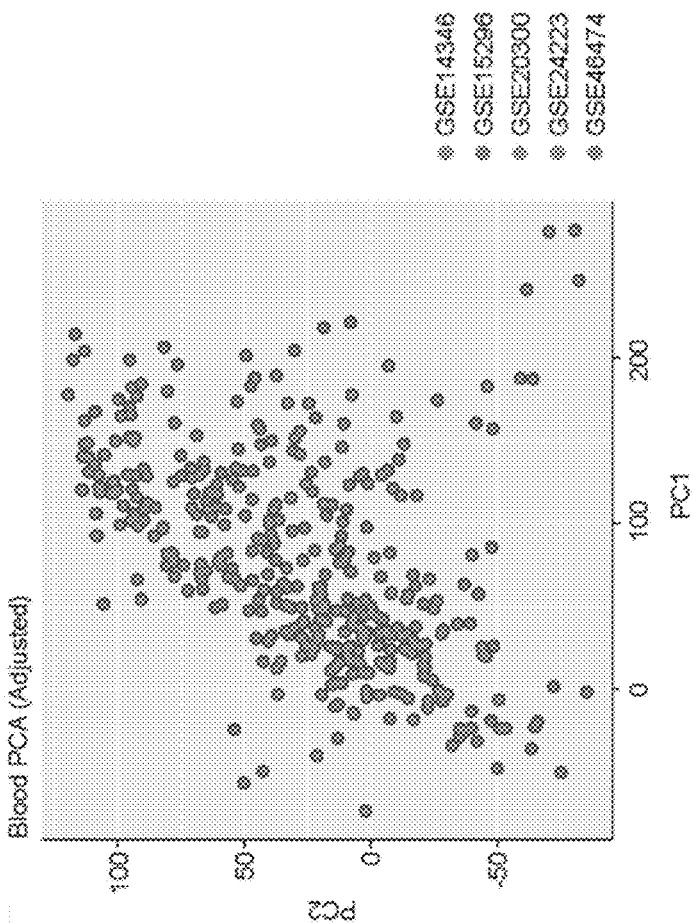
Figure 1C:
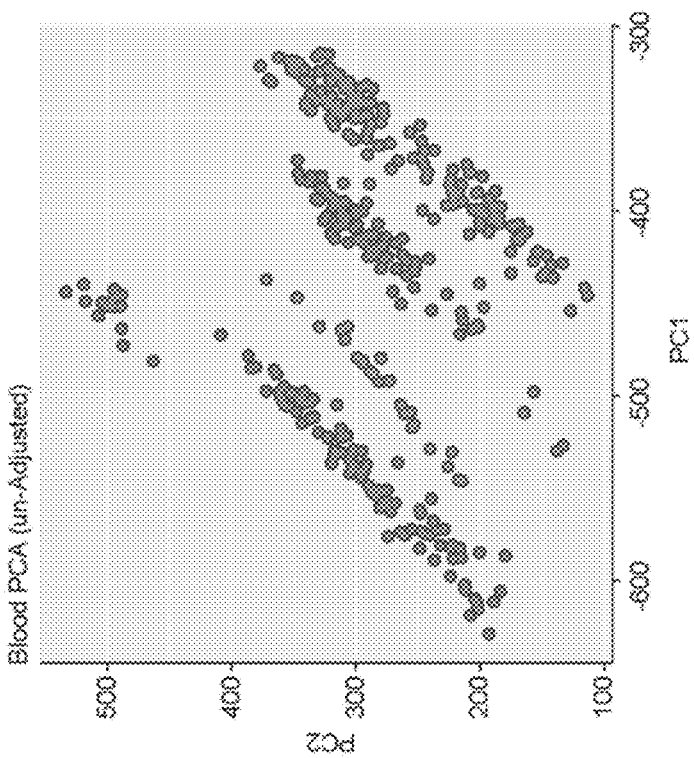

An Age-Independent Gene signature for Monitoring Acute Rejection in Kidney Transplantation
Human Genomic Data Collection A total of 1091 renal gene expression profiles were collected from 7 independent NCBI Gene Expression Omnibus datasets: GSE21374, GSE22459, GSE36059, GSE50058, GSE7392, GSE9493, and GSE25902 (pediatric). In addition, 392 gene expression profiles of peripheral blood cells derived from 5 GEO datasets: GSE14346, GSE15296, GSE24223, GSE46474, and GSE20300 (pediatric) were obtained. Complementing the raw expression data, clinical data from a subset of the samples with AR, including both ABMR and TCMR, stable (STA), borderline rejection, chronic allograft nephropathy (CAN), and interstitial fibrosis/tubular atrophy (IF/TA), were also obtained.
Normalization of Gene Expression Data Gene expression profiles of all datasets were measured using Affymetrix U133A or U133 Plus 2.0 expression array. Each dataset selected for this study contained clinical outcome data and patients' unique IDs were also collected from series matrix files (GEO) to ensure there was no redundancy in the sample set. Raw Affymetrix expression CEL files from each dataset were robust multi-array average normalized independently using Expression Console Version 1.1 (Affymetrix, Santa Clara, CA). All data were filtered to include those probes on the HG-U133A platform. Batch effects were mitigated using surrogate variable analysis (SVA).
Selection and Analysis of Institutional Cohort To further develop a gene signature of early AR, a total of 89 pediatric and adult patients age 1 to 78 transplanted between July 2009 to July 2017 were selected from Duke University's institutional biorepository. They were characterized as AR (39 TCMR, 1 ABMR, and 2 Borderline)—with samples within the 30 days preceding the rejection event—or STA without rejection during the first year after transplantation. Immunosuppression protocols included induction with basiliximab, daclizumab, or rabbit anti-thymocyte globulin, while maintenance regimens included use of tacrolimus, cyclosporine, azathioprine, belatacept, sirolimus, and/or mycophenolate mofetil with or without steroids, including some patients on full steroid withdrawal regimens. Cryopreserved peripheral blood mononuclear cell mRNA expression of genes identified in our microarray data was measured using Applied Biosystems™ TaqMan™ Array Cards and Plates (Thermo Fisher, Waltham, MA). All samples were collected from patients with informed consent and all related procedures were performed with the approval of the Duke Institutional Review Board.
Statistics Analyses Mann-Whitney U Tests were used to identify genes that were differentially expressed between AR and STA groups. Multivariable Cox-regression survival analysis for risk of AR (with the multiple variables being different gene expression values) was also used to identify genes associated with freedom from AR. Shotgun Stochastic Search in Regression (SSS) was used for assigning coefficients to genes that were identified in the previous step. Receiver operating characteristic (ROC) curves were used to assess the diagnostic ability of our signatures in a binary classification system. Gene set enrichment analysis was performed using Enrichr. A gene network was created using STRING v11, Reactome pathway analysis and GO Biological Process analysis were also completed. To assess if the expression of selected 8 genes was truly an independent risk factor of AR, a multivariable logistic regression analysis using generalized linear models (glm) including the clinical variables of race, gender, age, and treatment (use of depletional induction, and/or use of belatacept based maintenance immunosuppression), with a $p<0.05$ considered significant, was used. Statistical analyses were performed using Prism 6 (GraphPad, San Diego, CA), Matlab 2014a (Mathworks, Natick, MA), R 3.4.0 (Project for Statistical Computing Vienna, Austria), STATA 15 (STATA Corp, College Station, TX) or STATISTICA 7 (Dell, Round Rock, TX).
Results
Sample Normalization To capture the heterogeneity of renal allograft rejection, we compiled a large collection of gene expression profile data from either kidney allograft parenchymal biopsy specimens (n=1091) or peripheral blood (n=392) obtained from 12 independent public datasets. Allograft and peripheral blood gene expression profiles showed expression differences among samples obtained from different data sets (FIGS. 1A and 1C). All the gene expression data were combined and batch effects in the combined data were corrected using SVA. (FIGS. 1B and 1D).

Gene Expression Differences Between Adult and Pediatric Samples

Using all patients (pediatric or adult) 45,782, probe sets were utilized to define expression levels in one of three clinical phenotypes—T Cell Mediated Rejection (TCMR), Borderline rejection, or Chronic Allograft Nephropathy (CAN)—as compared to STA patients ($p<0.001$, Mann-Whitney U Test). For each of these phenotypes, we plotted both adult and pediatric samples using the first two principal components of differentially expressed probe sets. We observed that adult and pediatric gene expression was significantly different within the TCMR and CAN clinical groups, but not in the borderline group (FIG. 2A and FIG. 2C).

To define the differences between age groups, expression profiles between adult and pediatric samples were subsequently compared and 25,043 probe sets were identified whose expressions in TCMR and/or CAN were significantly different between adult and pediatric samples ($p<0.001$, Mann-Whitney U Test). After removing these age-group related probe sets, the principal components of TCMR, CAN and borderline were rebuilt using the remaining of 20,739 probe sets. In doing so, a minimization of differences between adult and pediatric samples within the same histologic subtype was observed, indicated by clustering of the points for adult and pediatric samples of the same histologic type (FIGS. 2B and 2D).

Identification of Gene Expression Differences in AR

To develop an age-independent AR signature, AR associated genes were identified in adult samples using the 20,739 probe sets whose expression was not significantly different between adult and pediatric samples. Allograft gene expression differences were compared between samples with AR within 5 years after kidney transplant to samples without any rejection over five years (STA). Differences in gene expression between adult and pediatric TCMR and CAN were also determined. Genes whose expression patterns were significantly associated with AR-free survival using Cox-regression survival analysis were also identified. Because there was limited long-term follow-up for patients with peripheral blood expression data available in public databases, differences between patients with AR and those that were stable over 2 years were determined. As shown in FIG. 3, these four tests, that were independently performed in either kidney tissue or peripheral blood, identified 90 probe sets whose expression were significantly associated with AR in both allograft and peripheral blood samples by either Mann-Whitney U-Test compared to STA ($p<0.001$) or by Cox-regression survival analysis ($p<0.001$) (Table 1). This probe set group (AR90sig) was then utilized to train and test multiple models across sample groups.

TABLE 1

AR associated 90 probe sets

| Affymetrix Probe ID | Symbol | Expression in AR | AR vs. STA (5 year) Renal (MWU test) | AR vs. STA (24 mon) Blood (MWU test) | AR survival (cox-regression) |
|---|---|---|---|---|---|
| 223660_at | ADORA3 | up | 1.65E−07 | 0.00063 | 9.37E−05 |
| 232304_at | AK026714 | up | 1.82E−08 | 1.56E−07 | 0.00016 |
| 222024_s_at | AKAP13 | up | 7.76E−11 | 0.00011 | 9.16E−08 |
| 227438_at | ALPK1 | up | 2.23E−15 | 2.26E−05 | 2.63E−12 |
| 221039_s_at | ASAP1 | up | 4.30E−12 | 0.00048 | 2.90E−06 |
| 228439_at | BATF2 | up | 9.77E−30 | 0.00030 | 1.97E−18 |
| 242268_at | CELF2 | up | 2.25E−32 | 1.66E−05 | 6.39E−18 |
| 1556323_at | CELF2 | up | 3.89E−12 | 3.31E−07 | 5.86E−12 |
| 211316_x_at | CFLAR | up | 7.70E−12 | 1.13E−07 | 3.57E−06 |
| 211862_x_at | CFLAR | up | 4.39E−05 | 5.47E−05 | 0.00027 |
| 222934_s_at | CLEC4E | up | 3.25E−20 | 2.23E−05 | 2.48E−09 |
| 211287_x_at | CSF2RA | up | 2.71E−25 | 0.00029 | 1.04E−17 |
| 823_at | CX3CL1 | up | 9.54E−16 | 0.00024 | 7.59E−07 |
| 220252_x_at | CXorf21 | up | 1.44E−16 | 4.34E−05 | 1.25E−06 |
| 222858_s_at | DAPP1 | up | 4.55E−23 | 6.74E−05 | 8.36E−09 |
| 1556820_a_at | DLEU2 | up | 1.35E−15 | 1.71E−05 | 9.60E−09 |
| 1556821_x_at | DLEU2 | up | 6.54E−21 | 0.00029 | 3.65E−07 |
| 227780_s_at | ECSCR | up | 1.17E−13 | 6.74E−05 | 3.18E−05 |
| 207610_s_at | EMR2 | up | 6.52E−33 | 0.00026 | 9.67E−10 |
| 214605_x_at | GPR1 | up | 1.28E−15 | 0.00067 | 0.00030 |
| 211040_x_at | GTSE1 | up | 2.67E−18 | 2.04E−05 | 0.00024 |
| 1555629_at | HAVCR2 | up | 4.08E−10 | 0.00021 | 1.45E−05 |
| 230529_at | HECA | up | 1.32E−19 | 3.15E−05 | 8.57E−12 |
| 200905_x_at | HLA-E | up | 2.75E−42 | 9.88E−05 | 3.35E−19 |
| 213418_at | HSPA6 | up | 3.37E−27 | 0.00032 | 2.44E−08 |
| 204786_s_at | IFNAR2 | up | 4.04E−15 | 3.32E−06 | 3.36E−08 |
| 209575_at | IL10RB | up | 1.24E−19 | 0.00074 | 2.08E−13 |
| 210184_at | ITGAX | up | 5.36E−20 | 0.00075 | 4.99E−09 |
| 213803_at | KPNB1 | up | 3.53E−05 | 0.00050 | 0.00015 |
| 207857_at | LILRA2 | up | 7.71E−23 | 0.00072 | 3.36E−07 |
| 232623_at | LOC100128751 | up | 5.21E−12 | 0.00011 | 9.53E−06 |
| 215223_s_at | LOC100129518 | up | 2.28E−10 | 0.00021 | 3.77E−05 |
| 227384_s_at | LOC102725188 | up | 8.33E−25 | 0.00020 | 4.35E−06 |
| 230505_at | LOC145474 | up | 4.22E−09 | 3.78E−08 | 0.00067 |
| 1562511_at | LYST | up | 0.00034 | 1.22E−06 | 4.69E−07 |
| 235421_at | MAP3K8 | up | 4.48E−19 | 2.93E−06 | 2.53E−12 |
| 210869_s_at | MCAM | up | 3.15E−19 | 2.81E−05 | 4.91E−06 |
| 200797_s_at | MCL1 | up | 7.38E−24 | 0.00023 | 4.78E−11 |
| 230805_at | MIR142 | up | 8.83E−15 | 0.00095 | 2.89E−10 |
| 229934_at | mir-223 | up | 1.70E−28 | 0.00035 | 3.48E−12 |
| 208082_x_at | MKRN4P | up | 1.51E−15 | 1.55E−06 | 0.00051 |

TABLE 1-continued

AR associated 90 probe sets

| Affymetrix Probe ID | Symbol | Expression in AR | AR vs. STA (5 year) Renal (MWU test) | AR vs. STA (24 mon) Blood (MWU test) | AR survival (cox-regression) |
|---|---|---|---|---|---|
| 227066_at | MOB3C | up | 1.60E−07 | 0.00022 | 1.72E−05 |
| 232724_at | MS4A6A | up | 3.53E−32 | 2.69E−07 | 7.96E−12 |
| 214780_s_at | MYO9B | up | 1.66E−12 | 4.93E−06 | 1.85E−05 |
| 1560706_at | NEDD9 | up | 1.09E−24 | 8.17E−08 | 4.93E−08 |
| 201502_s_at | NFKBIA | up | 6.65E−19 | 3.25E−05 | 2.43E−07 |
| 224303_x_at | NIN | up | 2.82E−07 | 0.00028 | 4.50E−05 |
| 228499_at | PFKFB4 | up | 1.27E−10 | 2.80E−08 | 0.00033 |
| 204958_at | PLK3 | up | 2.49E−11 | 0.00034 | 4.01E−07 |
| 38269_at | PRKD2 | up | 2.55E−12 | 0.00092 | 1.74E−06 |
| 217762_s_at | RAB31 | up | 1.04E−26 | 1.83E−06 | 2.78E−11 |
| 232722_at | RNASET2 | up | 4.75E−20 | 6.12E−06 | 5.33E−08 |
| 233880_at | RNF213 | up | 0.00027 | 0.00061 | 1.79E−08 |
| 1566079_at | RPS16P5 | up | 1.26E−13 | 0.00084 | 3.57E−10 |
| 1559882_at | SAMHD1 | up | 4.82E−26 | 0.00051 | 3.01E−13 |
| 211429_s_at | SERPINA1 | up | 0.00030 | 0.00032 | 3.73E−05 |
| 1559034_at | SIRPB2 | up | 5.93E−10 | 9.85E−09 | 6.66E−10 |
| 237426_at | SP100 | up | 6.68E−19 | 3.60E−06 | 1.78E−10 |
| 208392_x_at | SP110 | up | 5.01E−22 | 0.00064 | 2.75E−12 |
| 209761_s_at | SP110 | up | 4.99E−20 | 4.96E−05 | 1.01E−11 |
| 1556601_a_at | SPAT13 | up | 1.14E−10 | 0.00029 | 8.40E−06 |
| 1556203_a_at | SRGAP2 | up | 3.99E−11 | 2.36E−05 | 0.00062 |
| 236259_at | STK4 | up | 2.86E−07 | 4.41E−05 | 1.76E−09 |
| 207643_s_at | TNFRSF1A | up | 2.73E−07 | 2.46E−07 | 3.29E−05 |
| 213261_at | TRANK1 | up | 3.01E−26 | 0.00068 | 1.70E−12 |
| 203234_at | UPP1 | up | 5.36E−05 | 0.00015 | 3.43E−05 |
| 211800_s_at | USP4 | up | 3.92E−08 | 2.23E−06 | 1.29E−07 |
| 225273_at | WWC3 | up | 8.85E−12 | 4.63E−06 | 5.64E−07 |
| 212860_at | ZDHHC18 | up | 4.98E−09 | 2.16E−06 | 3.40E−05 |
| 215706_x_at | ZYX | up | 4.44E−09 | 0.00093 | 0.00090 |
| 202053_s_at | ALDH3A2 | down | 1.90E−12 | 5.08E−06 | 9.95E−06 |
| 217988_at | CCNB1IP1 | down | 5.62E−12 | 0.00071 | 5.09E−05 |
| 230656_s_at | CIRH1A | down | 1.38E−11 | 4.04E−07 | 0.00077 |
| 223978_s_at | CRLS1 | down | 4.11E−13 | 1.71E−05 | 1.71E−07 |
| 224870_at | DANCR | down | 5.04E−11 | 2.56E−05 | 2.55E−05 |
| 212503_s_at | DIP2C | down | 2.54E−14 | 0.00012 | 0.00022 |
| 204143_s_at | ENOSF1 | down | 4.27E−11 | 9.34E−07 | 0.00020 |
| 212231_at | FBXO21 | down | 2.00E−10 | 1.78E−08 | 0.00026 |
| 220642_x_at | GPR89A | down | 4.09E−16 | 2.30E−05 | 1.11E−05 |
| 211569_s_at | HADH | down | 6.77E−17 | 8.02E−08 | 0.00041 |
| 201035_s_at | HADH | down | 3.97E−10 | 6.51E−05 | 0.00059 |
| 238001_at | KCTD6 | down | 2.92E−09 | 8.74E−05 | 5.80E−05 |
| 212053_at | LOC102724985 | down | 9.53E−15 | 3.71E−08 | 0.00052 |
| 223177_at | NT5DC1 | down | 1.79E−13 | 3.83E−06 | 0.00092 |
| 203335_at | PHYH | down | 2.92E−15 | 1.04E−05 | 0.00019 |
| 218194_at | REXO2 | down | 1.03E−12 | 0.00014 | 0.00079 |
| 1553118_at | THEM4 | down | 7.54E−12 | 0.00081 | 0.00055 |
| 223105_s_at | TMEM14B | down | 1.18E−05 | 2.58E−05 | 0.00017 |
| 223282_at | TSHZ1 | down | 1.24E−11 | 4.30E−08 | 0.00082 |
| 227907_at | TUBGCP4 | down | 1.23E−09 | 0.00018 | 5.20E−05 |

Biologic Validity of Candidate Genes

These genes were plotted on a heatmap to define their expression between groups which confirmed good segregation between AR and STA groups (See FIG. 4A, Shaw et al. Theranostics 10(15): 6977-6986 (2020)). From the 90 AR associated probe sets, we identified 76 genes whose expressions were significantly changed in AR. To determine the biologic basis of these 76 genes, gene set enrichment analysis was performed and the gene signature was found to be significantly associated with immune system and interferon signaling (Table 2; (See FIG. 4A, Shaw et al. Theranostics 10(15): 6977-6986 (2020)).

TABLE 2

Enrichr gene set enrichment analysis of AR up-regulated gene from AR90

| | Combined Score | Genes from AR90 |
|---|---|---|
| Reactome 2016 Terms | | |
| Cytokine Signaling in Immune system_Homo sapiens_R-HSA-1280215 | 29.21 | IFNAR2, SP100, IL10RB, PELI1, MAP3K8, SAMHD1, CSF2RA, KPNB1, TNFRSF1A, HAVCR2, HLA-E |

TABLE 2-continued

Enrichr gene set enrichment analysis of AR up-regulated gene from AR90

| | Combined Score | Genes from AR90 |
|---|---|---|
| Immune System_Homo sapiens_R-HSA-168256 | 26.21 | IFNAR2, SP100, IL10RB, DAPP1, MYO9B, SAMHD1, LILRA2, CSF2RA, TNFRSF1A, HLA-E, NFKBIA, RNF213, PELI1, MAP3K8, CLEC4E, KPNB1, HAVCR2 |
| Interferon Signaling_Homo sapiens_R-HSA-913531 | 15.97 | IFNAR2, SP100, SAMHD1, KPNB1, HLA-E |
| Death Receptor Signalling_Homo sapiens_R-HSA-73887 | 15.27 | USP4, CFLAR, TNFRSF1A |
| TNFR1-induced proapoptotic signaling_Homo sapiens_R-HSA-5357786 | 12.55 | USP4, TNFRSF1A |
| Interferon alpha/beta signaling_Homo sapiens_R-HSA-909733 | 11.84 | IFNAR2, SAMHD1, HLA-E |
| MyD88 cascade initiated on plasma membrane_Homo sapiens_R-HSA-975871 | 11.82 | NFKBIA, PELI1, MAP3K8 |
| Toll Like Receptor 10 (TLR10) Cascade_Homo sapiens_R-HSA-168142 | 11.78 | NFKBIA, PELI1, MAP3K8 |
| Toll Like Receptor 5 (TLR5) Cascade_Homo sapiens_R-HSA-168176 | 11.73 | NFKBIA, PELI1, MAP3K8 |
| TRAF6 mediated induction of NFkB and MAP kinases upon TLR7/8 or 9 activation_Homo sapiens_R-HSA-975138 | 11.72 | NFKBIA, PELI1, MAP3K8 |
| MyD88 dependent cascade initiated on endosome_Homo sapiens_R-HSA-975155 | 11.66 | NFKBIA, PELI1, MAP3K8 |
| Toll Like Receptor 7/8 (TLR7/8) Cascade_Homo sapiens_R-HSA-168181 | 11.62 | NFKBIA, PELI1, MAP3K8 |
| Toll Like Receptor 9 (TLR9) Cascade_Homo sapiens_R-HSA-168138 | 11.58 | NFKBIA, PELI1, MAP3K8 |
| MyD88:Mal cascade initiated on plasma membrane_Homo sapiens_R-HSA-166058 | 10.62 | NFKBIA, PELI1, MAP3K8 |
| Signaling by Interleukins_Homo sapiens_R-HSA-449147 | 10.60 | IL10RB, PELI1, MAP3K8, CSF2RA, HAVCR2 |
| Toll Like Receptor 2 (TLR2) Cascade_Homo sapiens_R-HSA-181438 | 10.54 | NFKBIA, PELI1, MAP3K8 |
| Toll Like Receptor TLR1:TLR2 Cascade_Homo sapiens_R-HSA-168179 | 10.51 | NFKBIA, PELI1, MAP3K8 |
| Toll Like Receptor TLR6:TLR2 Cascade_Homo sapiens_R-HSA-168188 | 10.44 | NFKBIA, PELI1, MAP3K8 |
| GO Biological Process 2017 Terms | | |
| type I interferon signaling pathway (GO:0060337) | 31.72 | IFNAR2, SP100, SAMHD1, HLA-E |
| neutrophil degranulation (GO:0043312) | 25.78 | RAB31, SERPINA1, RNASET2, HSPA6, ITGAX, KPNB1 |
| defense response to protozoan (GO:0042832) | 22.46 | BATF2, LYST |
| leukocyte chemotaxis (GO:0030595) | 22.45 | LYST, CX3CL1 |
| positive regulation of inflammatory response (GO:0050729) | 20.73 | NFKBIA, CX3CL1, TNFRSF1A |
| positive regulation of I-kappaB kinase/NF-kappaB signaling (GO:0043123) | 19.82 | AKAP13, PELI1, CFLAR, TNFRSF1A |
| apoptotic process (GO:0006915) | 19.17 | NFKBIA, PLK3, CFLAR, STK4 |
| regulation of extrinsic apoptotic signaling pathway via death domain receptors (GO: 1902041) | 17.83 | SP100, CFLAR |
| positive regulation of interleukin-4 production (GO:0032753) | 17.33 | HAVCR2, HLA-E |
| filopodium assembly (GO:0046847) | 16.80 | SPATAI3, SRGAP2 |
| defense response to virus (GO:0051607) | 16.80 | IFNAR2, SAMHD1, LYST |

TABLE 2-continued

Enrichr gene set enrichment analysis of AR up-regulated gene from AR90

| | Combined Score | Genes from AR90 |
|---|---|---|
| positive regulation of NF-kappaB transcription factor activity (GO:0051092) | 14.49 | NFKBIA, PRKD2, CFLAR |
| negative regulation of apoptotic process (GO:0043066) | 14.37 | NFKBIA, PLK3, CFLAR, MCL1 |
| negative regulation of DNA binding (GO:0043392) | 13.28 | NFKBIA, SP100 |
| regulation of heart contraction (GO:0008016) | 13.07 | ADORA3, CELF2 |
| regulation of small GTPase mediated signal transduction (GO:0051056) | 12.91 | AKAP13, MYO9B, SRGAP2 |
| I-kappaB kinase/NF-kappaB signaling (GO:0007249) | 10.06 | NFKBIA, TNFRSF1A |
| KEGG 2019 Human Terms | | |
| TNF signaling pathway | 860.63 | NFKBIA, MAP3K8, CFLAR, CX3CL1, TNFRSF1A |
| Legionellosis | 349.55 | NFKBIA, HSPA6 |
| Toxoplasmosis | 292.20 | NFKBIA, IL10RB, HSPA6, TNFRSF1A |
| Toll-like receptor signaling pathway | 248.19 | IFNAR2, NFKBIA, MAP3K8 |
| Amyotrophic lateral sclerosis (ALS) | 234.98 | TNFRSF1A |
| Human cytomegalovirus infection | 227.09 | NFKBIA, AKAP13, IL10RB, CX3CL1, TNFRSF1A, HLA-E |
| Osteoclast differentiation | 208.76 | IFNAR2, NFKBIA, LILRA2, TNFRSF1A |
| NF-kappa B signaling pathway | 174.63 | NFKBIA, CFLAR, TNFRSF1A |
| Graft-versus-host disease | 124.12 | HLA-E |
| Autoimmune thyroid disease | 122.23 | HLA-E |
| Complement and coagulation cascades | 118.73 | SERPINA1, ITGAX |
| RIG-I-like receptor signaling pathway | 104.87 | NFKBIA |
| Necroptosis | 101.20 | IFNAR2, CFLAR, TNFRSF1A |
| Allograft rejection | 99.26 | HLA-E |
| Fructose and mannose metabolism | 79.48 | PFKFB4 |
| Chagas disease (American trypanosomiasis) | 74.84 | NFKBIA, CFLAR, TNFRSF1A |
| Cytosolic DNA-sensing pathway | 71.03 | NFKBIA |
| C-type lectin receptor signaling pathway | 67.63 | NFKBIA, PLK3, CLEC4E |
| Natural killer cell mediated cytotoxicity | 64.90 | IFNAR2, HLA-E |
| Antigen processing and presentation | 64.16 | HSPA6, HLA-E |
| Sphingolipid signaling pathway | 62.77 | ADORA3, TNFRSF1A |
| Shigellosis | 62.35 | NFKBIA |
| Small cell lung cancer | 61.00 | NFKBIA |
| T cell receptor signaling pathway | 49.01 | NFKBIA, MAP3K8 |
| Adipocytokine signaling pathway | 47.81 | NFKBIA, TNFRSF1A |
| B cell receptor signaling pathway | 45.05 | NFKBIA, DAPP1 |
| Chronic myeloid leukemia | 41.08 | NFKBIA |
| Viral myocarditis | 32.66 | HLA-E |
| Apoptosis | 32.28 | NFKBIA, CFLAR, TNFRSF1A, MCL1 |
| Pyrimidine metabolism | 31.50 | UPP1 |
| Th17 cell differentiation | 31.48 | NFKBIA |
| Type I diabetes mellitus | 30.04 | HLA-E |
| Measles | 29.58 | IFNAR2, NFKBIA, HSPA6 |
| Tuberculosis | 27.24 | PLK3, IL10RB, ITGAX, CLEC4E, TNFRSF1A |
| IL-17 signaling pathway | 22.49 | NFKBIA |
| Th1 and Th2 cell differentiation | 19.51 | NFKBIA |
| Non-small cell lung cancer | 17.33 | STK4 |
| Insulin resistance | 15.55 | NFKBIA, TNFRSF1A |
| Influenza A | 15.48 | IFNAR2, NFKBIA, HSPA6, TNFRSF1A |
| Fc gamma R-mediated phagocytosis | 13.31 | ASAP1 |
| Longevity regulating pathway | 13.28 | HSPA6, SOD2 |
| JAK-STAT signaling pathway | 11.25 | IFNAR2, IL10RB, CSF2RA, MCL1 |
| Parathyroid hormone synthesis, secretion and action | 11.15 | AKAP13 |
| Human immunodeficiency virus 1 infection | 11.07 | NFKBIA, SAMHD1, TNFRSF1A, HLA-E |

TABLE 2-continued

Enrichr gene set enrichment analysis of AR up-regulated gene from AR90

| | Combined Score | Genes from AR90 |
|---|---|---|
| Hepatitis C | 10.88 | IFNAR2, NFKBIA, CFLAR, TNFRSF1A |
| Peroxisome | 10.60 | SOD2 |
| FoxO signaling pathway | 10.44 | PLK3, STK4, SOD2 |
| Leishmaniasis | 10.38 | NFKBIA |

Furthermore, a novel gene network using STRING v11, that included the pathways noted above as well as others (FIG. 6), was defined.

Developing a 90-Probe Set Identifier of Acute Rejection

Using SSS modeling, a 90-probe set predictor, using a training set of 298 adult kidney allograft samples, was created and validated in independent sets of adult (n=316) and pediatric (n=33) samples (FIG. 4A).

All three analyses showed high sensitivity and specificity for the signature to identify AR. Because the kidney tissue and peripheral blood samples were normalized differently (as they are from different tissue compartments with different background variability), renal tissue and peripheral blood models were built and validated independently. Therefore, a separate signature in adult peripheral blood (n=196) samples was created and validated using an independent set of pediatric peripheral blood (n=24) samples (FIG. 4B). Though the two signatures contained the same genes, SSS was run on allograft and peripheral blood samples independently, yielding different coefficients. Of note, the 90-probe set signature performed well on ROC analysis with a minimum area under the curve (AUC) of 0.79 when considering both analyses.

Furthermore, a cut-off gene expression level at maximum sensitivity and specificity in training data to define high vs. low risk of AR was created and this cut-off was applied to validation sets. The positive predictive value (PPV) in the adult renal validation set was 30%, while the negative predictive value (NPV) was at 98%. The model also successfully delineated AR event-free survival between high vs. low risk cases (p<0.0001, Mantel-Cox test) (FIG. 4C). In peripheral blood, a similar analysis was performed which showed a PPV of 85% and NPV of 70% in the pediatric validation dataset (Table 3).

Creating an Age-Independent 8 Gene Signature of Early Onset AR

In order to monitor early AR events, blood samples from AR (n=42) and STA (n=47) patients, available from our institutional biorepository, were obtained. All samples were from patients monitored for the first year post transplant, with STA defined as no rejection during that time. All AR samples were obtained within 30 days prior to an AR event. Patients were excluded from the AR group if they experienced another event (e.g. an infection) up to 14 days after the rejection event. Patients in the two groups were demographically similar except with regards to immunosuppressive management. More patients in the AR group received basiliximab induction and/or belatacept maintenance, while patients in STA group received tacrolimus (Table 4).

TABLE 4

Demographics of institutional cohort

| Characteristic-n (%) | Rejection- 42 (39) | Stable- 47 (44) | P-Value |
|---|---|---|---|
| Age-mean(SD) | 41 (17) | 39 (21) | 0.63 |
| Pediatric-n(%) | 8 (19) | 15 (32) | 0.23 |
| Female Sex-n(%) | 17 (41) | 20 (43) | 1.0 |
| Race-n(%) | | | 0.054 |
| African American | 24 (57) | 13 (28) | |
| Asian | 0 (0) | 2 (4) | |
| White | 16 (38) | 30 (64) | |
| Other | 2 (5) | 2 (4) | |
| Transplant Type-n(%) | | | 0.162 |
| Living Donor | 13 (38) | 8 (25) | |
| Deceased donor | 21 (62) | 24 (75) | |

TABLE 3

ROC and likelihood ratios

| | | ROC (AUC) | Positive Predictive Value PPV (95% CI) | Negative Predictive Value NPV (95% CI) |
|---|---|---|---|---|
| Renal AR90 predictor | Adult Training | 0.99 | 94% (87.67%-97.19%) | 94.95% (91.25%-97.14%) |
| | Adult Validation | 0.91 | 31.35% (31.22%-43.92%) | 98.28% (95.78%-99.31%) |
| | Pediatric Validation | 1 | 100% | 100% |
| Blood AR90 predictor | Adult Training | 0.99 | 94.59% (89.11%-97.40%) | 94.83% (85.69%-98.25%) |
| | Pediatric Validation | 0.79 | 85.71% (63.26%-95.43%) | 70% (44.44%-87.19%) |
| Early AR8 predictor | Duke dataset | 0.71 | 70.59% (57%-81.29%) | 74.47% (64.17%-82.61%) |
| | Public dataset | 0.77 | 66.67% (16%-95.45%) | 83.18% (81.01-85.14%) |

TABLE 4-continued

Demographics of institutional cohort

| Characteristic-n (%) | Rejection-42 (39) | Stable-47 (44) | P-Value |
|---|---|---|---|
| Induction Type-n(%) | | | |
| Basiliximab | 14 (33) | 7 (15) | 0.049 |
| Anti-Thymocyte Globulin | 9 (21) | 9 (19) | 0.79 |
| No Induction | 19 (46) | 31 (66) | 0.058 |
| Maintenance Therapy-n(%) | | | |
| Prednisone | 40 (95) | 39 (82) | 0.095 |
| Tacrolimus | 35 (83) | 46 (98) | 0.024 |
| Mycophenolate Mofetil | 42 (100) | 46 (98) | 1.0 |
| Cyclosporine | 0 (0) | 1 (2) | 1.0 |
| Azathioprine | 1 (2) | 2 (4) | 1.0 |
| Sirolimus | 2 (5) | 4 (9) | 0.67 |
| Belatacept | 7 (17) | 0 (0) | 0.004 |

After removing genes located on the X chromosome, as there are differential numbers between women and men, and probe sets related to microRNA, a total of 76 genes corresponding to the original 90 probe set were interrogated by Real Time-Polymerase Chain Reaction (RT-PCR). 8 genes (DIP2C, ENOSF1, FBXO21, KCTD6, PDXDC1, REXO2, HLA-E, and RAB31) were found to be differentially expressed in AR and this signature retained its significance after adjusting for multiple clinical variables, including as race, gender, age, and treatment (use of depletional induction, and/or use of belatacept based maintenance immunosuppression) (Table 5).

TABLE 5

Early AR (1 year) associated 8 genes

| Gene | Unadjusted P-Vale | Adjusted* P-Value | Adjusted* OR (2.5%-97.5% CI) |
|---|---|---|---|
| HLA-E | 0.01255 | 0.03680 | 5.09 (1.24-26.56) |
| RAB31 | 0.00557 | 0.00641 | 3.83 (1.58-11.21) |
| REXO2 | 0.02985 | 0.02090 | 0.51 (0.28-0.87) |
| ENOSF1 | 0.00150 | 0.00064 | 0.50 (0.32-0.72) |
| DIP2C | 0.01278 | 0.00253 | 0.50 (0.30-0.75) |
| KCTD6 | 0.00093 | 0.00192 | 0.40 (0.21-0.68) |
| PDXDC1 | 0.00117 | 0.00079 | 0.37 (0.19-0.63) |
| FBXO21 | 0.00392 | 0.00089 | 0.25 (0.10-0.53) |

*Adjusted values based on multivariable generalized linear model including age, race, gender, use of depletional induction immunosuppression, and use of belatacept based maintenance immunosuppression Using these 8 genes, PCA was again employed to create a model to identify AR. The ROC curve AUC was found to be 0.71 (FIG. 5A).

Finally, this signature of early AR events that was validated in 110 Duke patients (adult and pediatric) was applied to patients in the public dataset using the microarray data in the GEO that was initially queried. Utilizing the PCA created with the institutional cohort, the 8 gene signature was applied. This yielded an AUC of 0.77 in this cohort (FIG. 5B). The NPV and PPV for the institutional dataset were 74.5% and 70.6% respectively. The NPV and PPV for the validation in the public dataset were 83.2% and 66.7% respectively.

In the present study, a gene signature for AR, using both publicly available kidney allograft parenchymal and peripheral blood gene expression data and peripheral blood biospecimens from our institutional biorepository, was created and validated. After creation of a 90-probe-set signature targeting 76 genes based on microarray data, validation of this allograft biopsy signature showed a very high AUC in adult (0.91) and pediatric (1.00) datasets. In peripheral blood, validation AUC in a pediatric cohort was moderate at 0.79. Examination of this institutional cohort identified a subset of 8 differentially expressed genes. This 8 gene signature was confirmed in a cohort of 110 patients from public databases and again demonstrated a reasonable AUC for identifying early acute rejection (0.77). Overall, this analysis demonstrates an effective method for biomarker discovery utilizing a combination of publicly available data and single center resources. Provided herein is an age-independent signature of AR that performs well in a peripheral blood assay despite diverse and non-standardized immunosuppressive regimens. Though there is considerable excitement regarding the ability of peripheral blood-based biomarkers to advance the diagnosis and treatment of disease, there have been great challenges in moving from the research setting into clinical care. Additionally, all biomarker research has been plagued by a lack of reproducibility.

Given these limitations, novel methods of merging available data in all relevant combinations to imbue richness in analysis is needed. As shown herein, building a base set of differentially expressed genes from both kidney allograft and peripheral blood gene expression data, allowed for the detection of a very broad set of relevant genes involved in the AR response. Prior studies have failed to find a strict correlation between genes active in the graft and peripheral blood at the time of AR. The studies described herein, however, show that it can be effective to utilize genes differentially expressed in either compartment in the determination of molecular perturbations in both.

Mechanistically, the 90-probe set signature contained 76 genes, many of which are important in immune regulation. One central pathway in the signature is that of Tumor Necrosis Factor-α (TNF-α) and the nuclear factor K-light-chain-enhancer of activated B-Cells (NFKB) signaling. This multifaceted pathway is important in pro-inflammatory and apoptotic mechanisms depending on the context. The signature of AR was also associated with inflammatory TNF signaling as MCL1, a known anti-apoptotic factor important in both polymorphonuclear cell and lymphocyte survival. Additionally, there was upregulation of USP4 and NFKBIA, both of which downregulate TNF-α based NFKB signaling. These mediators may attenuate overall TNF-α signaling to prevent exhaustion of activated cells. Additionally, some reports in transplantation have noted certain polymorphisms of NFKBI are associated with AR, suggesting that some forms of this gene product may enhance pro-inflammatory signaling. NFKBI is necessary for TNF signaling as it holds NFKB in the cytoplasm prior to nuclear translocation and activation of its inflammatory transcriptional program.

Consistent with an initial analysis, upregulation of Human Leukocyte Antigen (HLA)-E, in the subset of 8 genes that were associated with AR arising within 1-year post-transplant, was observed. HLA-E interacts with CD159c/NKG2C, which activates NK cells. This HLA-E mediated signaling has been shown to occur in the kidney during AR. Interestingly, HLA-E upregulation has been noted as a "Universal" rejection feature of AR, regardless of histologic type. Additionally, two other Class-I HLA presentation associated transcripts, KCTD6 and FBXO21, are implicated in the gene signature. Both are involved in ubiquitination and antigen processing, suggesting a contribution of increased antigen presentation as a contributing factor to rejection.

As shown herein, an age-independent peripheral signature of acute rejection was identified that is effective in the setting of diverse, non-standardized immunosuppressive therapies. This signature provides a less invasive method of identifying acute rejection, to maximize graft survival and minimize patient morbidity.

TABLE 6

Probe Sequences

| Context Sequence | SEQ ID NO: | Gene Symbol | Gene Name |
|---|---|---|---|
| CCATTGGAGGGCAAGTCTGGTGCCA | 17 | 18S | Eukaryotic 18S rRNA |
| GGAACACCTTCCCGCTGCTGGCTCC | 18 | ADGRE2 | adhesion G protein-coupled receptor E2 |
| GTTCAAGACGGCTAAGTCCTTGTTT | 19 | ADORA3 | adenosine A3 receptor |
| TGAAAGAGGTTCAAGCAGTTCTTCT | 20 | AKAP13 | A-kinase anchoring protein 13 |
| CTCAGTATTTAGACCAGGATCTCTA | 21 | ALDH3A2 | aldehyde dehydrogenase 3 family member A2 |
| CGGATAAAAAGGGCCTCTCCACGTC | 22 | ALPK1 | alpha kinase 1 |
| GTGGTGGATTGGCCACATCGAAGGA | 23 | ASAP1 | ArfGAP with SH3 domain, ankyrin repeat and PH domain 1 |
| CTGCACCAGCAGCACGAGTCTCTGG | 24 | BATF2 | basic leucine zipper ATF-like transcription factor 2 |
| CAATCTCCAGAGCCATCGCCTGTGA | 25 | BAZ1A | bromodomain adjacent to zinc finger domain 1A |
| TGGACATATCAGGTACATCAGGAAC | 26 | CCNB1IP1 | cyclin B1 interacting protein 1 |
| TCTGGCGCTCCTGCAGCAGGCCACC | 27 | CELF2 | CUGBP, Elav-like family member 2 |
| CAAGATAAGCAAGGAGAAGAGTTTC | 28 | CFLAR | CASP8 and FADD like apoptosis regulator |
| GCAACAGGCAAGAACGGAGATACTC | 29 | Cirh1a | cirrhosis, autosomal recessive 1A (human) |
| CAGTATGCTGTCTTGCCGACGGGGC | 30 | CKLF | chemokine-like factor |
| GACAAAGTCTCTGAGCTTCTGGGAT | 31 | CLEC4E | C-type lectin domain family 4 member E |
| ACAGATTTGTTGGATGGATTTATTG | 32 | CRLS1 | cardiolipin synthase 1 |
| GCTGGCTGGACAGCACCACGGTGTG | 33 | CX3CL1 | C-X3-C motif chemokine ligand 1 |
| GAGTTGCGCGGGCTGACGCGCCACT | 34 | DANCR | differentiation antagonizing non-protein coding RNA |
| CTGGTCAAGACCTGGAAAACAAGAT | 35 | DAPP1 | dual adaptor of phosphotyrosine and 3-phosphoinositides 1 |
| AGAACACCTTTGAGGTGTTTCCCAT | 36 | DIP2C | disco interacting protein 2 homolog C |
| TAAGAGGATATGAAAGGTGTAAATT | 37 | DLEU2 | deleted in lymphocytic leukemia 2 (non-protein coding) |
| TGGTACCCCAGGCGCAGGTGTCCCC | 38 | ECSCR | endothelial cell surface expressed chemotaxis and apoptosis regulator |
| GCTGCGGCTGCAGAAGGCCAGGCCC | 39 | EHBP1L1 | EH domain binding protein 1 like 1 |
| TACTCACACACCCTATTTTCAAGGC | 40 | ENOSF1 | enolase superfamily member 1 |
| CGTATCTTGAAGGTGCTGTATATAT | 41 | FBXO21 | F-box protein 21 |
| TCACGCACTCTGATGGTGCTGGAAA | 42 | FYB | FYN binding protein |
| CGCTGCCAAGGCTGTGGGCAAGGTC | 43 | GAPDH | glyceraldehyde-3-phosphate dehydrogenase |
| AGTCCACACAGGCTGGAGACGACCT | 44 | GAS7 | growth arrest specific 7 |
| CAACCACTTCAGCTTGACCCTCAAC | 45 | GPI | glucose-6-phosphate isomerase |

TABLE 6-continued

Probe Sequences

| Context Sequence | SEQ ID NO: | Gene Symbol | Gene Name |
|---|---|---|---|
| AGTAAGAAGTTCCAAGCTCGCTTCC | 46 | GPR1 | G protein-coupled receptor 1 |
| GGGCTGCGGAGAAGCCCAAGAAAGA | 47 | GTSE1 | G2 and S-phase expressed 1 |
| GTTTGCTGCTGAACATACAATCTTT | 48 | HADH | hydroxyacyl-CoA dehydrogenase |
| CTACTTACAAGGTCCTCAGAAGTGG | 49 | HAVCR2 | hepatitis A virus cellular receptor 2 |
| ACCTTCAAGGGAGACTCATGCATCT | 50 | HECA | hdc homolog, cell cycle regulator |
| GCTTCACCTGGAGCCCCCAAAGACA | 51 | HLA-E | major histocompatibility complex, class I, E |
| TGGTCAAGGTCGCAAGCTTGCTGGT | 52 | HPRT1 | hypoxanthine phosphoribosyltransferase 1 |
| CCGCGCCACCCGGCTGAGTCAGCCC | 53 | HSPA6 | heat shock protein family A (Hsp70) member 6 |
| TTCATATGATTCGCCTGATTACACA | 54 | IFNAR2 | interferon alpha and beta receptor subunit 2 |
| AACAACCCATGACGAAACGGTCCCC | 55 | IL10RB | interleukin 10 receptor subunit beta |
| TGTCCAGGCAGGAGTGCCCAAGACA | 56 | ITGAX | integrin subunit alpha X |
| ATCTACCCTTAACAGAGCTTTTCTT | 57 | KCTD6 | potassium channel tetramerization domain containing 6 |
| GGTGGAAGTGTTGGGTGGTGAATTC | 58 | KPNB1 | karyopherin subunit beta 1 |
| TGGTGGTGACAGGAGCCTACAGCAA | 59 | LILRA2 | leukocyte immunoglobulin like receptor A2 |
| TGCTGGCTACAACAGATTTGTTCTG | 60 | LILRB1 | leukocyte immunoglobulin like receptor B1 |
| AGGGCCGCCCTCCACACCTGGTCTG | 61 | LILRB3; LILRA6 | leukocyte immunoglobulin like receptor B3, leukocyte immunoglobulin like receptor A6 |
| TTCTCTTCAACGGAGCTAAGGTTGG | 62 | LYST | lysosomal trafficking regulator |
| CCTCCTACCTGTACATAATCCACAA | 63 | MAP3K8 | mitogen-activated protein kinase kinase kinase 8 |
| GGAGAAGAACCGGGTCCACATTCAG | 64 | MCAM | melanoma cell adhesion molecule |
| TAAACAAAGAGGCTGGGATGGGTTT | 65 | MCL1 | BCL2 family apoptosis regulator |
| TAACAGCACTGGAGGGTGTAGTGTT | 66 | MIR142 | microRNA 142 |
| TTTCCCACGCGTGTTGGAGTTCCCT | 67 | MOB3C | MOB kinase activator 3C |
| AACCAAGCTTTTGGTGCATAGCAGC | 68 | MS4A6A | membrane spanning 4-domains A6A |
| GAGGAGAGCAACTTCCCCCACGCCA | 69 | MYO9B | myosin IXB |
| GAACATCATCAGCTGAGCCAGTTCC | 70 | NEDD9 | neural precursor cell expressed, developmentally down-regulated 9 |
| TGTCAATGCTCAGGAGCCCTGTAAT | 71 | NFKBIA | NFKB inhibitor alpha |
| GGCTTCTCAGGAAAAGGTTCAGAAT | 72 | NIN | ninein |
| TTTCCGGACACTCGAGAATGATGAG | 73 | NT5DC1 | 5'-nucleotidase domain containing 1 |
| CTACAACGTGGATCAGCACCGGAAG | 74 | ODF3B | outer dense fiber of sperm tails 3B |
| TTGGAGATATATAAGGCTTTCAGTT | 75 | PARP9 | poly(ADP-ribose) polymerase family member 9 |
| CCAGGCTCAGATCCGGTGTTTAAAG | 76 | PDXDC1 | pyridoxal dependent decarboxylase domain containing 1 |
| GAGGAAAAATGGTGGAAATTGAAAC | 77 | PELI1 | pellino E3 ubiquitin protein ligase 1 |

TABLE 6-continued

Probe Sequences

| Context Sequence | SEQ ID NO: | Gene Symbol | Gene Name |
| --- | --- | --- | --- |
| GGGGGACATGTGGCGGTTTTTGATG | 78 | PFKFB4 | 6-phosphofructo-2-kinase/fructose-2,6-biphosphatase 4 |
| AGCCCACAGCTCCATGGTAGGAGTC | 79 | PGK1 | phosphoglycerate kinase 1 |
| TTCAACGCTTTCGGAATGAGTTTGA | 80 | PHYH | phytanoyl-CoA 2-hydroxylase |
| GAGGAAGAAGACCATCTGTGGCACC | 81 | PLK3 | polo like kinase 3 |
| TTCCTCATCACCCAGATCCTGGTGG | 82 | PRKD2 | protein kinase D2 |
| GGCGGCCGCGGGATCTCCCAGCCAT | 83 | PROSC | proline synthetase cotranscribed homolog (bacterial) |
| GAATCAGCCGCCAGATCCCACCCTT | 84 | RAB31 | RAB31, member RAS oncogene family |
| GAGATCGATGAGCATGCCCCCGGAG | 85 | RAB40B | RAB40B, member RAS oncogene family |
| GCACTCCCAAGATTGATAATTAGGA | 86 | RBPJ | recombination signal binding protein for immunoglobulin kappa J region |
| GGCTGCTTCTCATAGGGCACTTGAT | 87 | REXO2 | RNA exonuclease 2 |
| AGCCGCTTCTGGAAGCATGAGTGGG | 88 | RNASET2 | ribonuclease T2 |
| ATACCTCAGAGCTGGCGGCTGTACC | 89 | RNF213 | ring finger protein 213 |
| GCCCTGAATGATTTTTGCTGCAATT | 90 | RPS16P5 | ribosomal protein S16 pseudogene 5 |
| GAGCATAGTCTAGGGGTGGGGTATC | 91 | SAMHD1 | SAM and HD domain containing deoxynucleoside triphosphate triphosphohydrolase 1 |
| GCTCGGGCTACTTCGAGCAGGAGTC | 92 | SDC3 | syndecan 3 |
| TCTTCTTTAAAGGCAAATGGGAGAG | 93 | SERPINA1 | serpin family A member 1 |
| AGCCTGAAAGTGAAAGCAAAATCTA | 94 | SIRPB2 | signal regulatory protein beta 2 |
| GGAACAACAGGCCTTATTCCACTGC | 95 | SOD2 | superoxide dismutase 2, mitochondrial |
| ATGAAGAAAGCCCAGAGGCAGAGCT | 96 | SP100 | SP100 nuclear antigen |
| TATTCACCGAAGAGGAAAACCCAAA | 97 | SP110 | SP110 nuclear body protein |
| AGGACAAGGAGATGGGAATGGAAAT | 98 | SPATA13 | spermatogenesis associated 13 |
| AACCCTGGGAGAAAGTCAGCGGACA | 99 | SRGAP2 | SLIT-ROBO Rho GTPase activating protein 2 |
| CTCAGCTCCTGCAGCACCCATTTGT | 100 | STK4 | serine/threonine kinase 4 |
| TATAAAAGACCTATCCCTCTTTGTT | 101 | THEM4 | thioesterase superfamily member 4 |
| TCTCATTGCAGGAAAGGCCGAGGGG | 102 | TIMP2 | TIMP metallopeptidase inhibitor 2 |
| AACGTTTGGGTTTTCCTAGCTACAT | 103 | TMEM14C | transmembrane protein 14C |
| CTCCTGTAGTAACTGTAAGAAAAGC | 104 | TNFRSF1A | TNF receptor superfamily member 1A |
| TTTCCCATGGATTCCTTGGCAGCAG | 105 | TRAK1 | trafficking kinesin protein 1 |
| CAGGTCCCACTCAGGAATCCTCAAT | 106 | TRANK1 | tetmtricopeptide repeat and ankyrin repeat containing 1 |
| GAGGTGGTCCAAGCCCAGGAAGCGC | 107 | TSHZ1 | teashirt zinc finger homeobox 1 |
| ACTGTGGCTGAGCATCTCTGGAAGT | 108 | TUBGCP4 | tubulin gamma complex associated protein 4 |
| CGGCCTCCAAGCGGCCGTGGTGTGT | 109 | UPP1 | uridine phosphorylase 1 |
| ACGCGGGCGCAGTGGTATCTTATT | 110 | USP4 | ubiquitin specific peptidase 4 |

TABLE 6-continued

Probe Sequences

| Context Sequence | SEQ ID NO: | Gene Symbol | Gene Name |
|---|---|---|---|
| CCTACCTCCCAGCCTAATTGACCGG | 111 | ZDHHC18 | zinc finger DHHC-type containing 18 |
| GTTACAAGTGTGAGGACTGCGGGAA | 112 | ZYX | zyxin |

Gene Sequences

SEQ ID NO: 1

```
ctcggtgcgg ttccgccggg cgcgaggagc cgccgagacc tccgcctgcg aacaaagagg
aggccgtgcg gggcgcggcg cccgcggagc atggcggacc gcagcctgga gggcatggcg
ctgcccctgg aggtgcgggc gcgcctggcc gagctggagc tggagctgtc ggaaggtgac
atcacacaaa aaggatatga aaagaagagg tcaaagttaa ttggagccta ccttccgcag
cctccgaggg tggaccaagc tttgccgcaa gaacgccggg ctcctgtcac tccttcctcc
gcctctcgct accaccgccg acggtcttca gggtcacgag atgagcgcta tcggtcagac
gtccacacgg aagctgtcca ggcggctctg gccaaacaca agagcggaa gatggcagtg
cctatgcctt ccaaacgcag gtccctggtc gtgcagacct cgatggacgc ctacacccct
ccagatacct cttctggctc agaagatgaa ggctcagtgc aggggactc ccagggcacc
cccacctcca gccagggcag catcaatatg gagcactgga tcagccaggc catccacggc
tccaccacgt ccaccacctc ctcgtcctct acgcagagcg ggggcagcgg ggctgcccac
aggctggcgg acgtcatggc tcagacccac atagaaaatc attctgcacc tcctgacgta
accacgtaca cctcagagca ctcgatacag gtggagagac cgcagggttc cacggggtcc
cggacagcgc ccaagtacgg caacgccgag ctcatggaga ccggggatgg agtaccagta
agtagccggg tgtcagcaaa aatccagcag cttgtcaata ccctcaaacg accgaaacga
ccaccttac gagaattctt tgtcgatgac tttgaagaat tattagaagt tcaacaaccg
gatccgaacc aaccaaagcc ggagggggcc cagatgctgg ccatgcgcgg agagcagctg
ggcgtggtca cgaactggcc gccgtcgctg gaggccgcac tgcagaggtg gggcaccatc
tcgcccaagg cgccctgcct gaccaccatg gacaccaacg ggaagcccct ctacatcctc
acttacggca agctgtggac aagaagtatg aaggtcgctt acagcattct acacaaatta
ggcacaaagc aggaacccat ggtccggcct ggagatagg tggcactggt gttccccaac
aatgatccgg ctgccttcat ggcggctttc tacggctgcc tgctggccga ggtggtcccc
gtgcccatcg aggtgccgct caccaggaag gacgcaggga gccagcagat aggttctg
cttgaagct gtggagttac tgtagccttg actagtgacg cctgccataa aggacttcca
aaaagcccaa cgggagagat cccacagttt aaaggttggc caaagctgct gtggtttgtc
acagagtcta acatctctc caaaccgccc cgagactggt tcccacacat taaagatgcc
aataacgaca ctgcgtatat tgagtacaag acgtgtaagg atggcagtgt gctgggtgtg
acggtgacga ggactgcgct gctgacacac tgccaggccc tgacgcaggc gtgtggctac
acggaagctg aaaccattgt gaatgtgctg gatttcaaga aggacgtcgg gctctggcat
ggcatcctga caagcgtcat gaacatgatg catgtgatca gcatcccgta tcgctgatg
aaggtgaacc ctctctcctg gatccagaag gtctgccagt acaaagcaaa agtggcgtgt
gtgaaatcga gggatatgca ttgggcatta gtagcacaca gagatcagag agacatcaac
```

| Gene Sequences |
|---|
| ctctcctctc tgcgaatgct gatagtggcg gacggcgcga acccctggtc tatttcttct |
| tgcgatgcat ttctcaatgt cttccaaagt aaaggccttc gacaggaggt catctgtcct |
| tgtgccagct cgccagaggc cctcactgtg gccatccgga ggcccacgga tgacagtaac |
| cagcccccgg gccggggtgt cctctccatg catggactga cctatggggt cattcgtgtg |
| gactcggaag agaagctgtc cgtgctcacc gtgcaggatg tcggcctcgt gatgcctgga |
| gccatcatgt gttcagtgaa gccagacggg gttcctcagc tgtgcagaac ggatgagatc |
| ggggagctgt gtgtgtgtgc agttgcgacg ggcacgtcct actatggcct ctctggcatg |
| accaagaaca cctttgaggt gtttcccatg acaagctccg ggctccgat cagtgaatac |
| ccattcataa ggacaggctt gctggggttc gtgggtcccg gaggcctcgt cttcgtggtg |
| ggcaagatgg atggcctcat ggtggtcagc gggcgcaggc acaacgccga cgacatcgtg |
| gccactgcgc tggccgtaga acccatgaag tttgtctacc ggggaaggat agccgtgttc |
| tcggtgaccg tgctgcacga cgagaggatc gtgatcgtgg ctgagcagag gcctgactcc |
| acggaagagg acagtttcca gtggatgagc cgtgtgctgc aggcgattga cagtatacat |
| caagttggag tttattgcct ggccttggtg ccagcaaaca ccctcccaa aacccgctt |
| ggtgggatcc atttatcaga aacaaaacag cttttctgg agggctctct gcaccctgc |
| aatgtcctaa tgtgcccca cacctgcgtc acaaacttgc ctaagcctcg acagaagcag |
| ccagaaatcg gccctgcctc tgtgatggtg gggaacctgg tctctgggaa gagaatcgcc |
| caggccagtg gcagagacct gggtcagatc gaagataacg accaggcacg caagttcctg |
| ttcctctcag aggtcttgca gtggagagca cagaccaccc cggaccacat cctctacacg |
| ctgctcaact gtcggggtgc gatagcgaac tcgctgacct gcgtgcagct gcacaagaga |
| gctgagaaga tcgccgtgat gctgatggag aggggccacc ttcaggacgg cgaccacgtg |
| gccttggtct acccccagg aatagacctg atagcagcgt tttatggttg cctgtacgca |
| ggctgtgtgc aataaccgt ccgtcccccg cacccacaga acatcgcgac gacgttgcct |
| accgtcaaga tgattgtgga ggtgagtcgc tctgcctgtc tgatgacgac acagctgatc |
| tgtaagttgc tgcggtccag ggaggcggcg gcggctgtgg acgtcaggac gtggcccctc |
| atcctggaca cagatgattt gccaaagaag cggcctgccc agatctgcaa accttgcaac |
| ccagacactc ttgcatatct cgacttcagc gtgtccacaa ctgggatgct agctggcgta |
| aagatgtctc acgcagccac cagtgccttc tgccgttcca ttaagctgca gtgtgaactt |
| taccccctcta gagaagtggc catctgcctg gaccttact gtggactggg atttgtcctc |
| tggtgcctct gcagtgtgta ttctgggcac cagtccatcc tgatcccgcc ctctgagctg |
| gaaaccaacc ccgccttgtg gcttcttgcc gtgagtcagt acaaagtccg agacacgttt |
| tgctcctact ccgtgatgga gctgtgcacc aaggggctgg gctcgcaaac agagtccctc |
| aaggcgcgag ggctggactt gtcccgagtg aggacctgcg tggttgtggc ggaagagagg |
| cctcggatcg cactcacaca gtcgttctca aagctgttta aggacctggg ccttcacccg |
| cgggccgtca gcacctcgtt cggttgcagg gtgaacctgg cgatttgctt gcagggaacc |
| tcaggacctg acccaaccac tgtctacgtg gacatgagag ccctgagaca cgacagagtc |
| cgcttagtgg aaagaggatc ccctcatagt ctgcccctga tggaatcggg aaagatactt |
| ccaggggttc ggattataat tgccaaccca gaaacaaaag gaccgctggg ggactcacac |
| cttggagaga tttgggttca cagtgcccac aatgccagcg gttatttcac tatttacgga |

-continued

| Gene Sequences |
|---|

```
gacgaatccc tccagtcaga tcacttcaac tcaagactaa gttttggaga cacccagacc atctgggcac gcacaggcta cttggggttc ctgcggagaa ctgagctcac agatgcaaat ggagagcgcc atgatgccct ctacgtggta ggggcactgg acgaagccat ggagctgcgg ggcatgcggt accacccaat cgacattgag acctcggtca tcagagccca taaaagcgtt acggaatgtg ctgtgtttac ctggacaaat ttgttggtgg ttgtggttga gctggatggg tcggaacaag aagccttgga cctggttccc ttggtgacca acgtggtcct ggaggagcac tacctgatcg tcggagtggt ggtcgtggtg gacatcggcg tcatccccat caactcccgt ggggagaagc agcgcatgca cctgcgagac gggttttgg cagaccagct agacccatc tatgtggcct acaacatgta gtctcgtctc ttggcttcca tggacttttc tagagatgta gacattgttc tccgtgtcca ctgaagcgtg cagacacagg caacactca ccagaataca gccattgtg gtgagagtgg aggaggaaga ggaggaggaa gaggacttct cacagcagcc acgattggca tgggggtgaa atgtgaattt accactgaat ttcgctcaga aggactttgg attactgcct tcagtttgtt ggaaaagccc atttcaaaac tttctttct tttctttctt ttttaattat tggataataa gtgctttctt cgtaaatgtg gtattttgtt aagccgaaat agcaattaaa aaatatcct gccctccaga tgggttcttt taaacaattt atgtagtgtg acaaagaatt gttttctctg ttttaatgtg tcatgaaatc ttaatgacat ggatctgtta ctaatttaag ccattgctag atctcatcct tttaggaaag tttgaggtac gagaaaacct tccaatagc accttccaat tagataatag cagctttctt tgtcagaaat gtgctgaaga aacaaaggct ggtatacggc cttcgaagtt agtatagaat gagaagaaat tataaataag gtgtatttcg gcaattatct tgcaaatatc tttgtactaa actaaaaaga taaaataagt taacttcctc aatatgtaat tatgtacaaa acgtttaatt tattttgatc tctttagaac tataaaagag aaaaacattc aagaatatta aagtcttgta atgtttgcta atataaaaaa gtgttgtatt atcttgcgtg gatagtatca caacaaatat atatatatga aatataaatt cactaatgaa caaaggagat tttaaagttt aagatgcaga acttgtcact tgcatggtgt gccccccgta ctcacataca ctctgctgtt gccagcagtc gcagaccgca ggagccctgt ctaaaagttt cttctagaac cagagaccag caagtgaaat tattgccatc tcaaggatgg caaaagaatt caaagctcaa tgtgcactat ttttttctt gctgtgggac aacagtgaat gtgtttatgc cagcgtgtgc tgatgatact gaggggcttt aggttggcaa atagcactgt tttcttagct gcaagaattc attgcacaat gttttcatc attttgtta atgtcatctt tttttggtcc ttgctacgaa aaggaatgcg attctgtggt cattcgcact gggttgcatt gattccccct ctgatggcca atgtggagtg acaaagtgt ccggaactca catcggtgat cgtcccctcg tcttaagacc cagcccgctc tgtgtgagcc tctggggctc cctcgctcag tgagcacagt tccccggggg ttcatgccag agctccggct gaagcaagaa gtcctccagc tgcgtcgttt gccgcctgtg gacgagtgcg ccccagtttc tgccctggca gctcctggcc acaccttctc agagctcacc tgtgcacttc taaattgaat tgggcccacgg tgtccaacca agaaggagca tctgcactcc gagaaagatg tgttctgtaa ctgccccagt gtgaccccgc agtggctctc ggtgctagat atgcatgact aagattgatg ctgggcaaaa tgtagatgat ctttcattat gttgtgggca gcgtctttct ctgcctttgc tatatgcagt cagcagtaag
```

| Gene Sequences |
|---|
| ccttttgcta aaagagtttt gtttgacttc tgagatccaa ggctgattgt tgttaaaaaa |
| aaaaaaaaaa aaaaagtggc acatttaaaa aaatgtgtct gcatatgtgg tgcatccttc |
| catctccaca aaccatttga ttcttgaaat attgtttgac ctcattgctg tgtgtgaata |
| tttctccaca tgcttcagat gcacattcct agtctctgct tcctaagggg ggaaccacca |
| cacattgggg ggaaaaaaga catttttccta cacccaccca ccttgttgaa agggaggtag |
| gtttggggct tcaggccagg cactgactat gaaacattag ctgcagtgtg caggacagct |
| ttgaggtcca gctgaagtca ggaagcaaaa caaatgtaga tgtcacttca aacataattt |
| caactgtcac cagatcaact ctacattcaa ggagtgtgga cgctgcagtg cagttgtgag |
| ggcagttagc agccgcctct tctgcatcct gtcaactctg attagttaga gtttaggctc |
| aaaagagttg gtggactgag attgaaattt ggttgtgcaa gagaaaggaa aggagacact |
| tagtaccacc agtttcagca ataaagaagg gtcattctgt attcaaaatt gtactgtaga |
| taaatcattc atgagattgt aaaaaatgtt tgtcttgtga cctgtgcttt ttgaagtcag |
| acaaaaccgt gtaatcaact tgcacaaaaa gagggtacac agtgaacata taaacacaga |
| cctaatcaaa caggagcaga ttcctcatgg tgcttgttta ttatatatat ttaatcctgc |
| ttgacacttt acccaaggga gatggtccct tttatcagtt gaatgttagc agcgttattt |
| cagagtgtgg tgactggtta gagaaactca tgtactcaac cagccacagt ttcaaacaaa |
| atttttatgt gcaaggaca gcaaccttct tgtatgttaa accaccagta cgctttgtac |
| atctgtgata acgcctgttt tatattcaaa tgaacaaata aaagcttttaa tttttgttgc |
| tctgaaaata gcagtttctt aattggtccc ctggaaagat gtctgggaca gctttaatcc |
| cgggaaggaa gtgactccta cagggaaatg tatctgactc tgtttacata atttgttgca |
| ttacttagta cagataatca tactttgaaa aatgttttaaa ttttgatgtg gcatttatt |
| gctaaaaata attcctatgg caacaaatgt tttgtgaaat gttttttta attcttttaa |
| atatatctaa atatatttgt tcaca |

SEQ ID NO: 2

MADRSLEGMALPLEVRARLAELELELSEGDITQKGYEKKRSKLI

GAYLPQPPRVDQALPQERRAPVTPSSASRYHRRRSSGSRDERYRSDVHTEAVQAALAK

HKERKMAVPMPSKRRSLVVQTSMDAYTPPDTSSGSEDEGSVQGDSQGTPTSSQGSINM

EHWISQATHGSTTSTTSSSSTQSGGSGAAHRLADVMAQTHIENHSAPPDVTTYTSEHS

IQVERPQGSTGSRTAPKYGNAELMETGDGVPVSSRVSAKIQQLVNTLKRPKRPPLREF

FVDDFEELLEVQQPDPNQPKPEGAQMLAMRGEQLGVVTNWPPSLEAALQRWGTISPKA

PCLTTMDTNGKPLYILTYGKLWTRSMKVAYSILHKLGTKQEPMVRPGDRVALVFPNND

PAAFMAAFYGCLLAEVVPVPIEVPLTRKDAGSQQIGFLLGSCGVTVALTSDACHKGLP

KSPTGEIPQFKGWPKLLWFVTESKHLSKPPRDWFPHIKDANNDTAYIEYKTCKDGSVL

GVTVTRTALLTHCQALTQACGYTEAETIVNVLDFKKDVGLWHGILTSVMNMMHVISIP

YSLMKVNPLSWIQKVCQYKAKVACVKSRDMHWALVAHRDQRDINLSSLRMLIVADGAN

PWSISSCDAFLNVFQSKGLRQEVICPCASSPEALTVAIRRPTDDSNQPPGRGVLSMHG

LTYGVIRVDSEEKLSVLTVQDVGLVMPGAIMCSVKPDGVPQLCRTDEIGELCVCAVAT

GTSYYGLSGMTKNTFEVFPMTSSGAPISEYPFIRTGLLGFVGPGGLVFVVGKMDGLMV

VSGRRHNADDIVATALAVEPMKFVYRGRIAVFSVTVLHDERIVIVAEQRPDSTEEDSF

| Gene Sequences |
| --- |
| QWMSRVLQAIDSIHQVGVYCLALVPANTLPKTPLGGIHLSETKQLFLEGSLHPCNVLM |
| CPHTCVTNLPKPRQKQPEIGPASVMVGNLVSGKRIAQASGRDLGQIEDNDQARKFLFL |
| SEVLQWRAQTTPDHILYILLNCRGAIANSLICVQLHKRAEKIAVMLERGHLQDGDHV |
| ALVYPPGIDLIAAFYGCLYAGCVPITVRPPHPQNIATTLPTVKMIVEVSRSACLMTTQ |
| LICKLLRSREAAAAVDVRTWPLILDTDDLPKKRPAQICKPCNPDTLAYLDFSVSTTGM |
| LAGVKMSHAATSAFCRSIKLQCELYPSREVAICLDPYCGLGFVLWCLCSVYSGHQSIL |
| IPPSELETNPALWLLAVSQYKVRDTFCSYSVMELCTKGLGSQTESLKARGLDLSRVRT |
| CVVVAEERPRIALTQSFSKLFKDLGLHPRAVSTSFGCRVNLAICLQGTSGPDPTTVYV |
| DMRALRHDRVRLVERGSPHSLPLMESGKILPGVRIIIANPETKGPLGDSHLGEIWVHS |
| AHNASGYFTIYGDESLQSDHFNSRLSFGDTQTIWARTGYLGFLRRTELTDANGERHDA |
| LYVVGALDEAMELRGMRYHPIDIETSVIRAHKSVTECAVFTWTNLLVVVVELDGSEQE |
| ALDLVPLVTNVVLEEHYLIVGVVVVVDIGVIPINSRGEKQRMHLRDGFLADQLDPIYV |
| AYNM |

SEQ ID NO: 3 agtcctgacc gcacggggc cgcggccacg gggcgcaggg gccatggtgc gcggcaggat
ctcccggctc tcggtccggg acgtgcgctt ccccacgtcg cttgggggcc acggcgcgga
cgccatgcac acggaccctg actactcggc tgcctatgtc gtcatagaaa ctgatgcaga
agatggaatc aagggggtgtg gaattacctt cactctggga aaaggcactg aagttgttgt
ctgtgctgtg aatgccctcg cccaccatgt gctcaacaag accctcaagg acattgttgg
tgacttcaga ggcttctata ggcagctcac aagtgatggg cagctcagat ggattggtcc
agaaaagggc gtggtgcacc tggcgacagc ggccgtccta acgcggtgt gggacttgtg
ggccaagcag gagggaaagc ctgtctggaa gttacttgtg acatggatc ccaggatgct
ggtatcctgc atagatttca ggtacatcac tgatgtcctg actgaggagg atgccctaga
aatactgcag aaaggtcaaa ttggtaaaaa agaaagagag aagcaaatgc tggcacaagg
ataccctgct tacacgacat cgtgcgcctg gctggggtac tcagatgaca cgttgaagca
gctctgtgcc caggcgctga aggatggctg gaccaggttt aaagtaaagg tgggtgctga
tctccaggat gacatgcgaa gatgccaaat catccgagac atgattggac cggaaaagac
tttgatgatg gatgccaacc agcgctggga tgtgcctgag gcggtggagt ggatgtccaa
gctggccaag ttcaagccat tgtggattga ggagccaacc tcccctgatg acattctggg
gcacgccacc atttccaagg cactggtccc attaggaatt ggcattgcca caggagaaca
gtgccacaat agagtgatat ttaagcaact cctacaggcg aaggccctgc agttcctcca
gattgacagt tgcagactgg gcagtgtcaa tgagaacctc tcagtattgc tgatggccaa
aaagtttgaa attcctgttt gccccatgc tggtggagtt ggcctctgtg aactggtgca
gcacctgatt atatttgact acatatcagt ttctgcaagc cttgaaaata gggtgtgtga
gtatgttgac cacctgcatg agcatttcaa gtatcccgtg atgatccagc gggcttccta
catgcctccc aaggatcccg gctactcaac agaaatgaag gaggaatctg taaagaaaca
ccagtatcca gatggtgaag tttggaagaa actccttcct gctcaagaaa attaagtgct
cagccccaac aactttttc tttctgaagt gaaagggctt aaaatttctt ggaaatagtt
ttacaaaaat ggatttaaaa aatcctaccg atcaagatga gttcagctag aagtcatacc -continued

| Gene Sequences |
|---|
| accctcagga atcagctaag taattattac ttgattcttt tagcaaatca atgcacgtta |
| tcctacttaa tccttaaata agtttagatt taactaaccc aaagtccagg aggatgttct |
| tacaaaaata gctatatcaa gggctggcac ctagacatta aactgtaatt tgaaaataag |
| caacatgttg cataacttgt tggaataatt ccttgttctg tttaacactt gtcataaatt |
| agcagaataa aaatagtcgt gcaacaccgg gggtatctgg tatgcaacga agggaaaaat |
| atttcactga ttaaccccga agtggttttg catcttttcc ttgcttaatc taagcatatt |
| attagagaag tcacaccatg ctgaagctaa tgagggcaaa atggtagtcc atagattatt |
| ttaaaataac cctttaaggt tataaaagtt taaaaaaaaa aaaaaaaac tctatcctaa |
| atggtcatta tattttgagg ataagatgca gttaaaatga gaaaaatagg gcaaaatata |
| ttcactatta tttctaaaat atactctttt aagtagcatc caaaccagaa tacagcacat |
| gtttacttaa ggagagttct ttaatctatt ttaggaagga actgagcaga taagtggcag |
| tacagaatga acaaagcgtg gacgaatgca gaacacttct ttattatagc aacatataaa |
| acaactataa ctttaaagtt cataaccaca ctctacatca tgatcgatgg tgttactcag |
| ctccctcaga tttgagggaa tagcttgtga aattcttaaa atattctaaa aatattccaa |
| aaatagcttg tgaaattcac caaccttctt tataagtacg tgggattgaa atgcacatac |
| atgttttgc taagagcaca tacatttcat tctcctcact ttgttcataa cctcagcatt |
| gtcagatacc ctcagtgagt taactcaaag cctttatta tggaaagaac tggcacagtt |
| acatttgcca gtggcaacat ccttaaaaat taataactga taggtcacgg acagattttt |
| gacctagttc cttttctt tagagcaaaa agaacttta cctcggcatc cagcccaacc |
| cctaaagact gacaatatcc ttcgagctcc tttgaaagca ccctaaacag ccatttccat |
| tttaatagtt ggatgcggat tgtacccttc aatctgaaag tcttcagctt tgaagtcatc |
| aattttctca acttttcgaa gaatcctgag ctttgggaaa ggtctgggtt ctcgctgaag |
| ctaaaaacaa aataaggcca ttattttgcc ataattgtac gacctgttgt aattgctcct |
| catgtccgtg aaacaagtac acaggatgtg atcaacaaag ttctatttta caggagtatg |
| atcctgtcga taccttgccg taggttatgt aacatgattg gagcgcaacc agctgttctc |
| ttgcacagat cgagagtgag gggtatttttg tgacattaca cagcatcagg agcctggtgc |
| ctcatcaggt gtaagttctt ataaccactc ttggcaaatt tattaaagac aggaacacag |
| tcaatctgta actcatagta gctctacgtt tacttgaatt ccacaatccc taacccatct |
| gtccctggca gaaagaagga aagatgacat gcatggacag tgaacagaaa gggatgaaag |
| ccaggattcc tgggatgaac agacagtggc aattaggatg tgaagacagg tcacaaccta |
| ttactatgtc taaaaacgac cagagcagag agccagagag aataagcctg aagtcacctc |
| cactcaaaag cagccaaact ccctcaaagg agtaactttt aaaacctgga tctaacctgg |
| aaggggctaa aaagtgtctg gttctgagtt ttttccctta aggctcatga agcagatgaa |
| cttacatttt tattgccatt tcatatcaat tgttggctgc tataacttag ggatttcaac |
| agactttga agtttggacc taaatattgt acttaatgta aaattaacaa aaaatattta |
| tggccagggt ggtggcttat gcctgtaatt ccagaatttt cggaggctga ggcaggtgga |
| tcacttgaag tcaggagttt gagactagcc tggccaacat gatgaaaccc catctctact |
| aataatacaa aaattagctg ggtgtggtgg catgtgcctg taatcccagc tacctgggag |
| gctgaggcag aagaattgct tgaacccggg aggtggaggt tgcagtgagc tgagatcgca |

-continued

Gene Sequences ccacggcaca ctccagcctg gccgacagag aaagactcca tctcaaaaaa aaagaaaag
gaaaaacatt tgcacttcaa ttctccttca agttaaaatg agttaaaatg cccccttttg
gacaatcccc tggcttgaat gtggctcttc cctctctggt actggtgctt agtacctcac
agcacctgac atgttaagtg cccatggttg ctgaggcaga tgcctgcctt gtcctgccca
cctgcccacc acttctccct aaactgaagc cccacatttg gagcagtcat ctttatcttg
gacacagcat tgagcagatg cctgttccac agtcaacctt ttatcaagag aaggtaccaa
acccaaaagt ataacatcta attcttacct gaattttcag tggctcgatg tgattcaggt
aaatatgtgc atctcccaaa gtgtgtataa agtcacctgg ctataaaccc ggggagaaa
gcagaacagt atgttagttt caattcttta aaacatcatt taaaaacatt agaatatgca
gacaccgcaa ggcttttttt aaaaaaataa tttagtgtag cttttccatt tttttgtagc
aacagcatct tgttatgttg cccaggctgg tattgaactc cagacctcaa gcaattgctc
ctgtctcagt ctcccaaagt gctgggatta caggcatgag ccaccatacc caacctcagc
atagcttttg agaaaatcca tagaagctgt atcacaaaca acctgtatag atctgttagt
gcgtatacca cagggccaga aaaccttcca gaagaggaag gtttcaaagt aaaagctggt
tcatttctta cttacacata tcaaatttaa aagctaatca gagactaaac tctgcaattt
gttttcccat attaaagaac tgaagagctc agtgtggtag gctggcaagt caccctccc
gagacagccc accttcaggc ccgtgatgtg cgcaatcatg tacgtgagca gggcgtagct
ggcgatgttg aaaggcacac cgaggcccat gtctcccgat ctctggtaca gctggcagga
cagctcactg ttcaccacat agaactggca gagggcatgg catggaggca gcgccatcag
aggaagatct gaggaaccag cagaggaaga taaggaggga tggtggtttg aaagaccaca
gctaaaggca aagtaaaaca ggagagaaac agaagccaac tcatatggtg agaccagga
gagagagcca ctgggctgca gtgatgtcca taacagcctc tgcagcgatg cacggagct
gagggagact atccatcggt gcaaggtttc tgcaggtgtc catttacggc tgaagcaatg
ctcttccatc agagctgaag ggatctgggc tacctcgtgg caccagatta caaatacagc
aggaataatt ctgtttgcca caggaaactg gtgcttctgg tacaccctcc tatattaaaa
gtctctatta catggccagg ca SEQ ID NO: 4
MVRGRISRLSVRDVRFPTSLGGHGADAMHTDPDYSAAYVVIETD
AEDGIKGCGITFTLGKGTEVVVCAVNALAHHVLNKDLKDIVGDFRGFYRQLTSDGQLR
WIGPEKGVVHLATAAVLNAVWDLWAKQEGKPVWKLLVDMDPRMLVSCIDFRYITDVLT
EEDALEILQKGQIGKKEREKQMLAQGYPAYTTSCAWLGYSDDTLKQLCAQALKDGWTR
FKVKVGADLQDDMRRCQIIRDMIGPEKTLMMDANQRWDVPEAVEWMSKLAKFKPLWIE
EPTSPDDILGHATISKALVPLGIGIATGEQCHNRVIFKQLLQAKALQFLQIDSCRLGS
VNENLSVLLMAKKFEIPVCPHAGGVGLCELVQHLIIFDYISVSASLENRVCEYVDHLH
EHFKYPVMIQRASYMPPKDPGYSTEMKEESVKKHQYPDGEVWKKLLPAQEN SEQ ID NO: 5
ggtacgcgga caagatggcg gcggcagcag tcgacagcgc gatggaggtg gtgccggcgc
tggcggagga ggccgcgccg gaggtagcgg gcctcagctg cctcgtcaac ctgccgggtg
aggtgctgga gtacatcctg tgctgcggct cgctgacggc cgccgacatc ggccgtgtct

| Gene Sequences |
|---|
| ccagcacctg ccggcggctg cgcgagctgt gccagagcag cgggaaggtg tggaaggagc |
| agttccgggt gaggtggcct tcccttatga aacactacag ccccaccgac tacgtcaatt |
| ggttggaaga gtataaagtt cggcaaaaag ctgggttaga agcgcggaag attgtagcct |
| cgttctcaaa gaggttcttt tcagagcacg ttccttgtaa tggcttcagt gacattgaga |
| accttgaagg accagagatt tttttgagg atgaactggt gtgtatccta aatatggaag |
| gaagaaaagc tttgacctgg aaatactacg caaaaaaat tctttactac ctgcggcaac |
| agaagatctt aaataatctt aaggcctttc ttcagcagcc agatgactat gagtcgtatc |
| ttgaaggtgc tgtatatatt gaccagtact gcaatcctct ctccgacatc agcctcaaag |
| acatccaggc ccaaattgac agcatcgtgg agcttgtttg caaaacccctt cggggcataa |
| acagtcgcca ccccagcttg gccttcaagg caggtgaatc atccatgata atggaaatag |
| aactccagag ccaggtgctg gatgccatga actatgtcct ttacgaccaa ctgaagttca |
| agggaatcg aatggattac tataatgccc tcaacttata tatgcatcag gttttgattc |
| gcagaacagg aatcccaatc agcatgtctc tgctctattt gacaattgct cggcagttgg |
| gagtcccact ggagcctgtc aacttcccaa gtcacttctt attaaggtgg tgccaaggcg |
| cagaaggggc gaccctggac atctttgact acatctacat agatgcttt gggaaaggca |
| agcagctgac agtgaaagaa tgcgagtact tgatcggcca gcacgtgact gcagcactgt |
| atggggtggt caatgtcaag aaggtgttac agagaatggt gggaaacctg ttaagcctgg |
| ggaagcggga aggcatcgac cagtcatacc agctcctgag agactcgctg gatctctatc |
| tggcaatgta cccggaccag gtgcagcttc tcctcctcca agccaggctt tacttccacc |
| tgggaatctg gccagagaag tcttttctgtc ttgttttgaa ggtgcttgac atcctccagc |
| acatccaaac cctagacccg gggcagcacg gggcggtggg ctacctggtg cagcacactc |
| tagagcacat tgagcgcaaa aaggaggagg tgggcgtaga ggtgaagctg cgctccgatg |
| agaagcacag agatgtctgc tactccatcg ggctcattat gaagcataag aggtatggct |
| ataactgtgt gatctacggc tgggaccca cctgcatgat gggacacgag tggatccgga |
| acatgaacgt ccacagcctg ccgcacggcc accaccagcc ttctctataac gtgctggtgg |
| aggacggctc ctgtcgatac gcagcccaag aaaacttgga atataacgtg gagcctcaag |
| aaatctcaca ccctgacgtg ggacgctatt tctcagagtt tactggcact cactacatcc |
| caaacgcaga gctggagatc cggtatccag aagatctgga gtttgtctat gaaacggtgc |
| agaatattta cagtgcaaag aaagagaaca tagatgagta aagtctagag aggacattgc |
| acctttgctg ctgctgctat cttccaagag aacgggactc cggaagaaga cgtctccacg |
| gagccctcgg gacctgctgc accaggaaag ccactccacc agtagtgctg gttgcctcct |
| actaagttta ataccgtgt gctcttcccc agctgcaaag acaatgttgc tctccgccta |
| cactagtgaa ttaatctgaa aggcactgtg tcagtggcat ggcttgtatg cttgtcctgt |
| ggtgacagtt tgtgacattc tgtcttcatg aggtctcaca gtcgacgctc ctgtaatcat |
| tctttgtatt cactccattc ccctgtctgt ctgcatttgt ctcagaacat ttccttggct |
| ggacagatgg ggttatgcat ttgcaataat ttccttctga tttctctgtg aacgtgttc |
| ggtcccgagt gaggactgtg tgtctttta ccctgaagtt agttgcatat tcagaggtaa |
| agttgtgtgc tatcttggca gcatcttaga gatggagaca ttaacaagct aatggtaatt |
| agaatcattt gaatttattt ttttctaata tgtgaaacac agatttcaag tgttttatct |

Gene Sequences

```
tttttttttta aatttaaatg ggaatataac acagttttcc cttccatatt cctctcttga
gtttatgcac atctctataa atcattagtt ttctatttta ttacataaaa ttcttttaga
aaatgcaaat agtgaacttt gtgaatggat ttttccatac tcatctacaa ttcctccatt
ttaaatgact acttttattt tttaatttaa aaaatctact tcagtatcat gagtaggtct
tacatcagtg atgggttctt tttgtagtga gacatacaaa tctgatgtta atgtttgctc
ttagaagtca tactccatgg tcttcaaaga ccaaaaaatg aggttttgct tttgtaatca
ggaaaaaaaa aaattaatga acctaaaaaa aaaaaaaaaa ggttttgaag ggaaaaaaag
tggtttcaca cctcttgtta ttccttagag tcacttcaag gcctgtttga atgtggcagg
ttagaaagag agagaatgtc tttcatttga agagtgttgg acttgtgtga aaggagatgt
gcgtgttgga atctgctttt ccaagccgcc agggtcctga cggcagcagg acgaagcctg
ttgtggcgtc ttctgggaaa gcctgaccgt gtgttcggac ggcactggct cctttccgaa
gttctcagta actgagccca gagtaactgc acgcctttgt gcagctctgg agctccacca
actctcggcc tgccagttct caagcgagct aatcttgtca ttaatcgata gaagctaact
tccgaagtta ggacctagtt actttgctct caacatttaa aataatgcag ttgctctagt
gaatggggcg ttaggggcct gtctctgcac ctgtctgtcc atctgcatgc agtattctca
cccatgttga atgcctgctg cttgtttacc ctttggaaac cctggggtga ccaaggtttg
gaaagccacc tgagaccact tcatagcaag ggaaggcttt aagcagttac tagaaagaga
tggggatttg gcccctggct cctccagcct gaatgagcta tttaatccac tgtccatgtt
cctcatcagt caaatccaaa gtcaaaggat ttgaacctgc atctggaaac gtaaccactc
acagcacctg gcccgccaag gttgggagga ttgtacacta ctttcattta aaggggaaag
tttgataata cggaattaat taatatgaat gagatgcatt aataagaacc tgagcatgct
gagagttgca attgttggtt ttctggtttg attgatttcc tttttctta gacacatcaa
agtcaagaaa gatggtttta cctttactga cccagctgta catatgtatc tagactgttt
ttaaatgtct ttcttcatga atgcttcatg gggctccagg aagcctgtat cacctgtgta
agttggtatt tgggcacttt atattttct aaaaacgtgt tttggatcct gtactctaat
aaatcataag tttcttttta aaatttcc aaaacttttc tccatttaa aaagccctgt
tataaacgtt gaactttcac aatgttaaaa tgttaaatat ttggatatag caacttcttt
tctcttcaaa tgaatgccaa gattttttg tacaatgatt aataaatgga acttatccag
agaaaccacg caaatggcct gcccaatttc gtttgaggac agaaagccca gccatgactt
gagtagaatg tctctcacct ctcttcggat ctaaatatga aaagtatgtt ctgctgaatt
tttctgagca ttggtgagcg gacagcctac ctgtaaacca tgacctcctt gccaaacgtt
aattttatca gctcactagt aacctttgag aattatctgg ttgtcatgca agattgcac
tttctgaatt atgttaaaac acatgttgta aaatgagaac tgctcatgct ttgaaagaaa
accaggttct tcgtgcgttc tgttgccgtt gatttgaatg gctgtgctgt atacgatgtg
tccagaatgt cttcagagca ctgtttccgt gtgatgttac tacctactat gtgggaggaa
aaaaggttat aggttaaaca aagtcaattg actctatggt ggtgtttctc aatacctgtg
acgcacagta ctgtgcgtcg tgactttcta agagaagtgt gcagcgggtg tgtcatcttg
atatatgaaa ccctggaatt tccctcccct acacgcacgc accgtccccg ggggtccggt
```

-continued

| Gene Sequences |
|---|
| gtttgcagac atgctttgaa aagctgtctc agtgagacat cagttatgtc caaaatgagt |
| ttaccttaga atcagaccgg ttttgccagg cgtcatgttt gcaaacatta tccacctaat |
| cagattttga aaggccggct ttcatgtcgc ctgcctgaga ctcataacag atccccatta |
| taagcgcgtt tacacagcaa aatgatttta ttgagaaaac cagcattaag tactgttgcc |
| ggctcagttt tccattgcat actatctact taaagtcccg ttctcatttg taagtgttcc |
| gatctttccc cacggagaaa actgagcaga gctgccgtgt cgcaggcttt ctgctgctga |
| tgtcgcatct ctttgctttc ccctccttag tccatactcc aagtaagtga actcagacta |
| ccagcaactt tttaactgaa aagtatctgt ccatgatgat caagatgcag ctcttcgtgt |
| ttttattttg tcttttttttt tttttttttt ttttggaggg aaggagagac atcaactgga |
| caaaatgcaa aatttggatg tgggacaatt gcttttggga gacgtgaata gctgtactgt |
| acgtattatt ttgtgtggca tgctaacttt gagccgggca ctggcctaat aaagtctttg |
| taatcctccc agcaatccta taaagcagac gcagatagta aagattttag gctttgcagg |
| ccacgtacag actgtcacat gttctctgtt tttaaaagtg tcaacaacat tcttagctca |
| aaaacaggct gcaggtggga tggtgcccac aggccatagt tggctgaccc cggctagggt |
| gtaggcactt agcattccac tgtataaagg ggaaacccag gtcatactgc gtgtgcgtgg |
| gtgggaagcc ggatgtggaa tacaggtggt ccctgagtct ccaggaacca ctgagctcca |
| gctgttcaca cccacactct gcggcgcaag caactacctc gccacggttt agccttggtc |
| tagcagcgac tttaaccttg aatgttgcat ttctgaaaaa tttagaatct tgaaagtaaa |
| ggacgtccct ccggtgaata aaattaggcg caattataga atacatgtat tatggccacg |
| tagcaatgac tgtattaggg ctctgctagt tctgtaataa atagacccga aaagcaa |

SEQ ID NO: 6

MAAAAVDSAMEVVPALAEEAAPEVAGLSCLVNLPGEVLEYILCC
GSLTAADIGRVSSTCRRLRELCQSSGKVWKEQFRVRWPSLMKHYSPTDYVNWLEEYKV
RQKAGLEARKIVASFSKRFFSEHVPCNGFSDIENLEGPEIFFEDELVCILNMEGRKAL
TWKYYAKKILYYLRQQKILNNLKAFLQQPDDYESYLEGAVYIDQYCNPLSDISLKDIQ
AQIDSIVELVCKTLRGINSRHPSLAFKAGESSMIMEIELQSQVLDAMNYVLYDQLKFK
GNRMDYYNALNLYMHQVLIRRTGIPISMSLLYLTIARQLGVPLEPVNFPSHFLLRWCQ
GAEGATLDIFDYIYIDAFGKGKQLTVKECEYLIGQHVTAALYGVVNVKKVLQRMVGNL
LSLGKREGIDQSYQLLRDSLDLYLAMYPDQVQLLLLQARLYFHLGIWPEKSFCLVLKV
LDILQHIQTLDPGQHGAVGYLVQHTLEHIERKKEEVGVEVKLRSDEKHRDVCYSIGLI
MKHKRYGYNCVIYGWDPTCMMGHEWIRNMNVHSLPHGHHQPFYNVLVEDGSCRYAAQE
NLEYNVEPQEISHPDVGRYFSEFTGTHYIPNAELEIRYPEDLEFVYETVQNIYSAKKE
NIDE

SEQ ID NO: 7

| ctcttatata aattctaaaa attgatgttc taagaagaga ggtagaattt gaatgactgg |
|---|
| gttacttcct agactcttcc tccttctctt aagtacagta tagttctttc tctgaaaatc |
| ttcagtctct tagttccaga tgggttctct atggtaagaa tacaggacat gtagaaggcc |
| ctaggggaat gctttcttcc ccagatcttt gccctgtagt aggtttcagc tgagcaagga |
| cgagtagttt ttctggtgtt tggcctcctc tgttgggtgg aaaaagactt tcttctctat |
| ttcctagtt atatatgcta tcatatgtct gttttttctcc tcttgaagtt tccctgaaac |

-continued

Gene Sequences ctgggctctt gaagacgcat cactggagca gatggataat ggagactggg gctatatgat gactgaccca gtcacattaa atgtaggtgg acacttgtat acaacgtctc tcaccacatt gacgcgttac ccggattcca tgcttggagc tatgtttggg ggggacttcc ccacagctcg agaccctcaa ggcaattact ttattgatcg agatggacct cttttccgat atgtcctcaa cttcttaaga acttcagaat tgaccttacc gttggatttt aaggaatttg atctgcttcg gaaagaagca gattttacc agattgagcc cttgattcag tgtctcaatg atcctaagcc tttgtatccc atggatactt ttgaagaagt tgtggagctg tctagtactc ggaagctttc taagtactcc aacccagtgg ctgtcatcat aacgcaacta accatcacca ctaaggtcca ttccttacta gaaggcatct caaattattt taccaagtgg aataagcaca tgatggacac cagagactgc caggtttcct ttacttttgg accctgtgat tatcaccagg aagtttctct tagggtccac ctgatggaat acattacaaa acaaggtttc acgatccgca cacccgggt gcatcacatg agtgagcggg ccaatgaaaa cacagtggag cacaactgga ctttctgtag gctagcccgg aagacagacg actgatctcc gaccctgcca caggttcctg aaagactct ccaggaaatg aagatactg attttttttt ttaaatcaca gtgtgagata tttttttct tttaaatagt tgtatttatt tgaaggcagt gaggaccaga aggaagtttt gtgctttggc agactcctcc atgttttgtt cccttccccc tgagtatgca tgtgcctgtt cagagtctcc agatacctt tttataaaaa gaagtctgaa aatcattatg gtatataatc tacccttaac agagcttttc ttattacagt gctaaaatga tttctgataa aatggtccct aactcaacta gaaggctaaa aatacaagaa tgaaagaata agcagagtac tcatgatgcc tttgagaaaa atcaaaacat catgtagggt gacctagttt ccaaaccaat aaataagtag tattgtaata ttaaaggaaa actgttccaa tcatttaaaa gtacttatta agtactgctt tttacagtta tgacaactgt ttcttctat gcatataaat caaggaacca aatatctgta gccatggaaa tgtctgacta gaaatattta tattgaattc tgaatacaaa atgtccctgt ggtagaaaac ttactcttta tgcctggtgc agtataattc ccaagtgtac tgtctaccag aaaaaaaaaa caaaactaat aaaaaatgaa atatgaaaat taaaaaaaaa

SEQ ID NO: 8

MDNGDWGYMMTDPVTLNVGGHLYTTSLTTLTRYPDSMLGAMFGG

DFPTARDPQGNYFIDRDGPLFRYVLNFLRTSELTLPLDFKEFDLLRKEADFYQIEPLI

QCLNDPKPLYPMDTFEEVVELSSTRKLSKYSNPVAVIITQLTITTKVHSLLEGISNYF

TKWNKHMMDTRDCQVSFTFGPCDYHQEVSLRVHLMEYITKQGFTIRNTRVHHMSERAN

ENTVEHNWTFCRLARKTDD

SEQ ID NO: 9 gactattgcg cctgcgccag cgccggctgc gagactgggg ccgtggctgc tggtcccggg tgatgctagg cggctccctg ggctccaggc tgttgcgggg tgtaggtggg agtcacggac ggttcggggc ccgaggtgtc cgcgaaggtg gcgcagccat ggcggcaggg gagagcatgg ctcagcggat ggtctgggtg gacctggaga tgacaggatt ggacattgag aaggaccaga ttattgagat ggcctgtctg ataactgact ctgatctcaa cattttggct gaaggtccta acctgattat aaaacaacca gatgagttgc tggacagcat gtcagattgg tgtaaggagc atcacgggaa gtctggcctt accaaggcag tgaaggagag tacaattaca ttgcagcagg -continued

| Gene Sequences |
|---|
| cagagtatga atttctgtcc tttgtacgac agcagactcc tccagggctc tgtccacttg |
| caggaaattc agttcatgaa gataagaagt ttcttgacaa atacatgccc cagttcatga |
| aacatcttca ttatagaata attgatgtga gcactgttaa agaactgtgc agacgctggt |
| atccagaaga atatgaattt gcaccaaaga aggctgcttc tcatagggca cttgatgaca |
| ttagtgaaag catcaaagag cttcagtttt accgaaataa catcttcaag aaaaaaatag |
| atgaaaagaa gaggaaaatt atagaaatg gggaaaatga agaccgtg agttgatgcc |
| agttatcatg ctgccactac atcgttatct ggaggcaact tctggtggtt tttttttctc |
| acgctgatgg cttggcagag caccttcggt taacttgcat ctccagattg attactcaag |
| cagacagcac acgaaatact attttctcc taatatgctg tttccattat gacacagcag |
| ctccttgta agtaccaggt catgtccatc ccttggtaca tatatgcatt tgcttttaaa |
| ccatttcttt tgtttaaata aataaataag taaataaagc tagttctatt gaaatgcaaa |

SEQ ID NO: 10

MLGGSLGSRLLRGVGGSHGRFGARGVREGGAAMAAGESMAQRMV
WVDLEMTGLDIEKDQIIEMACLITDSDLNILAEGPNLIIKQPDELLDSMSDWCKEHHG
KSGLTKAVKESTITLQQAEYEFLSFVRQQTPPGLCPLAGNSVHEDKKFLDKYMPQFMK
HLHYRIIDVSTVKELCRRWYPEEYEFAPKKAASHRALDDISESIKELQFYRNNIFKKK
IDEKKRKIIENGENEKTVS

SEQ ID NO: 11

| |
|---|
| ctcaggactc agaggctggg atcatggtag atggaaccct cctttactc ctctcggagg |
| ccctggccct tacccagacc tgggcgggct cccactcctt gaagtatttc cacacttccg |
| tgtcccggcc cggccgcggg gagccccgct tcatctctgt gggctacgtg acgacaccc |
| agttcgtgcg cttcgacaac gacgccgcga gtccgaggat ggtgccgcgg gcgccgtgga |
| tggagcagga ggggtcagag tattgggacc gggagacacg gagcgccagg acaccgcac |
| agattttccg agtgaatctg cggacgctgc gcggctacta caatcagagc gaggccgggt |
| ctcacaccct gcagtggatg catggctgcg agctggggcc cgacgggcgc ttcctccgcg |
| ggtatgaaca gttcgcctac gacggcaagg attatctcac cctgaatgag gacctgcgct |
| cctggaccgc ggtggacacg gcggctcaga tctccgagca aaagtcaaat gatgcctctg |
| aggcggagca ccagagagcc tacctggaag acacatgcgt ggagtggctc cacaaatacc |
| tggagaaggg gaaggagacg ctgcttcacc tggagccccc aaagacacac gtgactcacc |
| accccatctc tgaccatgag gccaccctga ggtgctgggc cctgggcttc taccctgcgg |
| agatcacact gacctggcag caggatgggg agggccatac ccaggacacg gagctcgtgg |
| agaccaggcc tgcaggggat ggaaccttcc agaagtgggc agctgtggtg gtgccttctg |
| gagaggagca gagatacacg tgccatgtgc agcatgaggg gctacccgag cccgtcaccc |
| tgagatggaa gccggcttcc cagcccacca tccccatcgt gggcatcatt gctggcctgg |
| ttctccttgg atctgtggtc tctggagctg tggttgctgc tgtgatatgg aggaagaaga |
| gctcaggtgg aaaaggaggg agctactcta aggctgagtg gagcgacagt gcccaggggt |
| ctgagtctca cagcttgtaa agcctgagac agctgccttg tgtgcgactg agatgcacag |
| ctgccttgtg tgcgactgag atgcaggatt tcctcacgcc tccctatgt gtcttagggg |
| actctggctt ctcttttgc aagggcctct gaatctgtct gtgtccctgt agcacaatg |
| tgaggaggta gagaaacagt ccacctctgt gtctaccatg acccccttcc tcacactgac |

| Gene Sequences |
|---|
| ctgtgttcct tccctgttct cttttctatt aaaaataaga acctgggcag agtgcggcag |
| ctcatgcctg taatcccagc acttagggag gccgaggagg gcagatcacg aggtcaggag |
| atcgaaacca tcctggctaa cacggtgaaa ccccgtctct actaaaaaat acaaaaaatt |
| agctgggcgc agaggcacgg gcctgtagtc ccagctactc aggaggcgga ggcaggagaa |
| tggcgtcaac ccgggaggcg gaggttgcag tgagccagga ttgtgcgact gcactccagc |
| ctgggtgaca gggtgaaacg ccatctcaaa aaataaaaat tgaaaaataa aaaagaacc |
| tggatctcaa tttaattttt catattcttg caatgaaatg gacttgagga agctaagatc |
| atagctagaa atacagataa ttccacagca catctctagc aaatttagcc tattcctatt |
| ctctagccta ttccttacca cctgtaatct tgaccatata ccttggagtt gaatattgtt |
| ttcatactgc tgtggtttga atgttccctc caacactcat gttgagactt aatccctaat |
| gtggcaatac tgaaaggtgg ggcctttgag atgtgattgg atcgtaaggc tgtgccttca |
| ttcatgggtt aatggattaa tgggttatca caggaatggg actggtggct ttataagaag |
| aggaaaagag aactgagcta gcatgcccag cccacagaga gcctccacta gagtgatgct |
| aagtggaaat gtgaggtgca gctgccacag agggcccca ccagggaaat gtctagtgtc |
| tagtggatcc aggccacagg agagagtgcc ttgtggagcg ctgggagcag gacctgacca |
| ccaccaggac cccagaactg tggagtcagt ggcagcatgc agcgccccct tgggaaagct |
| ttaggcacca gcctgcaacc cattcgagca gccacgtagg ctgcacccag caaagccaca |
| ggcacggggc tacctgaggc cttgggggcc caatccctgc tccagtgtgt ccgtgaggca |
| gcacacgaag tcaaaagaga ttattctctt cccacagata cctttctct cccatgaccc |
| tttaacagca tctgcttcat tcccctcacc ttcccaggct gatctgaggt aaactttgaa |
| gtaaaataaa agctgtgttt gagcatca |

SEQ ID NO: 12
MVDGTLLLLLSEALALTQTWAGSHSLKYFHTSVSRPGRGEPRFI
SVGYVDDTQFVRFDNDAASPRMVPRAPWMEQEGSEYWDRETRSARDTAQIFRVNLRTL
RGYYNQSEAGSHTLQWMHGCELGPDGRFLRGYEQFAYDGKDYLTLNEDLRSWTAVDTA
AQISEQKSNDASEAEHQRAYLEDTCVEWLHKYLEKGKETLLHLEPPKTHVTHHPISDH
EATLRCWALGFYPAEITLTWQQDGEGHTQDTELVETRPAGDGTFQKWAAVVVPSGEEQ
RYTCHVQHEGLPEPVTLRWKPASQPTIPIVGIIAGLVLLGSVVSGAVVAAVIWRKKSS
GGKGGSYSKAEWSDSAQGSESHSL

SEQ ID NO: 13
| gcgggcggcg cgagcgaggg gcagaggcga gagacgccgg cggggcgcgg gcgcggcggc |
|---|
| cccggaggat gctgctgagc cccggcactg cctggctgcg agcacatgat ggcgatacgg |
| gagctcaaag tgtgccttct cggggacact ggggttggga atcaagcat cgtgtgtcga |
| tttgtccagg atcactttga ccacaacatc agccctacta ttggggcatc ttttatgacc |
| aaaactgtgc cttgtggaaa tgaacttcac aagttcctca tctgggacac tgctggtcag |
| gaacggtttc attcattggc tcccatgtac tatcgaggct cagctgcagc tgttatcgtg |
| tatgatatta ccaagcagga ttcattttat accttgaaga aatgggtcaa ggagctgaaa |
| gaacatggtc cagaaaacat tgtaatggcc atcgctggaa acaagtgcga cctctcagat |
| attagggagg ttccctgaa ggatgctaag gaatacgctg aatccatagg tgccatcgtg |

-continued

| Gene Sequences |
|---|
| gttgagacaa gtgcaaaaaa tgctattaat atcgaagagc tctttcaagg aatcagccgc |
| cagatcccac ccttggaccc ccatgaaaat ggaaacaatg gaacaatcaa agttgagaag |
| ccaaccatgc aagccagccg ccggtgctgt tgacccaagg gccgtggtcc acggtacttg |
| aagaagccag agcccacatc ctgtgcactg ctgaaggacc ctacgctcgg tggcctggca |
| cctcactttg agaagagtga gcacactggc tttgcatcct ggaagacctg caggggcgg |
| ggcaggaaat gtacctgaaa aggattttag aaaaccctgg gaaacccac cacaccacca |
| caaaatggcc tttagtgtat gaaatgcaca tggaggggat gtagttgcat ttttgctaaa |
| aaaaaaaaaa aacctttaaa aattgttgga tgtgtacaaa agtcttactg ccttattatg |
| tgtatgggat tctaaagtgg cattccactt ggatttcctg tgctacctat ccaaattcca |
| gtaactactt cagtgtcatt gcctttgtta cctaaccaac cttcactgaa aggcaaattt |
| agttcaggag gttagttttt agctagcttt ggaagtaagc ctttatttat tacttttttgg |
| aggaaatcag agaagtgtca atggaccgtc actcagactg agacttgagt tattacagaa |
| gccaggaaaa gtgtattaga aactgttgtc tacaccactt ttaattggtg aacaattttt |
| ctaagttatg gtcatatata cccaaacaaa ccaaatcaaa ctaaattact gcatataatt |
| ttgggattgg gtggcctagt ttgaaagagt gatttaagta atcactatgt aagtggtgag |
| agatgcagga catacacatt attcaagaga ccacctgaca tgcatctcct ccgcaggaat |
| acattcgtcc tctcttagag aagtttaacg cacatagtat tattttacta agagaatatc |
| tcttggtgtc atatctaggg gaagagaatt aactagaatt aaatttaatg tttgaatcta |
| aatcattggg caaacttcta ataataacaa ttaataatag gttacaggaa agccagccag |
| aggaagtgtc agcactttaa aattctagac cccaaaaaac tacaaaatca gaaaaagtat |
| ttttatgttt ctagcttgag gagaagggct ttagggctaa ccagaggtct gaccctagaa |
| tgccaaggaa ctgagaatgg gctccgatga aaaccttcct tttcagattc cctgtctgct |
| caattaaaga tgtttgaatc caaggaagt caaggaagaa aaagcatgga aaggaagaga |
| actgattcct actgaaaatt caaattctat taccattcta actttcataa aaagttggga |
| tcaagaagca gctgatttcc tgccagggct tatattaggg ggtgattctt aaaggacatt |
| aggattggtg ctcagaaatg gttaatcatg ctgtgtgcta gccagggcca gctggtacct |
| tctttgccat gagcattcaa gggacggcta acctttattg acaatctata tcgcaaaagt |
| caggaaagag gttgtgagct gattggatta aagacctggc acttcagtaa ctcagcacgc |
| ttccacttca ctcaacttaa gagagttcat tgacagtgtt aggatgtgaa ggctgggaaa |
| cacttatttt gcttcaagag ttccacttgg ctctcccaaa taggtacctc aaaaactgtt |
| agcaagcggc atttggatgt cttgacaggg gctttgcagg gattttagg gttttttcca |
| cattgtccac attaatggtt ggcatgattg tgcttgcagg ccaagaaatg atcatacccc |
| ttgccaaagg taaaaaaaa aaaaaaaaaa tgagttgaaa attgaagtga cctctttcca |
| gctgagttgc aggcttattt tgtaaccttt cctcatccag ttttccctga gaacctgggt |
| ttatctctag atagctgttc aggtttttta gctgaggggt aagtatccta gctgagagtt |
| ttgcatcttt gggctgggtt tgcagtggtt gtgttttgca taaaatgtct agtctttgcc |
| acagatagtg agctacccac taatgagccc atggttttat ttcagaagca catgagggtg |
| tgaaaccact ctgttacctt tctgtattgt cttagctatt caagccagtc agaggataat |
| atatatattc tcatcagcac tcagagtagt cagtgaagag agtagatcac acttgggcac |

-continued

Gene Sequences accaggattc acataaacat tgtatcttct ctgtggatgc tcaggccttg tctacaatga
ggctttacaa ccttcctttg ttttggctcg ggattacttc ctggctgtct aataattgaa
ccataaccat gtaatattat gtaaaggcct ggaaattact gttgctaaaa aaagtcatgt
agtttcatgt agtgtagcat ccttggcatc gttttccaaa atttgttcct tctccctttt
ttttttcttt cgtgtgtggc atgagtgtgt atctgtgtaa atatgattgt atatgtgtta
ctccgatatg taatccattt cactggctga gtttggcccc tagccatgtg ttaatataaa
gtaggcatgg cttcccaatg gaaatctctg agaatgacag tggagttgtg caagcatttt
acattgccac ataattgact tgccatttta tggttaaaaa cggcacatta ggcagttgaa
tatgacgtta ccttgcagac taaaaggttg aaggcccgaa actaactttt agctaacaat
aagggctgtg ccccaatgga aactgagttc attttctgag aaaggtttgg atgactgaaa
tatttcctct acagtcaagg actttggcat gtggtggctg aaactgagct ttttgtgtg
ggctccagtt ctcactgttc tgcaatgctc atggcaagtt gaatggtgag ctagcttata
aattaaagag ctctgaactg tattcagacc gactgggtat ctagcttact gttttaacat
cattgttgaa accagaccct gtagtccagt ggtgctgccc tgttgtgcaa actgctcctt
tttctcgtgt ttttgtaaag agcttccatc tgggctggac ccagttcttg cacatacaag
acaccgctgc agtcagctag gacctttccg ccatgtattc tattctgtag taaagcattt
ccatcaacaa tgcctaattg tatctgttat ttttggttta acacacactg attcatacta
ataaatattt tcagtttta SEQ ID NO: 14
MMAIRELKVCLLGDTGVGKSSIVCRFVQDHFDHNISPTIGASFM
TKTVPCGNELHKFLIWDTAGQERFHSLAPMYYRGSAAAVIVYDITKQDSFYTLKKWVK
ELKEHGPENIVMAIAGNKCDLSDIREVPLKDAKEYAESIGAIVVETSAKNAINIEELF
QGISRQIPPLDPHENGNNGTIKVEKPTMQASRRCC SEQ ID NO: 15
ctctcaacca tcaggttcgg cagcccgcgg cgccgcctgg cagctcctcc tcttctccgc
cccgccggcc gcgggcgcgg gggacgtcag cgctgccagc gtggaaggag ctgcggggcg
cgggaggagg aagtagagcc cgggaccgcc aggccaccac cggccgcctc agccatggac
gcgtccctgg agaagatagc agaccccacg ttagctgaaa tgggaaaaaa cttgaaggag
gcagtgaaga tgctggagga cagtcagaga agaacagaag aggaaaatgg aaagaagctc
atatccggag atattccagg cccactccag ggcagtgggc aagatatggt gagcatcctc
cagttagttc agaatctcat gcatggagat gaagatgagg agcccagag ccccagaatc
caaaatattg gagaacaagg tcatatggct ttgttgggac atagtctggg agcttatatt
tcaactctgg acaaagagaa gctgagaaaa cttacaacta ggatactttc agataccacc
ttatggctat gcagaatttt cagatatgaa atgggtgtg cttatttcca cgaagaggaa
agagaaggac ttgcaaagat atgtaggctt gccattcatt ctcgatatga agacttcgta
gtggatggct tcaatgtgtt atataacaag aagcctgtca tatatcttag tgctgctgct
agacctggcc tgggccaata ccttttgtaat cagctcggct tgcccttccc ctgcttgtgc
cgtgtacccct gtaacactgt gtttggatcc cagcatcaga tggatgttgc cttcctggag
aaactgatta aagatgatat agagcgagga agactgcccc tgttgcttgt cgcaaatgca -continued

| Gene Sequences |
|---|
| ggaacggcag cagtaggaca cacagacaag attgggagat tgaaagaact ctgtgagcag |
| tatggcatat ggcttcatgt ggagggtgtg aatctggcaa cattggctct gggttatgtc |
| tcctcatcag tgctggctgc agccaaatgt gatagcatga cgatgactcc tggcccgtgg |
| ctgggtttgc cagctgttcc tgcggtgaca ctgtataaac acgatgaccc tgccttgact |
| ttagttgctg gtcttacatc aaataagccc acagacaaac tccgtgccct gcctctgtgg |
| ttatctttac aatacttggg acttgatggg tttgtggaga ggatcaagca tgcctgtcaa |
| ctgagtcaac ggttgcagga aagtttgaag aaagtgaatt acatcaaaat cttggtggaa |
| gatgagctca gctccccagt ggtggtgttc agattttcc aggaattacc aggctcagat |
| ccggtgttta aagccgtccc agtgcccaac atgacacctt caggagtcgg ccgggagagg |
| cactcgtgtg acgcgctgaa tcgctggctg ggagaacagc tgaagcagct ggtgcctgca |
| agcggcctca cagtcatgga tctggaagct gagggcacgt gtttgcggtt cagccctttg |
| atgaccgcag cagttttagg aactcgggga gaggatgtgg atcagctcgt agcctgcata |
| gaaagcaaac tgccagtgct gtgctgtacg ctccagttgc gtgaagagtt caagcaggaa |
| gtggaagcaa cagcaggtct cctatatgtt gatgaccta actggtctgg aatagggagtt |
| gtcaggtatg aacatgctaa tgatgataag agcagtttga aatcagatcc gaaggggaa |
| aacatccatg ctggactcct gaagaagtta atgaactgg aatctgacct aacctttaaa |
| ataggccctg agtataagag catgaagagc tgcctttatg tcggcatggc gagcgacaac |
| gtcgatgctg ctgagctcgt ggagaccatt gcggccacag cccgggagat agaggagaac |
| tcgaggcttc tggaaaacat gacagaagtg gttcggaaag gcattcagga agctcaagtg |
| gagctgcaga aggcaagtga agaacggctt ctggaagagg gggtgttgcg gcagatccct |
| gtagtgggct ccgtgctgaa ttggttttct ccggtccagg ctttacagaa gggaagaact |
| tttaacttga cagcaggctc tctggagtcc acagaaccca tatatgtcta caaagcacaa |
| ggtgcaggag tcacgctgcc tccaacgccc tcgggcagtc gcaccaagca gaggcttcca |
| ggccagaagc ctttttaaaag gtccctgcga ggttcagatg ctttgagtga accagctca |
| gtcagtcaca ttgaagactt agaaaaggtg gagcgcctat ccagtgggcc ggagcagatc |
| accctcgagg ccagcagcac tgagggacac ccaggggctc ccagccctca gcacaccgac |
| cagaccgagg ccttccagaa aggggtccca cacccagaag atgaccactc acaggtagaa |
| ggaccggaga gcttaagatg agactcattg tgtggtttga gactgtactg agtattgttt |
| cagggaagat gaagttctat tggaaatgtg aactgtgcca catactaata taaattactg |
| ttgtttgtgc ttcactggga ttttggcaca aatatgtgcc tgaaaggtag gctttctagg |
| aggggagtca gcttgtctaa cttcatgtac atgtagaacc acgtttgctg tcctactacg |
| acttttccct aagttaccat aaacacattt tattcacaaa aaacacttcg aatttcaagt |
| gtctaccagt agcacccttg ctctttctaa acataagcct aagtatatga ggttgcccgt |
| ggcaactttt tggtaaaaca gcttttcatt agcactctcc aggttctctg caacacttca |
| cagaggcgag actggctgta tcctttgctg tcggtcttta gtacgatcaa gttgcaatat |
| acagtgggac tgctagactt gaaggagagc agtgattgtg ggattgtaaa taagagcatc |
| agaagccctc cccagctact gctcttcgtg gagacttagt aaggactgtg tctacttgag |
| ctgtggcaag gctgctgtct gggactgtcc tctgccacaa ggccatttct cccattatat |
| accgtttgta aagagaaact gtaaagtctc ctcctgacca tatattttta aatactggca |

| Gene Sequences |
|---|
| aagcttttaa aattggcaca caagtacaga ctgtgctcat ttctgtttag tatctgaaaa |
| cctgatagat gctacccta agagcttgct cttccgtgtg ctacgtagca cccacctggt |
| taaaatctga aaacaagtac cccttttgacc tgtctcccac tgaagcttct actgccctgg |
| cagctcgcct gggcccaact cagaaacagg agccagcaga gcactctctc acgctgatcc |
| agccgggcac cctgcttaag tcagtagaag ctcgctggca ctgcccgttc ctactttcc |
| gaagtactgc gtcactttgt cgtaagtaat ggccctgtg ccttcttaat ccagcagtca |
| agcttttggg agacctgaaa tgggaaaat tcacactggg tttctggact gtagtattgg |
| aagccttagt tatagtatat taagcctata attatactct gatttgatgg gattttgac |
| atttacactt gtcaaaatgc aggggttt tttggtgca gatgattaaa cagtcttccc |
| tatttggtgc aatgaagtat agcagataaa atggggggagg ggtaaattat caccttcaag |
| aaaattacat gttttatat atatttggaa ttgttaaatt ggttttgctg aaacatttca |
| cccttgagat attatttgaa tgttggtttc aataaaggtt cttgaaattg ttaccagtga |
| attcagttta taaatcttat tacaaaagac ttacccacgt acctgaaata gctgccgata |
| gaccagtgag aggtaggttc tcctctgccc gttattaccg accaaaaaaa aaactggaca |
| tcaatttttt agtaaaccaa aaaataagtc tcaacaaatg cctttgccaa aataaggttt |
| tattttgaaa gtcatttgat gaaagtcatt tgaaagacac tgaggaggga aggaggccta |
| agacccaaca gatgtaggat ccagatctgg attcgtgcca gccccaccaa tggtctgtca |
| ggccaagaag gtgctttctt tggtaattca tgttttttaa cttcctggag aagagatctt |
| ttcccacaag ccatcttcat ttttttttgta gagtagggct ttatttccag aaaacagtgt |
| gtgagctgga gatgggtgtt tttttaaaaa catcaaggta gatctaatat gttcaacaaa |
| gtggggtggc tcagccagag gcgaagtgga aagattctga aaacacaaga tggtgggcat |
| tagagaagcc aaccttactg tcccctgctg tgataaagat gtcaaagtat ctttgttctt |
| ggacacaaat atatataata aaatacgtta agaaatga |
| SEQ ID NO: 16 |
| MDASLEKIADPTLAEMGKNLKEAVKMLEDSQRRTEEENGKKLIS |
| GDIPGPLQGSGQDMVSILQLVQNLMHGDEDEEPQSPRIQNIGEQGHMALLGHSLGAYI |
| STLDKEKLRKLTTRILSDTTLWLCRIFRYENGCAYFHEEEREGLAKICRLAIHSRYED |
| FVVDGFNVLYNKKPVIYLSAAARPGLGQYLCNQLGLPFPCLCRVPCNTVFGSQHQMDV |
| AFLEKLIKDDIERGRLPLLLVANAGTAAVGHTDKIGRLKELCEQYGIWLHVEGVNLAT |
| LALGYVSSSVLAAAKCDSMTMTPGPWLGLPAVPAVTLYKHDDPALTLVAGLTSNKPTD |
| KLRALPLWLSLQYLGLDGFVERIKHACQLSQRLQESLKKVNYIKILVEDELSSPVVVF |
| RFFQELPGSDPVFKAVPVPNMTPSGVGRERHSCDALNRWLGEQLKQLVPASGLTVMDL |
| EAEGTCLRFSPLMTAAVLGTRGEDVDQLVACIESKLPVLCCTLQLREEFKQEVEATAG |
| LLYVDDPNWSGIGVVRYEHANDDKSSLKSDPEGENIHAGLLKKLNELESDLTFKIGPE |
| YKSMKSCLYVGMASDNVDAAELVETIAATAREIEENSRLLENMTEVVRKGIQEAQVEL |
| QKASEERLLEEGVLRQIPVVGSVLNWFSPVQALQKGRTFNLTAGSLESTEPIYVYKAQ |
| GAGVTLPPTPSGSRTKQRLPGQKPFKRSLRGSDALSETSSVSHIEDLEKVERLSSGPE |
| QITLEASSTEGHPGAPSPQHTDQTEAFQKGVPHPEDDHSQVEGPESLR |

What is claimed is:

1. A method for treating acute rejection (AR) of a transplant in a subject comprising:
   (a) measuring expression levels of each of genes consisting of DIP2C, ENOSF1, FBXO21, KCTD6, PDXDC1, REXO2, HLA-E, and RAB31 in a biological sample from a subject having an organ transplant, wherein differential expression of the genes results in a genetic signature in which DIP2C, ENOSF1, FBXO21, KCTD6, PDXDC1 and REXO2 are downregulated and in which HLA-E and RAB31 are upregulated as compared to control, wherein the genetic signature indicates the subject has an increased likelihood of AR of the organ transplant; and
   (b) administering an effective amount of corticosteroid or antibody therapy to the subject, wherein the antibody is selected from the group consisting of a lymphocyte-depleting antibody, an anti-thymoglobulin antibody, an anti-CD52 antibody, and an anti-CD3 antibody.

2. The method of claim 1, wherein mRNA expression levels are measured.

3. The method of claim 1, wherein protein expression levels are measured.

4. The method of claim 1, wherein the acute rejection is T cell-mediated rejection (TCMR) or antibody-mediated rejection (ABMR).

5. The method of claim 1, wherein the transplant is a kidney transplant.

6. The method of claim 1, wherein the subject is an adult.

7. The method of claim 1, wherein the subject is a pediatric subject.

8. The method of claim 1, further comprising performing a biopsy on transplant tissue from the subject.

9. The method of claim 8, further comprising, if the biopsy shows antibody-mediated damage in the subject, administering plasma exchange therapy, intravenous immunoglobulin (Ig) therapy, anti-interleukin 6 (IL6) therapy, or a proteosomal inhibitor to the subject.

10. The method of claim 9, wherein the intravenous Ig therapy is administered in combination with rituximab.

11. The method of claim 1, wherein the biological sample comprises tissue, cells, proteins, nucleic acids or other cellular matter.

12. The method of claim 1, wherein the biological sample comprises peripheral blood mononuclear cells (PBMCs), plasma, blood, a urine sample containing urinary cells, a sample of bronchoalveolar lavage fluid, a sample of bile, a sample of pleural fluid, a sample of peritoneal fluid, any other fluid secreted or excreted by a normally or abnormally functioning allograft, any other fluid resulting from exudation or transudation through an allograft or in anatomic proximity to an allograft, or any fluid in fluid communication with the allograft.

13. The method of claim 9, wherein the proteosomal inhibitor is administered in combination with rituximab.

14. The method of claim 1, wherein the acute rejection is kidney transplant rejection, acute tubular injury, T cell mediated rejection (TCR), or antibody-mediated rejection (AMR).

* * * * *

SEQUENCE LISTING

<160> NUMBER OF SEQ ID NOS: 112

<210> SEQ ID NO 1
<211> LENGTH: 7885
<212> TYPE: DNA
<213> ORGANISM: Homo sapiens

<400> SEQUENCE: 1

| | | | | | |
|---|---|---|---|---|---|
| ctcggtgcgg | ttccgccggg | cgcgaggagc | cgccgagacc | tccgcctgcg | aacaaagagg | 60 |
| aggccgtgcg | gggcgcggcg | cccgcggagc | atggcggacc | gcagcctgga | gggcatggcg | 120 |
| ctgcccctgg | aggtgcgggc | gcgcctggcc | gagctggagc | tggagctgtc | ggaaggtgac | 180 |
| atcacacaaa | aaggatatga | aaagaagagg | tcaaagttaa | ttggagccta | ccttccgcag | 240 |
| cctccgaggg | tggaccaagc | tttgccgcaa | gaacgccggg | ctcctgtcac | tccttcctcc | 300 |
| gcctctcgct | accaccgccg | acggtcttca | gggtcacgag | atgagcgcta | tcggtcagac | 360 |
| gtccacacgg | aagctgtcca | gcggctctg | gccaaacaca | aagagcggaa | gatggcagtg | 420 |
| cctatgcctt | ccaaacgcag | gtccctggtc | gtgcagacct | cgatggacgc | ctacacccct | 480 |
| ccagatacct | cttctggctc | agaagatgaa | ggctcagtgc | aggggactc | ccagggcacc | 540 |
| cccacctcca | gccagggcag | catcaatatg | gagcactgga | tcagccaggc | catccacggc | 600 |
| tccaccacgt | ccaccacctc | ctcgtcctct | acgcagagcg | ggggcagcgg | ggctgcccac | 660 |
| aggctggcgg | acgtcatggc | tcagacccac | atagaaaatc | attctgcacc | tcctgacgta | 720 |
| accacgtaca | cctcagagca | ctcgatacag | gtggagagac | gcagggttc | cacggggtcc | 780 |
| cggacagcgc | ccaagtacgg | caacgccgag | ctcatggaga | ccggggatgg | agtaccagta | 840 |
| agtagccggg | tgtcagcaaa | aatccagcag | cttgtcaata | ccctcaaacg | accgaaacga | 900 |
| ccaccttac | gagaattctt | tgtcgatgac | tttgaagaat | tattagaagt | tcaacaaccg | 960 |
| gatccgaacc | aaccaaagcc | ggaggggggcc | cagatgctgg | ccatgcgcgg | agagcagctg | 1020 |
| ggcgtggtca | cgaactggcc | gccgtcgctg | gaggccgcac | tgcagaggtg | gggcaccatc | 1080 |
| tcgcccaagg | cgccctgcct | gaccaccatg | gacaccaacg | ggaagcccct | ctacatcctc | 1140 |
| acttacggca | gctgtggac | aagaagtatg | aaggtcgctt | acagcattct | acacaaatta | 1200 |
| ggcacaaagc | aggaacccat | ggtccggcct | ggagataggg | tggcactggt | gttccccaac | 1260 |
| aatgatccgg | ctgccttcat | ggcggctttc | tacggctgcc | tgctggccga | ggtggtcccc | 1320 |
| gtgcccatcg | aggtgccgct | caccaggaag | gacgcaggga | gccagcagat | aggtttcttg | 1380 |
| cttggaagct | gtggagttac | tgtagccttg | actagtgacg | cctgccataa | aggacttcca | 1440 |
| aaaagcccaa | cgggagagat | cccacagttt | aaaggttggc | caaagctgct | gtggtttgtc | 1500 |
| acagagtcta | aacatctctc | caaaccgccc | cgagactggt | tcccacacat | taaagatgcc | 1560 |
| aataacgaca | ctgcgtatat | tgagtacaag | acgtgtaagg | atggcagtgt | gctgggtgtg | 1620 |
| acggtgacga | ggactgcgct | gctgacacac | tgccaggccc | tgacgcaggc | gtgtggctac | 1680 |
| acggaagctg | aaaccattgt | gaatgtgctg | gatttcaaga | aggacgtcgg | gctctggcat | 1740 |
| ggcatcctga | caagcgtcat | gaacatgatg | catgtgatca | gcatcccgta | ctcgctgatg | 1800 |
| aaggtgaacc | tctctcctg | gatccagaag | gtctgccagt | acaaagcaaa | agtggcgtgt | 1860 |
| gtgaaatcga | gggatatgca | ttgggcatta | gtagcacaca | gagatcagag | agacatcaac | 1920 |
| ctctcctctc | tgcgaatgct | gatagtggcg | gacggcgcga | acccctggtc | tatttcttct | 1980 |
| tgcgatgcat | ttctcaatgt | cttccaaagt | aaaggccttc | gacaggaggt | catctgtcct | 2040 |
| tgtgccagct | cgccagaggc | cctcactgtg | gccatccgga | ggcccacgga | tgacagtaac | 2100 |

```
cagcccccgg gccggggtgt cctctccatg catggactga cctatggggt cattcgtgtg    2160
gactcggaag agaagctgtc cgtgctcacc gtgcaggatg tcggcctcgt gatgcctgga    2220
gccatcatgt gttcagtgaa gccagacggg gttcctcagc tgtgcagaac ggatgagatc    2280
ggggagctgt gtgtgtgtgc agttgcgacg ggcacgtcct actatggcct ctctggcatg    2340
accaagaaca cctttgaggt gtttcccatg acaagctccg ggctccgat cagtgaatac     2400 ccattcataa ggacaggctt gctggggttc gtgggtcccg gaggcctcgt cttcgtggtg    2460
ggcaagatgg atggcctcat ggtggtcagc gggcgcaggc acaacgccga cgacatcgtg    2520
gccactgcgc tggccgtaga acccatgaag tttgtctacc ggggaaggat agccgtgttc    2580
tcggtgaccg tgctgcacga cgagaggatc gtgatcgtgg ctgagcagag gcctgactcc    2640
acggaagagg acagtttcca gtggatgagc cgtgtgctgc aggcgattga cagtatacat    2700
caagttggag tttattgcct ggccttggtg ccagcaaaca ccctccccaa aaccccgctt    2760
ggtgggatcc atttatcaga aacaaaacag ctttttctgg agggctctct gcaccccTGC    2820
aatgtcctaa tgtgccccca cacctgcgtc acaaacttgc ctaagcctcg acagaagcag    2880
ccagaaatcg gccctgcctc tgtgatggtg gggaacctgg tctctgggaa gagaatcgcc    2940
caggccagtg gcagagacct gggtcagatc gaagataacg accaggcacg caagttcctg    3000
ttcctctcag aggtcttgca gtggagagca cagaccaccc cggaccacat cctctacacg    3060
ctgctcaact gtcggggtgc gatagcgaac tcgctgacct gcgtgcagct gcacaagaga    3120
gctgagaaga tcgccgtgat gctgatggag aggggccacc ttcaggacgg cgaccacgtg    3180
gccttggtct accccccagg aatagacctg atagcagcgt tttatggttg cctgtacgca    3240
ggctgtgtgc caataaccgt ccgtcccccg cacccacaga acatcgcgac gacgttgcct    3300
accgtcaaga tgattgtgga ggtgagtcgc tctgcctgtc tgatgacgac acagctgatc    3360
tgtaagttgc tgcggtccag ggaggcgcg cggctgtgg acgtcaggac gtggcccctc     3420
atcctggaca cagatgattt gccaaagaag cggcctgccc agatctgcaa accttgcaac    3480
ccagacactc ttgcatatct cgacttcagc gtgtccacaa ctgggatgct agctggcgta    3540
aagatgtctc acgcagccac cagtgccttc tgccgttcca ttaagctgca gtgtgaactt    3600
tacccctcta gagaagtggc catctgcctg gaccccttact gtggactggg atttgtcctc    3660
tggtgcctct gcagtgtgta ttctgggcac cagtccatcc tgatcccgcc ctctgagctg    3720
gaaaccaacc ccgccttgtg gcttcttgcc gtgagtcagt acaaagtccg agacacgttt    3780
tgctcctact ccgtgatgga gctgtgcacc aaggggctgg gctcgcaaac agagtccctc    3840
aaggcgcgag gctggactt gtcccgagtg aggacctgcg tggttgtggc ggaagagagg     3900
cctcggatcg cactcacaca gtcgttctca aagctgttta aggacctggg ccttcacccg    3960
cgggccgtca gcacctcgtt cggttgcagg gtgaacctgg cgatttgctt gcagggaacc    4020
tcaggacctg acccaaccac tgtctacgtg gacatgagag ccctgagaca cgacagagtc    4080
cgcttagtgg aaagaggatc ccctcatagt ctgcccctga tggaatcggg aaagatactt    4140
ccaggggttc ggattataat tgccaaccca gaaacaaaag gaccgctggg ggactcacac    4200
cttgagagga tttgggttca cagtgcccac aatgccagcg ttatttcac tatttacgga     4260 gacgaatccc tccagtcaga tcacttcaac tcaagactaa gttttggaga cacccagacc    4320
atctgggcac gcacaggcta cttggggttc ctgcggagaa ctgagctcac agatgcaaat    4380
ggagagcgcc atgatgccct ctacgtggta ggggcactgg acgaagccat ggagctgcgg    4440
```

-continued

```
ggcatgcggt accacccaat cgacattgag acctcggtca tcagagccca taaaagcgtt      4500
acggaatgtg ctgtgtttac ctggacaaat ttgttggtgg ttgtggttga gctggatggg      4560
tcggaacaag aagccttgga cctggttccc ttggtgacca acgtggtcct ggaggagcac      4620
tacctgatcg tcggagtggt ggtcgtggtg gacatcggcg tcatccccat caactcccgt      4680
ggggagaagc agcgcatgca cctgcgagac gggttttttgg cagaccagct agaccccatc      4740
tatgtggcct acaacatgta gtctcgtctc ttggcttcca tggactttc tagagatgta      4800 gacattgttc tccgtgtcca ctgaagcgtg cagacacagg gcaacactca ccagaataca      4860
gccatttgtg gtgagagtgg aggaggaaga ggaggaggaa gaggacttct cacagcagcc      4920
acgattggca tggggggtgaa atgtgaattt accactgaat ttcgctcaga aggactttgg      4980
attactgcct tcagtttgtt ggaaaagccc atttcaaaac tttcttttct tttcttctt       5040 ttttaattat tggataataa gtgctttctt cgtaaatgtg gtattttgtt aagccgaaat      5100
agcaattaaa aaatatcct gccctccaga tgggttcttt taaacaattt atgtagtgtg      5160
acaaagaatt gttttctctg ttttaatgtg tcatgaaatc ttaatgacat ggatctgtta      5220
ctaatttaag ccattgctag atctcatcct tttaggaaag tttgaggtac gagaaaacct      5280
tccaaatagc accttccaat tagataatag cagcttctt tgtcagaaat gtgctgaaga      5340
aacaaaggct ggtatacggc cttcgaagtt agtatagaat gagaagaaat tataaataag      5400
gtgtatttcg gcaattatct tgcaaatatc tttgtactaa actaaaaaga taaaataagt      5460
taacttcctc aatatgtaat tatgtacaaa acgtttaatt tattttgatc tctttagaac      5520
tataaaagag aaaaacattc aagaatatta agtcttgta atgtttgcta atataaaaaa       5580
gtgttgtatt atcttgcgtg gatagtatca caacaaatat atatatgta aatataaatt       5640 cactaatgaa caaaggagat tttaaagttt aagatgcaga acttgtcact tgcatggtgt      5700 gcccccgta ctcacataca ctctgctgtt gccagcagtc gcagaccgca ggagccctgt       5760
ctaaagtttt cttctagaac cagagaccag caagtgaaat tattgccatc tcaaggatgg      5820
caaaagaatt caaagctcaa tgtgcactat ttttttcttt gctgtgggac aacagtgaat      5880
gtgtttatgc cagcgtgtgc tgatgatact gaggggcttt aggttggcaa atagcactgt      5940
tttcttagct gcaagaattc attgcacaat gttttttcatc atttttgtta atgtcatctt      6000
tttttggtcc ttgctacgaa aaggaatgcg attctgtggt cattcgcact gggttgcatt      6060
gattccccct ctgatggcca atgtggagtg gacaaagtgt ccggaactca tcggtgat       6120 cgtcccctcg tcttaagacc cagcccgctc tgtgtgagcc tctggggctc cctcgctcag      6180
tgagcacagt tccccggggg ttcatgccag agctccggct gaagcaagaa gtcctccagc      6240
tgcgtcgttt gccgcctgtg gacgagtgcg ccccagtttc tgccctggca gctcctggcc      6300
acaccttctc agagctcacc tgtgcacttc taaattgaat tggcccacgg tgtccaacca      6360
agaaggagca tctgcactcc gagaaagatg tgttctgtaa ctgccccagt gtgacccgc       6420 agtggctctc ggtgctagat atgcatgact aagattgatg ctgggcaaaa tgtagatgat      6480
ctttcattat gttgtgggca gcgtcttct ctgcctttgc tatatgcagt cagcagtaag       6540
ccttttgcta aaagagtttt gtttgacttc tgagatccaa ggctgattgt tgttaaaaaa      6600 aaaaaaaaa aaaagtggc acatttaaaa aaatgtgtct gcatatgtgg tgcatccttc       6660
catctccaca aaccatttga ttcttgaaat attgtttgac ctcattgctg tgtgtgaata      6720
tttctccaca tgcttcagat gcacattcct agtctctgct tcctaagggg ggaaccacca      6780
cacattgggg ggaaaaaaga cattttccta cacccacca ccttgttgaa agggaggtag       6840
```

-continued

```
gtttggggct tcaggccagg cactgactat gaaacattag ctgcagtgtg caggacagct    6900
ttgaggtcca gctgaagtca ggaagcaaaa caaatgtaga tgtcacttca aacataattt    6960
caactgtcac cagatcaact ctacattcaa ggagtgtgga cgctgcagtg cagttgtgag    7020
ggcagttagc agccgcctct tctgcatcct gtcaactctg attagttaga gtttaggctc    7080
aaaagagttg gtggactgag attgaaattt ggttgtgcaa agaaaggaa aggagacact     7140 tagtaccacc agtttcagca ataaagaagg gtcattctgt attcaaaatt gtactgtaga    7200
taaatcattc atgagattgt aaaaaatgtt tgtcttgtga ccttgtgctt ttgaagtcag    7260
acaaaaccgt gtaatcaact tgcacaaaaa gagggtacac agtgaacata taaacacaga    7320
cctaatcaaa caggagcaga ttcctcatgg tgcttgttta ttatatatat ttaatcctgc    7380
ttgacacttt acccaaggga gatggtccct tttatcagtt gaatgttagc agcgttattt    7440
cagagtgtgg tgactggtta gagaaactca tgtactcaac cagccacagt ttcaaacaaa    7500
atttttatgt gcaaaggaca gcaaccttct tgtatgttaa accaccagta cgctttgtac    7560
atctgtgata acgcctgttt tatattcaaa tgaacaaata aaagctttta ttttttgttgc   7620 tctgaaaata gcagtttctt aattggtccc ctggaaagat gtctgggaca gctttaatcc    7680
cgggaaggaa gtgactccta cagggaaatg tatctgactc tgtttacata atttgttgca    7740
ttacttagta cagataatca tactttgaaa aatgttaaa ttttgatgtg ggcatttatt     7800
gctaaaaata attcctatgg caacaaatgt tttgtgaaat gttttttta attcttttaa     7860 atatatctaa atatatttgt tcaca                                          7885
```

<210> SEQ ID NO 2
<211> LENGTH: 1556
<212> TYPE: PRT
<213> ORGANISM: Homo sapiens

<400> SEQUENCE: 2

Met Ala Asp Arg Ser Leu Glu Gly Met Ala Leu Pro Leu Glu Val Arg
1               5                   10                  15

Ala Arg Leu Ala Glu Leu Glu Leu Glu Leu Ser Glu Gly Asp Ile Thr
            20                  25                  30

Gln Lys Gly Tyr Glu Lys Lys Arg Ser Lys Leu Ile Gly Ala Tyr Leu
        35                  40                  45

Pro Gln Pro Pro Arg Val Asp Gln Ala Leu Pro Gln Glu Arg Arg Ala
    50                  55                  60

Pro Val Thr Pro Ser Ser Ala Ser Arg Tyr His Arg Arg Ser Ser
65                  70                  75                  80

Gly Ser Arg Asp Glu Arg Tyr Arg Ser Asp Val His Thr Glu Ala Val
                85                  90                  95

Gln Ala Ala Leu Ala Lys His Lys Glu Arg Lys Met Ala Val Pro Met
            100                 105                 110

Pro Ser Lys Arg Arg Ser Leu Val Val Gln Thr Ser Met Asp Ala Tyr
        115                 120                 125

Thr Pro Pro Asp Thr Ser Gly Ser Glu Asp Glu Gly Ser Val Gln
    130                 135                 140

Gly Asp Ser Gln Gly Thr Pro Thr Ser Ser Gln Gly Ser Ile Asn Met
145                 150                 155                 160

Glu His Trp Ile Ser Gln Ala Ile His Gly Ser Thr Thr Ser Thr Thr
                165                 170                 175

```
Ser Ser Ser Ser Thr Gln Ser Gly Gly Ser Gly Ala Ala His Arg Leu
            180                 185                 190

Ala Asp Val Met Ala Gln Thr His Ile Glu Asn His Ser Ala Pro Pro
            195                 200                 205

Asp Val Thr Thr Tyr Thr Ser Glu His Ser Ile Gln Val Glu Arg Pro
        210                 215                 220

Gln Gly Ser Thr Gly Ser Arg Thr Ala Pro Lys Tyr Gly Asn Ala Glu
225                 230                 235                 240

Leu Met Glu Thr Gly Asp Gly Val Pro Val Ser Ser Arg Val Ser Ala
                245                 250                 255

Lys Ile Gln Gln Leu Val Asn Thr Leu Lys Arg Pro Lys Arg Pro Pro
            260                 265                 270

Leu Arg Glu Phe Phe Val Asp Asp Phe Glu Glu Leu Leu Glu Val Gln
            275                 280                 285

Gln Pro Asp Pro Asn Gln Pro Lys Pro Glu Gly Ala Gln Met Leu Ala
        290                 295                 300

Met Arg Gly Glu Gln Leu Gly Val Val Thr Asn Trp Pro Pro Ser Leu
305                 310                 315                 320

Glu Ala Ala Leu Gln Arg Trp Gly Thr Ile Ser Pro Lys Ala Pro Cys
                325                 330                 335

Leu Thr Thr Met Asp Thr Asn Gly Lys Pro Leu Tyr Ile Leu Thr Tyr
            340                 345                 350

Gly Lys Leu Trp Thr Arg Ser Met Lys Val Ala Tyr Ser Ile Leu His
            355                 360                 365

Lys Leu Gly Thr Lys Gln Glu Pro Met Val Arg Pro Gly Asp Arg Val
            370                 375                 380

Ala Leu Val Phe Pro Asn Asn Asp Pro Ala Ala Phe Met Ala Ala Phe
385                 390                 395                 400

Tyr Gly Cys Leu Leu Ala Glu Val Val Pro Val Pro Ile Glu Val Pro
                405                 410                 415

Leu Thr Arg Lys Asp Ala Gly Ser Gln Gln Ile Gly Phe Leu Leu Gly
            420                 425                 430

Ser Cys Gly Val Thr Val Ala Leu Thr Ser Asp Ala Cys His Lys Gly
            435                 440                 445

Leu Pro Lys Ser Pro Thr Gly Glu Ile Pro Gln Phe Lys Gly Trp Pro
        450                 455                 460

Lys Leu Leu Trp Phe Val Thr Glu Ser Lys His Leu Ser Lys Pro Pro
465                 470                 475                 480

Arg Asp Trp Phe Pro His Ile Lys Asp Ala Asn Asn Asp Thr Ala Tyr
                485                 490                 495

Ile Glu Tyr Lys Thr Cys Lys Asp Gly Ser Val Leu Gly Val Thr Val
            500                 505                 510

Thr Arg Thr Ala Leu Leu Thr His Cys Gln Ala Leu Thr Gln Ala Cys
            515                 520                 525

Gly Tyr Thr Glu Ala Glu Thr Ile Val Asn Val Leu Asp Phe Lys Lys
        530                 535                 540

Asp Val Gly Leu Trp His Gly Ile Leu Thr Ser Val Met Asn Met Met
545                 550                 555                 560

His Val Ile Ser Ile Pro Tyr Ser Leu Met Lys Val Asn Pro Leu Ser
                565                 570                 575

Trp Ile Gln Lys Val Cys Gln Tyr Lys Ala Lys Val Ala Cys Val Lys
            580                 585                 590
```

-continued

Ser Arg Asp Met His Trp Ala Leu Val Ala His Arg Asp Gln Arg Asp
    595                 600                 605

Ile Asn Leu Ser Ser Leu Arg Met Leu Ile Val Ala Asp Gly Ala Asn
    610                 615                 620

Pro Trp Ser Ile Ser Ser Cys Asp Ala Phe Leu Asn Val Phe Gln Ser
625                 630                 635                 640

Lys Gly Leu Arg Gln Glu Val Ile Cys Pro Cys Ala Ser Ser Pro Glu
                645                 650                 655

Ala Leu Thr Val Ala Ile Arg Arg Pro Thr Asp Ser Asn Gln Pro
                660                 665                 670

Pro Gly Arg Gly Val Leu Ser Met His Gly Leu Thr Tyr Gly Val Ile
            675                 680                 685

Arg Val Asp Ser Glu Glu Lys Leu Ser Val Leu Thr Val Gln Asp Val
        690                 695                 700

Gly Leu Val Met Pro Gly Ala Ile Met Cys Ser Val Lys Pro Asp Gly
705                 710                 715                 720

Val Pro Gln Leu Cys Arg Thr Asp Glu Ile Gly Glu Leu Cys Val Cys
                725                 730                 735

Ala Val Ala Thr Gly Thr Ser Tyr Tyr Gly Leu Ser Gly Met Thr Lys
                740                 745                 750

Asn Thr Phe Glu Val Phe Pro Met Thr Ser Ser Gly Ala Pro Ile Ser
            755                 760                 765

Glu Tyr Pro Phe Ile Arg Thr Gly Leu Leu Gly Phe Val Gly Pro Gly
        770                 775                 780

Gly Leu Val Phe Val Val Gly Lys Met Asp Gly Leu Met Val Val Ser
785                 790                 795                 800

Gly Arg Arg His Asn Ala Asp Asp Ile Val Ala Thr Ala Leu Ala Val
                805                 810                 815

Glu Pro Met Lys Phe Val Tyr Arg Gly Arg Ile Ala Val Phe Ser Val
                820                 825                 830

Thr Val Leu His Asp Glu Arg Ile Val Ile Ala Glu Gln Arg Pro
            835                 840                 845

Asp Ser Thr Glu Glu Asp Ser Phe Gln Trp Met Ser Arg Val Leu Gln
        850                 855                 860

Ala Ile Asp Ser Ile His Gln Val Gly Val Tyr Cys Leu Ala Leu Val
865                 870                 875                 880

Pro Ala Asn Thr Leu Pro Lys Thr Pro Leu Gly Gly Ile His Leu Ser
                885                 890                 895

Glu Thr Lys Gln Leu Phe Leu Glu Gly Ser Leu His Pro Cys Asn Val
                900                 905                 910

Leu Met Cys Pro His Thr Cys Val Thr Asn Leu Pro Lys Pro Arg Gln
            915                 920                 925

Lys Gln Pro Glu Ile Gly Pro Ala Ser Val Met Val Gly Asn Leu Val
        930                 935                 940

Ser Gly Lys Arg Ile Ala Gln Ala Ser Gly Arg Asp Leu Gly Gln Ile
945                 950                 955                 960

Glu Asp Asn Asp Gln Ala Arg Lys Phe Leu Phe Leu Ser Glu Val Leu
                965                 970                 975

Gln Trp Arg Ala Gln Thr Thr Pro Asp His Ile Leu Tyr Thr Leu Leu
                980                 985                 990

Asn Cys Arg Gly Ala Ile Ala Asn Ser Leu Thr Cys Val Gln Leu His
            995                 1000                1005

```
Lys Arg Ala Glu Lys Ile Ala Val Met Leu Met Glu Arg Gly His
    1010            1015            1020

Leu Gln Asp Gly Asp His Val Ala Leu Val Tyr Pro Pro Gly Ile
    1025            1030            1035

Asp Leu Ile Ala Ala Phe Tyr Gly Cys Leu Tyr Ala Gly Cys Val
    1040            1045            1050

Pro Ile Thr Val Arg Pro Pro His Pro Gln Asn Ile Ala Thr Thr
    1055            1060            1065

Leu Pro Thr Val Lys Met Ile Val Glu Val Ser Arg Ser Ala Cys
    1070            1075            1080

Leu Met Thr Thr Gln Leu Ile Cys Lys Leu Leu Arg Ser Arg Glu
    1085            1090            1095

Ala Ala Ala Ala Val Asp Val Arg Thr Trp Pro Leu Ile Leu Asp
    1100            1105            1110

Thr Asp Asp Leu Pro Lys Lys Arg Pro Ala Gln Ile Cys Lys Pro
    1115            1120            1125

Cys Asn Pro Asp Thr Leu Ala Tyr Leu Asp Phe Ser Val Ser Thr
    1130            1135            1140

Thr Gly Met Leu Ala Gly Val Lys Met Ser His Ala Ala Thr Ser
    1145            1150            1155

Ala Phe Cys Arg Ser Ile Lys Leu Gln Cys Glu Leu Tyr Pro Ser
    1160            1165            1170

Arg Glu Val Ala Ile Cys Leu Asp Pro Tyr Cys Gly Leu Gly Phe
    1175            1180            1185

Val Leu Trp Cys Leu Cys Ser Val Tyr Ser Gly His Gln Ser Ile
    1190            1195            1200

Leu Ile Pro Pro Ser Glu Leu Glu Thr Asn Pro Ala Leu Trp Leu
    1205            1210            1215

Leu Ala Val Ser Gln Tyr Lys Val Arg Asp Thr Phe Cys Ser Tyr
    1220            1225            1230

Ser Val Met Glu Leu Cys Thr Lys Gly Leu Gly Ser Gln Thr Glu
    1235            1240            1245

Ser Leu Lys Ala Arg Gly Leu Asp Leu Ser Arg Val Arg Thr Cys
    1250            1255            1260

Val Val Val Ala Glu Glu Arg Pro Arg Ile Ala Leu Thr Gln Ser
    1265            1270            1275

Phe Ser Lys Leu Phe Lys Asp Leu Gly Leu His Pro Arg Ala Val
    1280            1285            1290

Ser Thr Ser Phe Gly Cys Arg Val Asn Leu Ala Ile Cys Leu Gln
    1295            1300            1305

Gly Thr Ser Gly Pro Asp Pro Thr Thr Val Tyr Val Asp Met Arg
    1310            1315            1320

Ala Leu Arg His Asp Arg Val Arg Leu Val Glu Arg Gly Ser Pro
    1325            1330            1335

His Ser Leu Pro Leu Met Glu Ser Gly Lys Ile Leu Pro Gly Val
    1340            1345            1350

Arg Ile Ile Ile Ala Asn Pro Glu Thr Lys Gly Pro Leu Gly Asp
    1355            1360            1365

Ser His Leu Gly Glu Ile Trp Val His Ser Ala His Asn Ala Ser
    1370            1375            1380

Gly Tyr Phe Thr Ile Tyr Gly Asp Glu Ser Leu Gln Ser Asp His
    1385            1390            1395
```

```
Phe Asn Ser Arg Leu Ser Phe Gly Asp Thr Gln Thr Ile Trp Ala
        1400                1405                1410

Arg Thr Gly Tyr Leu Gly Phe Leu Arg Arg Thr Glu Leu Thr Asp
    1415                1420                1425

Ala Asn Gly Glu Arg His Asp Ala Leu Tyr Val Val Gly Ala Leu
    1430                1435                1440

Asp Glu Ala Met Glu Leu Arg Gly Met Arg Tyr His Pro Ile Asp
    1445                1450                1455

Ile Glu Thr Ser Val Ile Arg Ala His Lys Ser Val Thr Glu Cys
    1460                1465                1470

Ala Val Phe Thr Trp Thr Asn Leu Leu Val Val Val Glu Leu
    1475                1480                1485

Asp Gly Ser Glu Gln Glu Ala Leu Asp Leu Val Pro Leu Val Thr
    1490                1495                1500

Asn Val Val Leu Glu Glu His Tyr Leu Ile Val Gly Val Val Val
    1505                1510                1515

Val Val Asp Ile Gly Val Ile Pro Ile Asn Ser Arg Gly Glu Lys
    1520                1525                1530

Gln Arg Met His Leu Arg Asp Gly Phe Leu Ala Asp Gln Leu Asp
    1535                1540                1545

Pro Ile Tyr Val Ala Tyr Asn Met
    1550                1555
```

<210> SEQ ID NO 3
<211> LENGTH: 5362
<212> TYPE: DNA
<213> ORGANISM: Homo sapiens

<400> SEQUENCE: 3

```
agtcctgacc gcacgggggc cgcggccacg gggcgcaggg gccatggtgc gcggcaggat    60
ctcccggctc tcggtccggg acgtgcgctt ccccacgtcg cttggggggcc acggcgcgga   120
cgccatgcac acggaccctg actactcggc tgcctatgtc gtcatagaaa ctgatgcaga   180
agatggaatc aagggtgtg gaattaccct cactctggga aaaggcactg aagttgttgt    240
ctgtgctgtg aatgccctcg cccaccatgt gctcaacaag acctcaagg acattgttgg    300
tgacttcaga ggcttctata ggcagctcac aagtgatggg cagctcagat ggattggtcc    360
agaaaagggc gtggtgcacc tggcgacagc ggccgtccta aacgcggtgt gggacttgtg    420
ggccaagcag gagggaaagc ctgtctggaa gttacttgtg acatggatcc caggatgct    480
ggtatcctgc atagatttca ggtacatcac tgatgtcctg actgaggagg atgccctaga   540
aatactgcag aaaggtcaaa ttggtaaaaa agaaagagag aagcaaatgc tggcacaagg   600
ataccctgct tacacgacat cgtgcgcctg gctggggtac tcagatgaca cgttgaagca   660
gctctgtgcc caggcgctga aggatggctg accaggtttt aaagtaaagg tgggtgctga   720
tctccaggat gacatgcgaa gatgccaaat catccgagac atgattggac cggaaaagac   780
tttgatgatg gatgccaacc agcgctggga tgtgcctgag gcggtggagt ggatgtccaa   840
gctggccaag ttcaagccat gtgattga ggagccaacc tccctgatg acattctggg    900
gcacgccacc atttccaagg cactggtccc attaggaatt ggcattgcca caggagaaca    960
gtgccacaat agagtgatat ttaagcaact cctacaggcg aaggccctgc agttcctcca  1020
gattgacagt tgcagactgg gcagtgtcaa tgagaacctc tcagtattgc tgatggccaa  1080
aaagtttgaa attcctgttt gcccccatgc tggtggagtt ggcctctgtg aactggtgca  1140
```

```
gcacctgatt atatttgact acatatcagt ttctgcaagc cttgaaaata gggtgtgtga    1200
gtatgttgac cacctgcatg agcatttcaa gtatcccgtg atgatccagc gggcttccta    1260
catgcctccc aaggatcccg gctactcaac agaaatgaag gaggaatctg taaagaaaca    1320
ccagtatcca gatggtgaag tttggaagaa actccttcct gctcaagaaa attaagtgct    1380
cagccccaac aacttttttc tttctgaagt gaaagggctt aaaatttctt ggaaatagtt    1440
ttacaaaaat ggatttaaaa aatcctaccg atcaagatga gttcagctag aagtcatacc    1500
accctcagga atcagctaag taattattac ttgattcttt tagcaaatca atgcacgtta    1560
tcctacttaa tccttaaata agtttagatt taactaaccc aaagtccagg aggatgttct    1620
tacaaaaata gctatatcaa gggctggcac ctagacatta aactgtaatt tgaaaataag    1680
caacatgttg cataacttgt tggaataatt ccttgttctg tttaacactt gtcataaatt    1740
agcagaataa aaatagtcgt gcaacaccgg gggtatctgg tatgcaacga agggaaaaat    1800
atttcactga ttaccccgga agtggttttg catcttttcc ttgcttaatc taagcatatt    1860
attagagaag tcacaccatg ctgaagctaa tgagggcaaa atggtagtcc atagattatt    1920 ttaaataac cctttaaggt tataaaagtt taaaaaaaaa aaaaaaaaac tctatcctaa    1980
atggtcatta tattttgagg ataagatgca gttaaaatga gaaaaatagg gcaaaatata    2040
ttcactatta tttctaaaat atactctttt aagtagcatc caaaccagaa tacagcacat    2100
gtttacttaa ggagagttct ttaatctatt ttaggaagga actgagcaga taagtggcag    2160
tacagaatga acaaagcgtg gacgaatgca gaacacttct ttattatagc aacatataaa    2220
acaactataa ctttaaagtt cataaccaca ctctacatca tgatcgatgg tgttactcag    2280
ctccctcaga tttgagggaa tagcttgtga aattcttaaa atattctaaa aatattccaa    2340
aaatagcttg tgaaattcac caaccttctt tataagtacg tgggattgaa atgcacatac    2400 atgttttttgc taagagcaca tacatttcat tctcctcact ttgttcataa cctcagcatt    2460
gtcagatacc ctcagtgagt taactcaaag ccttttatta tggaaagaac tggcacagtt    2520
acatttgcca gtggcaacat ccttaaaaat taataactga taggtcacgg acagattttt    2580
gacctagttc cttttttcttt tagagcaaaa agaactttta cctcggcatc cagcccaacc    2640
cctaaagact gacaatatcc ttcgagctcc tttgaaagca ccctaaacag ccatttccat    2700
tttaatagtt ggatgcggat tgtacccttc aatctgaaag tcttcagctt tgaagtcatc    2760
aattttctca acttttcgaa gaatcctgag ctttgggaaa ggtctgggtt ctcgctgaag    2820
ctaaaaacaa aataaggcca ttattttgcc ataattgtac gacctgttgt aattgctcct    2880
catgtccgtg aaacaagtac acaggatgtg atcaacaaag ttctatttta caggagtatg    2940
atcctgtcga taccttgccg taggttatgt aacatgattg gagcgcaacc agctgttctc    3000
ttgcacagat cgagagtgag gggtattttg tgacattaca cagcatcagg agcctggtgc    3060
ctcatcaggt gtaagttctt ataaccactc ttggcaaatt tattaaagac aggaacacag    3120
tcaatctgta actcatagta gctctacgtt tacttgaatt ccacaatccc taacccatct    3180
gtccctggca gaaagaagga agatgacat gcatggacag tgaacagaaa gggatgaaag    3240
ccaggattcc tgggatgaac agacagtggc aattaggatg tgaagacagg tcacaaccta    3300
ttactatgtc taaaaacgac cagagcagag agccagagag aataagcctg aagtcacctc    3360
cactcaaaag cagccaaact ccctcaaagg agtaacttt aaaacctgga tctaacctgg    3420
aaggggctaa aaagtgtctg gttctgagtt ttttccctta aggctcatga agcagatgaa    3480
cttacatttt tattgccatt tcatatcaat tgttggctgc tataacttag ggatttcaac    3540
```

-continued

```
agactttga agtttggacc taaatattgt acttaatgta aaattaacaa aaaatattta    3600
tggccagggt ggtggcttat gcctgtaatt ccagaatttt cggaggctga ggcaggtgga    3660
tcacttgaag tcaggagttt gagactagcc tggccaacat gatgaaaccc catctctact    3720
aataatacaa aaattagctg ggtgtggtgg catgtgcctg taatcccagc tacctgggag    3780
gctgaggcag aagaattgct tgaacccggg aggtggaggt tgcagtgagc tgagatcgca    3840
ccacggcaca ctccagcctg gccgacagag aaagactcca tctcaaaaaa aaagaaaag    3900
gaaaaacatt tgcacttcaa ttctccttca agttaaaatg agttaaaatg ccccctttg    3960
gacaatcccc tggcttgaat gtggctcttc cctctctggt actggtgctt agtacctcac    4020
agcacctgac atgttaagtg cccatggttg ctgaggcaga tgcctgcctt gtcctgccca    4080
cctgcccacc acttctccct aaactgaagc cccacatttg gagcagtcat ctttatcttg    4140
gacacagcat tgagcagatg cctgttccac agtcaacctt ttatcaagag aaggtaccaa    4200
acccaaaagt ataacatcta attcttacct gaattttcag tggctcgatg tgattcaggt    4260
aaatatgtgc atctcccaaa gtgtgtataa agtcacctgg ctataaaccc gggggagaaa    4320
gcagaacagt atgttagttt caattcttta aaacatcatt taaaaacatt agaatatgca    4380
gacaccgcaa ggcttttttt aaaaaaataa tttagtgtag cttttccatt tttttgtagc    4440
aacagcatct tgttatgttg cccaggctgg tattgaactc cagacctcaa gcaattgctc    4500
ctgtctcagt ctcccaaagt gctgggatta caggcatgag ccaccatacc caacctcagc    4560
atagcttttg agaaaatcca tagaagctgt atcacaaaca acctgtatag atctgttagt    4620
gcgtatacca cagggccaga aaaccttcca gaagaggaag gtttcaaagt aaaagctggt    4680
tcatttctta cttacacata tcaaatttaa aagctaatca gagactaaac tctgcaattt    4740
gttttcccat attaaagaac tgaagagctc agtgtggtag gctggcaagt cacccttccc    4800
gagacagccc accttcaggc ccgtgatgtg cgcaatcatg tacgtgagca gggcgtagct    4860
ggcgatgttg aaaggcacac cgaggcccat gtctcccgat ctctggtaca gctggcagga    4920
cagctcactg ttcaccacat agaactggca gagggcatgg catggaggca gcgccatcag    4980
aggaagatct gaggaaccag cagaggaaga taaggaggga tggtggtttg aaagaccaca    5040
gctaaaggca aagtaaaaca ggagagaaac agaagccaac tcatatggtg gagaccagga    5100
gagagagcca ctgggctgca gtgatgtcca taacagcctc tgcagcgatg cacggagct    5160
gagggagact atccatcggt gcaaggtttc tgcaggtgtc catttacggc tgaagcaatg    5220
ctcttccatc agagctgaag ggatctgggc tacctcgtgg caccagatta caaatacagc    5280
aggaataatt ctgtttgcca caggaaactg gtgcttctgg tacaccctcc tatattaaaa    5340
gtctctatta catggccagg ca                                             5362
```

<210> SEQ ID NO 4
<211> LENGTH: 443
<212> TYPE: PRT
<213> ORGANISM: Homo sapiens

<400> SEQUENCE: 4

Met Val Arg Gly Arg Ile Ser Arg Leu Ser Val Arg Asp Val Arg Phe
1               5                   10                  15

Pro Thr Ser Leu Gly Gly His Gly Ala Asp Ala Met His Thr Asp Pro
            20                  25                  30

Asp Tyr Ser Ala Ala Tyr Val Val Ile Glu Thr Asp Ala Glu Asp Gly
        35                  40                  45

```
Ile Lys Gly Cys Gly Ile Thr Phe Thr Leu Gly Lys Gly Thr Glu Val
 50                  55                  60

Val Val Cys Ala Val Asn Ala Leu Ala His His Val Leu Asn Lys Asp
 65                  70                  75                  80

Leu Lys Asp Ile Val Gly Asp Phe Arg Gly Phe Tyr Arg Gln Leu Thr
                 85                  90                  95

Ser Asp Gly Gln Leu Arg Trp Ile Gly Pro Glu Lys Gly Val Val His
                100                 105                 110

Leu Ala Thr Ala Ala Val Leu Asn Ala Val Trp Asp Leu Trp Ala Lys
            115                 120                 125

Gln Glu Gly Lys Pro Val Trp Lys Leu Leu Val Asp Met Asp Pro Arg
130                 135                 140

Met Leu Val Ser Cys Ile Asp Phe Arg Tyr Ile Thr Asp Val Leu Thr
145                 150                 155                 160

Glu Glu Asp Ala Leu Glu Ile Leu Gln Lys Gly Gln Ile Gly Lys Lys
                165                 170                 175

Glu Arg Glu Lys Gln Met Leu Ala Gln Gly Tyr Pro Ala Tyr Thr Thr
                180                 185                 190

Ser Cys Ala Trp Leu Gly Tyr Ser Asp Thr Leu Lys Gln Leu Cys
            195                 200                 205

Ala Gln Ala Leu Lys Asp Gly Trp Thr Arg Phe Lys Val Lys Val Gly
210                 215                 220

Ala Asp Leu Gln Asp Asp Met Arg Arg Cys Gln Ile Ile Arg Asp Met
225                 230                 235                 240

Ile Gly Pro Glu Lys Thr Leu Met Met Asp Ala Asn Gln Arg Trp Asp
                245                 250                 255

Val Pro Glu Ala Val Glu Trp Met Ser Lys Leu Ala Lys Phe Lys Pro
                260                 265                 270

Leu Trp Ile Glu Glu Pro Thr Ser Pro Asp Asp Ile Leu Gly His Ala
                275                 280                 285

Thr Ile Ser Lys Ala Leu Val Pro Leu Gly Ile Gly Ile Ala Thr Gly
290                 295                 300

Glu Gln Cys His Asn Arg Val Ile Phe Lys Gln Leu Leu Gln Ala Lys
305                 310                 315                 320

Ala Leu Gln Phe Leu Gln Ile Asp Ser Cys Arg Leu Gly Ser Val Asn
                325                 330                 335

Glu Asn Leu Ser Val Leu Leu Met Ala Lys Lys Phe Glu Ile Pro Val
                340                 345                 350

Cys Pro His Ala Gly Gly Val Gly Leu Cys Glu Leu Val Gln His Leu
            355                 360                 365

Ile Ile Phe Asp Tyr Ile Ser Val Ser Ala Ser Leu Glu Asn Arg Val
            370                 375                 380

Cys Glu Tyr Val Asp His Leu His Glu His Phe Lys Tyr Pro Val Met
385                 390                 395                 400

Ile Gln Arg Ala Ser Tyr Met Pro Pro Lys Asp Pro Gly Tyr Ser Thr
                405                 410                 415

Glu Met Lys Glu Glu Ser Val Lys Lys His Gln Tyr Pro Asp Gly Glu
                420                 425                 430

Val Trp Lys Lys Leu Leu Pro Ala Gln Glu Asn
            435                 440

<210> SEQ ID NO 5
<211> LENGTH: 5997
```

<212> TYPE: DNA
<213> ORGANISM: Homo sapiens

<400> SEQUENCE: 5

```
ggtacgcgga caagatggcg gcggcagcag tcgacagcgc gatggaggtg gtgccggcgc    60
tggcggagga ggccgcgccg gaggtagcgg gcctcagctg cctcgtcaac ctgccgggtg   120
aggtgctgga gtacatcctg tgctgcggct cgctgacggc cgccgacatc ggccgtgtct   180
ccagcacctg ccggcggctg cgcgagctgt gccagagcag cggaaggtg tggaaggagc    240
agttccgggt gaggtggcct tcccttatga acactacag ccccaccgac tacgtcaatt    300
ggttggaaga gtataaagtt cggcaaaaag ctgggttaga agcgcggaag attgtagcct   360
cgttctcaaa gaggttcttt tcagagcacg ttccttgtaa tggcttcagt gacattgaga   420
accttgaagg accagagatt ttttttgagg atgaactggt gtgtatccta aatatggaag   480
gaagaaaagc tttgacctgg aaatactacg caaaaaaat tctttactac ctgcggcaac    540
agaagatctt aaataatctt aaggcctttc ttcagcagcc agatgactat gagtcgtatc   600
ttgaaggtgc tgtatatatt gaccagtact gcaatcctct ctccgacatc agcctcaaag   660
acatccaggc ccaaattgac agcatcgtgg agcttgtttg caaaacccct cggggcataa   720
acagtcgcca ccccagcttg gccttcaagg caggtgaatc atccatgata atggaaatag   780
aactccagag ccaggtgctg gatgccatga actatgtcct ttacgaccaa ctgaagttca   840
agggaatcg aatggattac tataatgccc tcaacttata tatgcatcag gtttttgattc   900
gcagaacagg aatcccaatc agcatgtctc tgctctattt gacaattgct cggcagttgg   960
gagtcccact ggagcctgtc aacttcccaa gtcacttctt attaaggtgg tgccaaggcg  1020
cagaagggc gaccctggac atctttgact acatctacat agatgctttt gggaaaggca  1080
agcagctgac agtgaaagaa tgcgagtact tgatcggcca gcacgtgact gcagcactgt   1140
atggggtggt caatgtcaag aaggtgttac agagaatggt gggaaacctg ttaagcctgg  1200
ggaagcggga aggcatcgac cagtcatacc agctcctgag agactcgctg atctctatc   1260
tggcaatgta cccggaccag gtgcagcttc tcctcctcca agccaggctt tacttccacc  1320
tgggaatctg gccagagaag tctttctgtc ttgttttgaa ggtgcttgac atcctccagc  1380
acatccaaac cctagacccg gggcagcacg gggcggtggg ctacctggtg cagcacactc  1440
tagagcacat tgagcgcaaa aaggaggagg tgggcgtaga ggtgaagctg cgctccgatg  1500
agaagcacag agatgtctgc tactccatcg ggctcattat gaagcataag aggtatggct  1560
ataactgtgt gatctacggc tgggacccca cctgcatgat gggacacgag tggatccgga  1620
acatgaacgt ccacagcctg ccgcacggcc accagccc tttctataac gtgctggtgg     1680
aggacggctc ctgtcgatac gcagcccaag aaaacttgga atataacgtg gagcctcaag   1740
aaatctcaca ccctgacgtg ggacgctatt tctcagagtt tactggcact cactacatcc   1800
caaacgcaga gctggagatc cggtatccag aagatctgga gtttgtctat gaaacggtgc   1860
agaatattta cagtgcaaag aaagagaaca tagatgagta aagtctagag aggacattgc   1920
acctttgctg ctgctgctat cttccaagag aacgggactc cggaagaaga cgtctccacg   1980
gagccctcgg gacctgctgc accaggaaag ccactccacc agtagtgctg gttgcctcct  2040
actaagttta ataccgtgt gctcttcccc agctgcaaag acaatgttgc tctccgccta   2100
cactagtgaa ttaatctgaa aggcactgtg tcagtggcat ggcttgtatg cttgtcctgt   2160
ggtgacagtt tgtgacattc tgtcttcatg aggtctcaca gtcgacgctc ctgtaatcat   2220
```

```
tctttgtatt cactccattc ccctgtctgt ctgcatttgt ctcagaacat ttccttggct    2280
ggacagatgg ggttatgcat ttgcaataat ttccttctga tttctctgtg aacgtgttc    2340 ggtcccgagt gaggactgtg tgtcttttta ccctgaagtt agttgcatat tcagaggtaa    2400
agttgtgtgc tatcttggca gcatcttaga gatggagaca ttaacaagct aatggtaatt    2460
agaatcattt gaatttattt ttttctaata tgtgaaacac agatttcaag tgttttatct    2520 tttttttta aatttaaatg ggaatataac acagttttcc cttccatatt cctctcttga    2580
gtttatgcac atctctataa atcattagtt ttctatttta ttacataaaa ttcttttaga    2640
aaatgcaaat agtgaacttt gtgaatggat ttttccatac tcatctacaa ttcctccatt    2700
ttaaatgact acttttattt tttaatttaa aaaatctact tcagtatcat gagtaggtct    2760
tacatcagtg atgggttctt tttgtagtga gacatacaaa tctgatgtta atgtttgctc    2820
ttagaagtca tactccatgg tcttcaaaga ccaaaaaatg aggttttgct tttgtaatca    2880
ggaaaaaaaa aaattaatga accttaaaaa aaaaaaaaaa ggttttgaag ggaaaaaaag    2940
tggtttcaca cctcttgtta ttccttagag tcacttcaag gcctgtttga atgtggcagg    3000
ttagaaagag agagaatgtc tttcatttga agagtgttgg acttgtgtga aaggagatgt    3060
gcgtgttgga atctgctttt ccaagccgcc agggtcctga cggcagcagg acgaagcctg    3120
ttgtggcgtc ttctgggaaa gcctgaccgt gtgttcggac ggcactggct cctttccgaa    3180
gttctcagta actgagccca gagtaactgc acgcctttgt gcagctctgg agctccacca    3240
actctcggcc tgccagttct caagcgagct aatcttgtca ttaatcgata gaagctaact    3300
tccgaagtta ggacctagtt actttgctct caacatttaa aataatgcag ttgctctagt    3360
gaatggggcg ttaggggcct gtctctgcac ctgtctgtcc atctgcatgc agtattctca    3420
cccatgttga atgcctgctg cttgtttacc ctttggaaac cctggggtga ccaaggtttg    3480
gaaagccacc tgagaccact tcatagcaag ggaaggcttt aagcagttac tagaaagaga    3540
tggggatttg gccctggct cctccagcct gaatgagcta tttaatccac tgtccatgtt    3600
cctcatcagt caaatccaaa gtcaaggat ttgaacctgc atctggaaac gtaaccactc    3660
acagcacctg gcccgccaag gttggggagga ttgtacacta ctttcattta aaggggaaag    3720
tttgataata cggaattaat taatatgaat gagatgcatt aataagaacc tgagcatgct    3780
gagagttgca attgttggtt ttctggtttg attgatttcc tttttctta gacacatcaa    3840 agtcaagaaa gatggtttta cctttactga cccagctgta catatgtatc tagactgttt    3900
ttaaatgtct ttcttcatga atgcttcatg gggctccagg aagcctgtat cacctgtgta    3960
agttggtatt tgggcacttt atattttct aaaaacgtgt tttggatcct gtactctaat    4020
aaatcataag tttcttttta aaattttcc aaaacttttc tccatttaa aaagccctgt    4080 tataaacgtt gaactttcac aatgttaaaa tgttaaatat ttggatatag caacttcttt    4140
tctcttcaaa tgaatgccaa gatttttttg tacaatgatt aataaatgga acttatccag    4200
agaaaccacg caaatggcct gcccaatttc gtttgaggac agaaagccca gccatgactt    4260
gagtagaatg tctctcacct ctcttcggat ctaaatatga aaagtatgtt ctgctgaatt    4320
tttctgagca ttggtgagcg gacagcctac ctgtaaacca tgacctcctt gccaaacgtt    4380
aattttatca gctcactagt aacctttgag aattatctgg ttgtcatgca aagattgcac    4440
tttctgaatt atgttaaaac acatgttgta aaatgagaac tgctcatgct ttgaaagaaa    4500
accaggttct tcgtgcgttc tgttgccgtt gatttgaatg gctgtgctgt atacgatgtg    4560
tccagaatgt cttcagagca ctgtttccgt gtgatgttac tacctactat gtgggaggaa    4620
```

-continued

```
aaaaggttat aggttaaaca aagtcaattg actctatggt ggtgtttctc aatacctgtg   4680
acgcacagta ctgtgcgtcg tgactttcta agagaagtgt gcagcgggtg tgtcatcttg   4740
atatatgaaa ccctggaatt tccctcccct acacgcacgc accgtccccg ggggtccggt   4800
gtttgcagac atgctttgaa aagctgtctc agtgagacat cagttatgtc caaaatgagt   4860
ttaccttaga atcagaccgg ttttgccagg cgtcatgttt gcaaacatta tccacctaat   4920
cagattttga aaggccggct ttcatgtcgc ctgcctgaga ctcataacag atccccatta   4980
taagcgcgtt tacacagcaa aatgatttta ttgagaaaac cagcattaag tactgttgcc   5040
ggctcagttt tccattgcat actatctact taaagtcccg ttctcatttg taagtgttcc   5100
gatctttccc cacggagaaa actgagcaga gctgccgtgt cgcaggcttt ctgctgctga   5160
tgtcgcatct ctttgctttc ccctccttag tccatactcc aagtaagtga actcagacta   5220
ccagcaactt tttaactgaa aagtatctgt ccatgatgat caagatgcag ctcttcgtgt   5280
ttttattttg tctttttttt ttttttttttt ttttggaggg aaggagagac atcaactgga   5340
caaaatgcaa aatttggatg tgggacaatt gcttttttgga gacgtgaata gctgtactgt   5400
acgtattatt ttgtgtggca tgctaacttt gagccgggca ctggcctaat aaagtctttg   5460
taatcctccc agcaatccta taaagcagac gcagatagta aagatttttag gctttgcagg   5520
ccacgtacag actgtcacat gttctctgtt tttaaaagtg tcaacaacat tcttagctca   5580
aaaacaggct gcaggtggga tggtgcccac aggccatagt tggctgaccc cggctagggt   5640
gtaggcactt agcattccac tgtataaagg ggaaacccag gtcatactgc gtgtgcgtgg   5700
gtgggaagcc ggatgtggaa tacaggtggt ccctgagtct ccaggaacca ctgagctcca   5760
gctgttcaca cccacactct gcggcgcaag caactacctc gccacggttt agccttggtc   5820
tagcagcgac tttaaccttg aatgttgcat ttctgaaaaa tttagaatct tgaaagtaaa   5880
ggacgtccct ccggtgaata aaattaggcg caattataga atacatgtat tatggccacg   5940
tagcaatgac tgtattaggg ctctgctagt tctgtaataa atagacccga aaagcaa     5997
```

<210> SEQ ID NO 6  
<211> LENGTH: 628  
<212> TYPE: PRT  
<213> ORGANISM: Homo sapiens

<400> SEQUENCE: 6

```
Met Ala Ala Ala Val Asp Ser Ala Met Glu Val Val Pro Ala Leu
1               5                   10                  15

Ala Glu Glu Ala Ala Pro Glu Val Ala Gly Leu Ser Cys Leu Val Asn
                20                  25                  30

Leu Pro Gly Glu Val Leu Glu Tyr Ile Leu Cys Cys Gly Ser Leu Thr
            35                  40                  45

Ala Ala Asp Ile Gly Arg Val Ser Ser Thr Cys Arg Arg Leu Arg Glu
        50                  55                  60

Leu Cys Gln Ser Ser Gly Lys Val Trp Lys Glu Gln Phe Arg Val Arg
65                  70                  75                  80

Trp Pro Ser Leu Met Lys His Tyr Ser Pro Thr Asp Tyr Val Asn Trp
                85                  90                  95

Leu Glu Glu Tyr Lys Val Arg Gln Lys Ala Gly Leu Glu Ala Arg Lys
                100                 105                 110

Ile Val Ala Ser Phe Ser Lys Arg Phe Phe Ser Glu His Val Pro Cys
            115                 120                 125
```

```
Asn Gly Phe Ser Asp Ile Glu Asn Leu Glu Gly Pro Glu Ile Phe Phe
    130                 135                 140

Glu Asp Glu Leu Val Cys Ile Leu Asn Met Glu Gly Arg Lys Ala Leu
145                 150                 155                 160

Thr Trp Lys Tyr Tyr Ala Lys Lys Ile Leu Tyr Tyr Leu Arg Gln Gln
                165                 170                 175

Lys Ile Leu Asn Asn Leu Lys Ala Phe Leu Gln Gln Pro Asp Asp Tyr
            180                 185                 190

Glu Ser Tyr Leu Glu Gly Ala Val Tyr Ile Asp Gln Tyr Cys Asn Pro
        195                 200                 205

Leu Ser Asp Ile Ser Leu Lys Asp Ile Gln Ala Gln Ile Asp Ser Ile
210                 215                 220

Val Glu Leu Val Cys Lys Thr Leu Arg Gly Ile Asn Ser Arg His Pro
225                 230                 235                 240

Ser Leu Ala Phe Lys Ala Gly Glu Ser Ser Met Ile Met Glu Ile Glu
                245                 250                 255

Leu Gln Ser Gln Val Leu Asp Ala Met Asn Tyr Val Leu Tyr Asp Gln
            260                 265                 270

Leu Lys Phe Lys Gly Asn Arg Met Asp Tyr Tyr Asn Ala Leu Asn Leu
        275                 280                 285

Tyr Met His Gln Val Leu Ile Arg Arg Thr Gly Ile Pro Ile Ser Met
290                 295                 300

Ser Leu Leu Tyr Leu Thr Ile Ala Arg Gln Leu Gly Val Pro Leu Glu
305                 310                 315                 320

Pro Val Asn Phe Pro Ser His Phe Leu Leu Arg Trp Cys Gln Gly Ala
                325                 330                 335

Glu Gly Ala Thr Leu Asp Ile Phe Asp Tyr Ile Tyr Ile Asp Ala Phe
            340                 345                 350

Gly Lys Gly Lys Gln Leu Thr Val Lys Glu Cys Glu Tyr Leu Ile Gly
        355                 360                 365

Gln His Val Thr Ala Ala Leu Tyr Gly Val Val Asn Val Lys Lys Val
370                 375                 380

Leu Gln Arg Met Val Gly Asn Leu Leu Ser Leu Gly Lys Arg Glu Gly
385                 390                 395                 400

Ile Asp Gln Ser Tyr Gln Leu Leu Arg Asp Ser Leu Asp Leu Tyr Leu
                405                 410                 415

Ala Met Tyr Pro Asp Gln Val Gln Leu Leu Leu Gln Ala Arg Leu
            420                 425                 430

Tyr Phe His Leu Gly Ile Trp Pro Glu Lys Ser Phe Cys Leu Val Leu
        435                 440                 445

Lys Val Leu Asp Ile Leu Gln His Ile Gln Thr Leu Asp Pro Gly Gln
450                 455                 460

His Gly Ala Val Gly Tyr Leu Val Gln His Thr Leu Glu His Ile Glu
465                 470                 475                 480

Arg Lys Lys Glu Glu Val Gly Val Glu Val Lys Leu Arg Ser Asp Glu
                485                 490                 495

Lys His Arg Asp Val Cys Tyr Ser Ile Gly Leu Ile Met Lys His Lys
            500                 505                 510

Arg Tyr Gly Tyr Asn Cys Val Ile Tyr Gly Trp Asp Pro Thr Cys Met
        515                 520                 525

Met Gly His Glu Trp Ile Arg Asn Met Asn Val His Ser Leu Pro His
530                 535                 540
```

Gly His His Gln Pro Phe Tyr Asn Val Leu Val Glu Asp Gly Ser Cys
545                 550                 555                 560

Arg Tyr Ala Ala Gln Glu Asn Leu Glu Tyr Asn Val Glu Pro Gln Glu
            565                 570                 575

Ile Ser His Pro Asp Val Gly Arg Tyr Phe Ser Glu Phe Thr Gly Thr
        580                 585                 590

His Tyr Ile Pro Asn Ala Glu Leu Glu Ile Arg Tyr Pro Glu Asp Leu
    595                 600                 605

Glu Phe Val Tyr Glu Thr Val Gln Asn Ile Tyr Ser Ala Lys Lys Glu
    610                 615                 620

Asn Ile Asp Glu
625

<210> SEQ ID NO 7
<211> LENGTH: 1840
<212> TYPE: DNA
<213> ORGANISM: Homo sapiens

<400> SEQUENCE: 7

| | | | | | | |
|---|---|---|---|---|---|---|
| ctcttatata | aattctaaaa | attgatgttc | taagaagaga | ggtagaattt | gaatgactgg | 60 |
| gttacttcct | agactcttcc | tccttctctt | aagtacagta | tagttctttc | tctgaaaatc | 120 |
| ttcagtctct | tagttccaga | tgggttctct | atggtaagaa | tacaggacat | gtagaaggcc | 180 |
| ctagggaat | gctttcttcc | ccagatcttt | gccctgtagt | aggtttcagc | tgagcaagga | 240 |
| cgagtagttt | ttctggtgtt | tggcctcctc | tgttgggtgg | aaaaagactt | tcttctctat | 300 |
| tttcctagtt | atatatgcta | tcatatgtct | gttttctcc | tcttgaagtt | tccctgaaac | 360 |
| ctgggctctt | gaagacgcat | cactggagca | gatggataat | ggagactggg | gctatatgat | 420 |
| gactgaccca | gtcacattaa | atgtaggtgg | acacttgtat | acaacgtctc | tcaccacatt | 480 |
| gacgcgttac | ccggattcca | tgcttggagc | tatgtttggg | ggggacttcc | ccacagctcg | 540 |
| agaccctcaa | ggcaattact | ttattgatcg | agatggacct | cttttccgat | atgtcctcaa | 600 |
| cttcttaaga | acttcagaat | tgaccttacc | gttggatttt | aaggaatttg | atctgcttcg | 660 |
| gaaagaagca | gattttacc | agattgagcc | cttgattcag | tgtctcaatg | atcctaagcc | 720 |
| tttgtatccc | atggatactt | tgaagaagt | tgtggagctg | tctagtactc | ggaagctttc | 780 |
| taagtactcc | aacccagtgg | ctgtcatcat | aacgcaacta | accatcacca | ctaaggtcca | 840 |
| ttccttacta | gaaggcatct | caaattattt | taccaagtgg | aataagcaca | tgatggacac | 900 |
| cagagactgc | caggtttcct | ttacttttgg | accctgtgat | tatcaccagg | aagtttctct | 960 |
| tagggtccac | ctgatggaat | acattacaaa | acaaggtttc | acgatccgca | cacccgggt | 1020 |
| gcatcacatg | agtgagcggg | ccaatgaaaa | cacagtggag | cacaactgga | ctttctgtag | 1080 |
| gctagcccgg | aagacagacg | actgatctcc | gaccctgcca | caggttcctg | gaaagactct | 1140 |
| ccaggaaatg | gaagatactg | atttttttt | taaatcaca | gtgtgagata | tttttttct | 1200 |
| tttaaatagt | tgtatttatt | tgaaggcagt | gaggaccaga | aggaagtttt | gtgctttggc | 1260 |
| agactcctcc | atgttttgtt | cccttccccc | tgagtatgca | tgtgcctgtt | cagagtctcc | 1320 |
| agatacctt | tttataaaaa | gaagtctgaa | aatcattatg | gtatataatc | tacccttaac | 1380 |
| agagcttttc | ttattacagt | gctaaaatga | tttctgataa | aatggtccct | aactcaacta | 1440 |
| gaaggctaaa | aatacaagaa | tgaaagaata | agcagagtac | tcatgatgcc | tttgagaaaa | 1500 |
| atcaaaacat | catgtagggt | gacctagttt | ccaaaccaat | aaataagtag | tattgtaata | 1560 |

```
ttaaaggaaa actgttccaa tcatttaaaa gtacttatta agtactgctt tttacagtta    1620
tgacaactgt ttctttctat gcatataaat caaggaacca aatatctgta gccatggaaa    1680
tgtctgacta gaaatattta tattgaattc tgaatacaaa atgtccctgt ggtagaaaac    1740
ttactcttta tgcctggtgc agtataattc ccaagtgtac tgtctaccag aaaaaaaaaa    1800
caaaactaat aaaaaatgaa atatgaaaat taaaaaaaaa                          1840

<210> SEQ ID NO 8
<211> LENGTH: 237
<212> TYPE: PRT
<213> ORGANISM: Homo sapiens

<400> SEQUENCE: 8

Met Asp Asn Gly Asp Trp Gly Tyr Met Met Thr Asp Pro Val Thr Leu
1               5                   10                  15

Asn Val Gly Gly His Leu Tyr Thr Thr Ser Leu Thr Thr Leu Thr Arg
            20                  25                  30

Tyr Pro Asp Ser Met Leu Gly Ala Met Phe Gly Gly Asp Phe Pro Thr
        35                  40                  45

Ala Arg Asp Pro Gln Gly Asn Tyr Phe Ile Asp Arg Asp Gly Pro Leu
    50                  55                  60

Phe Arg Tyr Val Leu Asn Phe Leu Arg Thr Ser Glu Leu Thr Leu Pro
65                  70                  75                  80

Leu Asp Phe Lys Glu Phe Asp Leu Leu Arg Lys Glu Ala Asp Phe Tyr
                85                  90                  95

Gln Ile Glu Pro Leu Ile Gln Cys Leu Asn Asp Pro Lys Pro Leu Tyr
            100                 105                 110

Pro Met Asp Thr Phe Glu Glu Val Val Glu Leu Ser Ser Thr Arg Lys
        115                 120                 125

Leu Ser Lys Tyr Ser Asn Pro Val Ala Val Ile Ile Thr Gln Leu Thr
    130                 135                 140

Ile Thr Thr Lys Val His Ser Leu Leu Glu Gly Ile Ser Asn Tyr Phe
145                 150                 155                 160

Thr Lys Trp Asn Lys His Met Met Asp Thr Arg Asp Cys Gln Val Ser
                165                 170                 175

Phe Thr Phe Gly Pro Cys Asp Tyr His Gln Glu Val Ser Leu Arg Val
            180                 185                 190

His Leu Met Glu Tyr Ile Thr Lys Gln Gly Phe Thr Ile Arg Asn Thr
        195                 200                 205

Arg Val His His Met Ser Glu Arg Ala Asn Glu Asn Thr Val Glu His
    210                 215                 220

Asn Trp Thr Phe Cys Arg Leu Ala Arg Lys Thr Asp Asp
225                 230                 235

<210> SEQ ID NO 9
<211> LENGTH: 1080
<212> TYPE: DNA
<213> ORGANISM: Homo sapiens

<400> SEQUENCE: 9
gactattgcg cctgcgccag cgccggctgc gagactgggg ccgtggctgc tggtcccggg     60
tgatgctagg cggctccctg ggctccaggc tgttgcgggg tgtaggtggg agtcacggac    120
ggttcggggc ccgaggtgtc cgcgaaggtg gcgcagccat ggcggcaggg gagagcatgg    180
ctcagcggat ggtctgggtg gacctggaga tgacaggatt ggacattgag aaggaccaga    240
```

```
ttattgagat ggcctgtctg ataactgact ctgatctcaa cattttggct gaaggtccta      300
acctgattat aaaacaacca gatgagttgc tggacagcat gtcagattgg tgtaaggagc      360
atcacgggaa gtctggcctt accaaggcag tgaaggagag tacaattaca ttgcagcagg      420
cagagtatga atttctgtcc tttgtacgac agcagactcc tccagggctc tgtccacttg      480
caggaaattc agttcatgaa gataagaagt tccttgacaa atacatgccc cagttcatga      540
aacatcttca ttatagaata attgatgtga gcactgttaa agaactgtgc agacgctggt      600
atccagaaga atatgaattt gcaccaaaga aggctgcttc tcatagggca cttgatgaca      660
ttagtgaaag catcaaagag cttcagtttt accgaaataa catcttcaag aaaaaaatag      720
atgaaaagaa gaggaaaatt atagaaaatg gggaaaatga aagaccgtgt agttgatgcc      780
agttatcatg ctgccactac atcgttatct ggaggcaact tctggtggtt ttttttttctc      840 acgctgatgg cttggcagag caccttcggt taacttgcat tccagattg attactcaag       900 cagacagcac acgaaatact attttttctcc taatatgctg tttccattat gacacagcag     960
ctcctttgta agtaccaggt catgtccatc ccttggtaca tatatgcatt tgcttttaaa     1020
ccatttcttt tgtttaaata aataaataag taaataaagc tagttctatt gaaatgcaaa    1080
```

<210> SEQ ID NO 10
<211> LENGTH: 237
<212> TYPE: PRT
<213> ORGANISM: Homo sapiens

<400> SEQUENCE: 10

```
Met Leu Gly Gly Ser Leu Gly Ser Arg Leu Leu Arg Gly Val Gly Gly
1               5                   10                  15

Ser His Gly Arg Phe Gly Ala Arg Gly Val Arg Glu Gly Gly Ala Ala
            20                  25                  30

Met Ala Ala Gly Glu Ser Met Ala Gln Arg Met Val Trp Val Asp Leu
        35                  40                  45

Glu Met Thr Gly Leu Asp Ile Glu Lys Asp Gln Ile Ile Glu Met Ala
    50                  55                  60

Cys Leu Ile Thr Asp Ser Asp Leu Asn Ile Leu Ala Glu Gly Pro Asn
65                  70                  75                  80

Leu Ile Ile Lys Gln Pro Asp Glu Leu Leu Asp Ser Met Ser Asp Trp
                85                  90                  95

Cys Lys Glu His His Gly Lys Ser Gly Leu Thr Lys Ala Val Lys Glu
            100                 105                 110

Ser Thr Ile Thr Leu Gln Gln Ala Glu Tyr Glu Phe Leu Ser Phe Val
        115                 120                 125

Arg Gln Gln Thr Pro Pro Gly Leu Cys Pro Leu Ala Gly Asn Ser Val
    130                 135                 140

His Glu Asp Lys Lys Phe Leu Asp Lys Tyr Met Pro Gln Phe Met Lys
145                 150                 155                 160

His Leu His Tyr Arg Ile Ile Asp Val Ser Thr Val Lys Glu Leu Cys
                165                 170                 175

Arg Arg Trp Tyr Pro Glu Glu Tyr Glu Phe Ala Pro Lys Lys Ala Ala
            180                 185                 190

Ser His Arg Ala Leu Asp Asp Ile Ser Glu Ser Ile Lys Glu Leu Gln
        195                 200                 205

Phe Tyr Arg Asn Asn Ile Phe Lys Lys Lys Ile Asp Glu Lys Lys Arg
    210                 215                 220
```

Lys Ile Ile Glu Asn Gly Glu Asn Glu Lys Thr Val Ser
225                 230                 235

<210> SEQ ID NO 11
<211> LENGTH: 2548
<212> TYPE: DNA
<213> ORGANISM: Homo sapiens

<400> SEQUENCE: 11

| | | | | | |
|---|---|---|---|---|---|
| ctcaggactc | agaggctggg | atcatggtag | atgaaccct | ccttttactc | ctctcggagg | 60 |
| ccctggccct | tacccagacc | tgggcgggct | cccactcctt | gaagtatttc | cacacttccg | 120 |
| tgtcccggcc | cggccgcggg | gagccccgct | tcatctctgt | gggctacgtg | gacgacaccc | 180 |
| agttcgtgcg | cttcgacaac | gacgccgcga | gtccgaggat | ggtgccgcgg | gcgccgtgga | 240 |
| tggagcagga | ggggtcagag | tattgggacc | gggagacacg | gagcgccagg | gacaccgcac | 300 |
| agattttccg | agtgaatctg | cggacgctgc | gcggctacta | caatcagagc | gaggccgggt | 360 |
| ctcacaccct | gcagtggatg | catggctgcg | agctggggcc | cgacgggcgc | ttcctccgcg | 420 |
| ggtatgaaca | gttcgcctac | gacggcaagg | attatctcac | cctgaatgag | gacctgcgct | 480 |
| cctggaccgc | ggtggacacg | gcggctcaga | tctccgagca | aaagtcaaat | gatgcctctg | 540 |
| aggcggagca | ccagagagcc | tacctggaag | acacatgcgt | ggagtggctc | cacaaatacc | 600 |
| tggagaaggg | gaaggagacg | ctgcttcacc | tggagccccc | aaagacacac | gtgactcacc | 660 |
| accccatctc | tgaccatgag | gccaccctga | ggtgctgggc | cctgggcttc | taccctgcgg | 720 |
| agatcacact | gacctggcag | caggatgggg | agggccatac | ccaggacacg | agctcgtgg | 780 |
| agaccaggcc | tgcaggggat | ggaaccttcc | agaagtgggc | agctgtggtg | gtgccttctg | 840 |
| gagaggagca | gagatacacg | tgccatgtgc | agcatgaggg | gctacccgag | cccgtcaccc | 900 |
| tgagatggaa | gccggcttcc | cagcccacca | tccccatcgt | gggcatcatt | gctggcctgg | 960 |
| ttctccttgg | atctgtggtc | tctggagctg | tggttgctgc | tgtgatatgg | aggaagaaga | 1020 |
| gctcaggtgg | aaaaggaggg | agctactcta | aggctgagtg | gagcgacagt | gcccagggt | 1080 |
| ctgagtctca | cagcttgtaa | agcctgagac | agctgccttg | tgtgcgactg | agatgcacag | 1140 |
| ctgccttgtg | tgcgactgag | atgcaggatt | tcctcacgcc | tcccctatgt | gtcttagggg | 1200 |
| actctggctt | ctcttttgc | aagggcctct | gaatctgtct | gtgtccctgt | tagcacaatg | 1260 |
| tgaggaggta | gagaaacagt | ccacctctgt | gtctaccatg | acccccttcc | tcacactgac | 1320 |
| ctgtgttcct | tccctgttct | cttttctatt | aaaaataaga | acctgggcag | agtgcggcag | 1380 |
| ctcatgcctg | taatcccagc | acttagggag | gccgaggagg | cagatcacg | aggtcaggag | 1440 |
| atcgaaacca | tcctggctaa | cacggtgaaa | ccccgtctct | actaaaaaat | acaaaaaatt | 1500 |
| agctgggcgc | agaggcacgg | gcctgtagtc | ccagctactc | aggaggcgga | ggcaggagaa | 1560 |
| tggcgtcaac | ccgggaggcg | gaggttgcag | tgagccagga | ttgtgcgact | gcactccagc | 1620 |
| ctgggtgaca | gggtgaaacg | ccatctcaaa | aaataaaaat | tgaaaataa | aaaagaacc | 1680 |
| tggatctcaa | tttaattttt | catattcttg | caatgaaatg | gacttgagga | agctaagatc | 1740 |
| atagctagaa | atacagataa | ttccacagca | catctctagc | aaatttagcc | tattcctatt | 1800 |
| ctctagccta | ttccttacca | cctgtaatct | tgaccatata | ccttggagtt | gaatattgtt | 1860 |
| ttcatactgc | tgtggtttga | atgttccctc | caacactcat | gttgagactt | aatccctaat | 1920 |
| gtggcaatac | tgaaaggtgg | ggcctttgag | atgtgattgg | atcgtaaggc | tgtgccttca | 1980 |
| ttcatggggtt | aatggattaa | tgggttatca | caggaatggg | actggtggct | ttataagaag | 2040 |

```
aggaaaagag aactgagcta gcatgcccag cccacagaga gcctccacta gagtgatgct    2100
aagtggaaat gtgaggtgca gctgccacag agggccccca ccagggaaat gtctagtgtc    2160
tagtggatcc aggccacagg agagagtgcc ttgtggagcg ctgggagcag gacctgacca    2220
ccaccaggac cccagaactg tggagtcagt ggcagcatgc agcgcccct tgggaaagct     2280 ttaggcacca gcctgcaacc cattcgagca gccacgtagg ctgcacccag caaagccaca    2340
ggcacggggc tacctgaggc cttgggggcc caatccctgc tccagtgtgt ccgtgaggca    2400
gcacacgaag tcaaaagaga ttattctctt cccacagata cctttctct cccatgaccc     2460 tttaacagca tctgcttcat tcccctcacc ttcccaggct gatctgaggt aaactttgaa    2520
gtaaaataaa agctgtgttt gagcatca                                       2548
```

<210> SEQ ID NO 12
<211> LENGTH: 358
<212> TYPE: PRT
<213> ORGANISM: Homo sapiens

<400> SEQUENCE: 12

```
Met Val Asp Gly Thr Leu Leu Leu Leu Ser Glu Ala Leu Ala Leu
1               5                   10                  15

Thr Gln Thr Trp Ala Gly Ser His Ser Leu Lys Tyr Phe His Thr Ser
            20                  25                  30

Val Ser Arg Pro Gly Arg Gly Glu Pro Arg Phe Ile Ser Val Gly Tyr
        35                  40                  45

Val Asp Asp Thr Gln Phe Val Arg Phe Asp Asn Asp Ala Ala Ser Pro
    50                  55                  60

Arg Met Val Pro Arg Ala Pro Trp Met Glu Gln Glu Gly Ser Glu Tyr
65                  70                  75                  80

Trp Asp Arg Glu Thr Arg Ser Ala Arg Asp Thr Ala Gln Ile Phe Arg
                85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Gly
        115                 120                 125

Arg Phe Leu Arg Gly Tyr Glu Gln Phe Ala Tyr Asp Gly Lys Asp Tyr
    130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Pro Ser
            260                 265                 270
```

Gly Glu Glu Gln Arg Tyr Thr Cys His Val Gln His Glu Gly Leu Pro
            275                 280                 285

Glu Pro Val Thr Leu Arg Trp Lys Pro Ala Ser Gln Pro Thr Ile Pro
        290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
            355

<210> SEQ ID NO 13
<211> LENGTH: 3919
<212> TYPE: DNA
<213> ORGANISM: Homo sapiens

<400> SEQUENCE: 13

| | | | | | |
|---|---|---|---|---|---|
| gcgggcggcg | cgagcgaggg | gcagaggcga | gagacgccgg | cggggcgcgg | gcgcggcggc | 60 |
| cccggaggat | gctgctgagc | cccggcactg | cctggctgcg | agcacatgat | ggcgatacgg | 120 |
| gagctcaaag | tgtgccttct | cggggacact | ggggttggga | aatcaagcat | cgtgtgtcga | 180 |
| tttgtccagg | atcactttga | ccacaacatc | agccctacta | ttggggcatc | ttttatgacc | 240 |
| aaaactgtgc | cttgtggaaa | tgaacttcac | aagttcctca | tctgggacac | tgctggtcag | 300 |
| gaacggtttc | attcattggc | tcccatgtac | tatcgaggct | cagctgcagc | tgttatcgtg | 360 |
| tatgatatta | ccaagcagga | ttcattttat | accttgaaga | atgggtcaa | ggagctgaaa | 420 |
| gaacatggtc | agaaaacat | tgtaatggcc | atcgctggaa | acaagtgcga | cctctcagat | 480 |
| attagggagg | ttccctgaa | ggatgctaag | gaatacgctg | aatccatagg | tgccatcgtg | 540 |
| gttgagacaa | gtgcaaaaaa | tgctattaat | atcgaagagc | tctttcaagg | aatcagccgc | 600 |
| cagatcccac | ccttggaccc | ccatgaaaat | ggaaacaatg | aacaatcaa | agttgagaag | 660 |
| ccaaccatgc | aagccagccg | ccggtgctgt | tgacccaagg | gccgtggtcc | acggtacttg | 720 |
| aagaagccag | agcccacatc | ctgtgcactg | ctgaaggacc | ctacgctcgg | tggcctggca | 780 |
| cctcactttg | agaagagtga | gcacactggc | tttgcatcct | ggaagacctg | caggggcgg | 840 |
| ggcaggaaat | gtacctgaaa | aggatttag | aaaaccctgg | gaaaacccac | cacaccacca | 900 |
| caaaatggcc | tttagtgtat | gaaatgcaca | tggaggggat | gtagttgcat | ttttgctaaa | 960 |
| aaaaaaaaaa | aacctttaaa | aattgttgga | tgtgtacaaa | agtcttactg | ccttattatg | 1020 |
| tgtatgggat | tctaaagtgg | cattccactt | ggatttcctg | tgctacctat | ccaaattcca | 1080 |
| gtaactactt | cagtgtcatt | gcctttgtta | cctaaccaac | cttcactgaa | aggcaaattt | 1140 |
| agttcaggag | gttagttttt | agctagcttt | ggaagtaagc | ctttatttat | tacttttgg | 1200 |
| aggaaatcag | agaagtgtca | atggaccgtc | actcagactg | agacttgagt | tattacagaa | 1260 |
| gccaggaaaa | gtgtattaga | aactgttgtc | tacaccactt | ttaattggtg | aacaattttt | 1320 |
| ctaagttatg | gtcatatata | cccaaacaaa | ccaaatcaaa | ctaaattact | gcatataatt | 1380 |
| ttgggattgg | gtggcctagt | ttgaaagagt | gatttaagta | atcactatgt | aagtggtgag | 1440 |
| agatgcagga | catacacatt | attcaagaga | ccacctgaca | tgcatctcct | ccgcaggaat | 1500 |
| acattcgtcc | tctcttagag | aagtttaacg | cacatagtat | tatttactact | agagaatatc | 1560 |

```
tcttggtgtc atatctaggg gaagagaatt aactagaatt aaatttaatg tttgaatcta    1620
aatcattggg caaacttcta ataataacaa ttaataatag gttacaggaa agccagccag    1680
aggaagtgtc agcactttaa aattctagac cccaaaaaac tacaaaatca gaaaaagtat    1740
ttttatgttt ctagcttgag gagaagggct ttagggctaa ccagaggtct gaccctagaa    1800
tgccaaggaa ctgagaatgg gctccgatga aaaccttcct tttcagattc cctgtctgct    1860
caattaaaga tgtttgaatc caaaggaagt caaggaagaa aaagcatgga aaggaagaga    1920
actgattcct actgaaaatt caaattctat taccattcta actttcataa aaagttggga    1980
tcaagaagca gctgatttcc tgccagggct tatattaggg ggtgattctt aaaggacatt    2040
aggattggtg ctcagaaatg gttaatcatg ctgtgtgcta gccagggcca gctggtacct    2100
tctttgccat gagcattcaa gggacggcta acctttattg acaatctata tcgcaaaagt    2160
caggaaagag gttgtgagct gattggatta aagacctggc acttcagtaa ctcagcacgc    2220
ttccacttca ctcaacttaa gagagttcat tgacagtgtt aggatgtgaa ggctgggaaa    2280
cacttatttt gcttcaagag ttccacttgg ctctcccaaa taggtacctc aaaaactgtt    2340
agcaagcggc atttggatgt cttgacaggg gctttgcagg gattttttagg gttttttcca    2400
cattgtccac attaatggtt ggcatgattg tgcttgcagg ccaagaaatg atcataccccc   2460
ttgccaaagg taaaaaaaaa aaaaaaaaaa tgagttgaaa attgaagtga cctctttcca    2520
gctgagttgc aggcttatttt tgtaacctttt cctcatccag ttttccctga gaacctgggt   2580
ttatctctag atagctgttc aggttttttta gctgagggggt aagtatccta gctgagagtt   2640
ttgcatcttt gggctgggtt tgcagtggtt gtgttttgca taaaatgtct agtctttgcc    2700
acagatagtg agctacccac taatgagccc atggtttttat ttcagaagca catgagggtg   2760
tgaaaccact ctgttaccttt tctgtattgt cttagctatt caagccagtc agaggataat    2820
atatatattc tcatcagcac tcagagtagt cagtgaagag agtagatcac acttgggcac    2880
accaggattc acataaacat tgtatcttct ctgtggatgc tcaggccttg tctacaatga    2940
ggctttacaa ccttcctttg ttttggctcg ggattacttc ctggctgtct aataattgaa    3000
ccataaccat gtaatattat gtaaaggcct ggaaattact gttgctaaaa aaagtcatgt    3060
agtttcatgt agtgtagcat ccttggcatc gttttccaaa atttgttcct tctcccttttt   3120
tttttttcttt cgtgtgtggc atgagtgtgt atctgtgtaa atatgattgt atatgtgtta    3180
ctccgatatg taatccattt cactggctga gtttggcccc tagccatgtg ttaatataaa    3240
gtaggcatgg cttcccaatg gaaatctctg agaatgacag tggagttgtg caagcatttt    3300
acattgccac ataattgact tgccatttta tggttaaaaa cggcacatta ggcagttgaa    3360
tatgacgtta ccttgcagac taaaaggttg aaggcccgaa actaacttttt agctaacaat    3420
aagggctgtg ccccaatgga aactgagttc atttttctgag aaaggtttgg atgactgaaa    3480
tatttcctct acagtcaagg actttggcat gtggtggctg aaactgagct ttttttgtgtg    3540
ggctccagtt ctcactgttc tgcaatgctc atggcaagtt gaatggtgag ctagcttata    3600
aattaaagag ctctgaactg tattcagacc gactgggtat ctagcttact gttttaacat    3660
cattgttgaa accagaccct gtagtccagt ggtgctgccc tgttgtgcaa actgctcctt    3720
tttctcgtgt ttttgtaaag agcttccatc tgggctggac ccagttcttg cacatacaag    3780
acaccgctgc agtcagctag gacctttccg ccatgtattc tattctgtag taaagcatttt   3840
ccatcaacaa tgcctaattg tatctgttat ttttggttta acacacactg attcatacta    3900
ataaatattt tcagttttta                                                3919
```

<210> SEQ ID NO 14
<211> LENGTH: 195
<212> TYPE: PRT
<213> ORGANISM: Homo sapiens

<400> SEQUENCE: 14

Met Met Ala Ile Arg Glu Leu Lys Val Cys Leu Leu Gly Asp Thr Gly
1               5                   10                  15

Val Gly Lys Ser Ser Ile Val Cys Arg Phe Val Gln Asp His Phe Asp
                20                  25                  30

His Asn Ile Ser Pro Thr Ile Gly Ala Ser Phe Met Thr Lys Thr Val
            35                  40                  45

Pro Cys Gly Asn Glu Leu His Lys Phe Leu Ile Trp Asp Thr Ala Gly
    50                  55                  60

Gln Glu Arg Phe His Ser Leu Ala Pro Met Tyr Tyr Arg Gly Ser Ala
65                  70                  75                  80

Ala Ala Val Ile Val Tyr Asp Ile Thr Lys Gln Asp Ser Phe Tyr Thr
                85                  90                  95

Leu Lys Lys Trp Val Lys Glu Leu Lys Glu His Gly Pro Glu Asn Ile
                100                 105                 110

Val Met Ala Ile Ala Gly Asn Lys Cys Asp Leu Ser Asp Ile Arg Glu
            115                 120                 125

Val Pro Leu Lys Asp Ala Lys Glu Tyr Ala Glu Ser Ile Gly Ala Ile
    130                 135                 140

Val Val Glu Thr Ser Ala Lys Asn Ala Ile Asn Ile Glu Glu Leu Phe
145                 150                 155                 160

Gln Gly Ile Ser Arg Gln Ile Pro Pro Leu Asp Pro His Glu Asn Gly
                165                 170                 175

Asn Asn Gly Thr Ile Lys Val Glu Lys Pro Thr Met Gln Ala Ser Arg
            180                 185                 190

Arg Cys Cys
        195

<210> SEQ ID NO 15
<211> LENGTH: 4598
<212> TYPE: DNA
<213> ORGANISM: Homo sapiens

<400> SEQUENCE: 15
ctctcaacca tcaggttcgg cagcccgcgg cgccgcctgg cagctcctcc tcttctccgc      60
cccgccggcc gcgggcgcgg gggacgtcag cgctgccagc gtggaaggag ctgcggggcg     120
cgggaggagg aagtagagcc cggaccgcc aggccaccac cggccgcctc agccatggac     180
gcgtccctgg agaagatagc agaccccacg ttagctgaaa tgggaaaaaa cttgaaggag     240
gcagtgaaga tgctggagga cagtcagaga gaaacagaag aggaaaatgg aaagaagctc     300
atatccggag atattccagg cccactccag ggcagtgggc aagatatggt gagcatcctc     360
cagttagttc agaatctcat gcatggagat gaagatgagg agccccagag ccccagaatc     420
caaaatattg gagaacaagg tcatatggct tgttgggac atagtctggg agcttatatt     480
tcaactctgg acaaagagaa gctgagaaaa cttacaacta ggatactttc agataccacc     540
ttatggctat gcagaatttt cagatatgaa aatgggtgtg cttatttcca cgaagaggaa     600
agagaaggac ttgcaaagat atgtaggctt gccattcatt ctcgatatga agacttcgta     660
gtggatggct tcaatgtgtt atataacaag aagcctgtca tatatcttag tgctgctgct     720

```
agacctggcc tgggccaata cctttgtaat cagctcggct tgcccttccc ctgcttgtgc    780
cgtgtaccct gtaacactgt gtttggatcc cagcatcaga tggatgttgc cttcctggag    840
aaactgatta agatgatat agagcgagga agactgcccc tgttgcttgt cgcaaatgca    900
ggaacggcag cagtaggaca cacagacaag attgggagat tgaaagaact ctgtgagcag    960
tatggcatat ggcttcatgt ggagggtgtg aatctggcaa cattggctct gggttatgtc   1020
tcctcatcag tgctggctgc agccaaatgt gatagcatga cgatgactcc tggcccgtgg   1080
ctgggtttgc cagctgttcc tgcggtgaca ctgtataaac acgatgaccc tgccttgact   1140
ttagttgctg gtcttacatc aaataagccc acagacaaac tccgtgccct gcctctgtgg   1200
ttatctttac aatacttggg acttgatggg tttgtggaga ggatcaagca tgcctgtcaa   1260
ctgagtcaac ggttgcagga aagtttgaag aaagtgaatt acatcaaaat cttggtggaa   1320
gatgagctca gctccccagt ggtggtgttc agattttttcc aggaattacc aggctcagat   1380
ccggtgttta aagccgtccc agtgcccaac atgacaccttt caggagtcgg ccgggagagg   1440
cactcgtgtg acgcgctgaa tcgctggctg ggagaacagc tgaagcagct ggtgcctgca   1500
agcggcctca cagtcatgga tctggaagct gagggcacgt gtttgcggtt cagccctttg   1560
atgaccgcag cagttttagg aactcgggga gaggatgtgg atcagctcgt agcctgcata   1620
gaaagcaaac tgccagtgct gtgctgtacg ctccagttgc gtgaagagtt caagcaggaa   1680
gtggaagcaa cagcaggtct cctatatgtt gatgacccta actggtctgg aatagggtt    1740 gtcaggtatg aacatgctaa tgatgataag agcagtttga aatcagatcc cgaaggggaa   1800
aacatccatg ctggactcct gaagaagtta atgaactgg aatctgacct aacctttaaa    1860
ataggccctg agtataagag catgaagagc tgcctttatg tcggcatggc gagcgacaac   1920
gtcgatgctg ctgagctcgt ggagaccatt gcggccacag cccgggagat agaggagaac   1980
tcgaggcttc tggaaaacat gacagaagtg gttcggaaag gcattcagga agctcaagtg   2040
gagctgcaga aggcaagtga agaacggctt ctggaagagg gggtgttgcg gcagatccct   2100
gtagtgggct ccgtgctgaa ttggttttct ccggtccagg ctttacagaa gggaagaact   2160
tttaacttga cagcaggctc tctggagtcc acagaaccca tatatgtcta caaagcacaa   2220
ggtgcaggag tcacgctgcc tccaacgccc tcgggcagtc gcaccaagca gaggcttcca   2280
ggccagaagc cttttaaaag gtccctgcga ggttcagatg ctttgagtga gaccagctca   2340
gtcagtcaca ttgaagactt agaaaaggtg gagcgcctat ccagtgggcc ggagcagatc   2400
accctcgagg ccagcagcac tgagggacac ccaggggctc ccagccctca gcacaccgac   2460
cagaccgagg ccttccagaa aggggtccca cacccagaag atgaccactc acaggtagaa   2520
ggaccggaga gcttaagatg agactcattg tgtggtttga gactgtactg agtattgttt   2580
cagggaagat gaagttctat tggaaatgtg aactgtgcca catactaata taaattactg   2640
ttgtttgtgc ttcactggga ttttggcaca aatatgtgcc tgaaaggtag gctttctagg   2700
aggggagtca gcttgtctaa cttcatgtac atgtagaacc acgtttgctg tcctactacg   2760
acttttccct aagttaccat aaacacattt tattcacaaa aaacacttcg aatttcaagt   2820
gtctaccagt agcacccttg ctctttctaa acataagcct aagtatatga ggttgcccgt   2880
ggcaactttt tggtaaaaca gcttttcatt agcactctcc aggttctctg caacacttca   2940
cagaggcgag actggctgta tcctttgctg tcggtcttta gtacgatcaa gttgcaatat   3000
acagtgggac tgctagactt gaaggagagc agtgattgtg ggattgtaaa taagagcatc   3060
```

```
agaagccctc cccagctact gctcttcgtg gagacttagt aaggactgtg tctacttgag    3120
ctgtggcaag gctgctgtct gggactgtcc tctgccacaa ggccatttct cccattatat    3180
accgtttgta aagagaaact gtaaagtctc ctcctgacca tatattttta aatactggca    3240
aagcttttaa aattggcaca caagtacaga ctgtgctcat ttctgtttag tatctgaaaa    3300
cctgatagat gctacccttta agagcttgct cttccgtgtg ctacgtagca cccacctggt    3360
taaaatctga aaacaagtac ccctttgacc tgtctcccac tgaagcttct actgccctgg    3420
cagctcgcct gggcccaact cagaaacagg agccagcaga gcactctctc acgctgatcc    3480
agccgggcac cctgcttaag tcagtagaag ctcgctggca ctgcccgttc ctacttttcc    3540
gaagtactgc gtcactttgt cgtaagtaat ggcccctgtg ccttcttaat ccagcagtca    3600
agcttttggg agacctgaaa atgggaaaat tcacactggg tttctggact gtagtattgg    3660
aagccttagt tatagtatat taagcctata attatactct gatttgatgg gattttgac    3720
atttacactt gtcaaaatgc aggggtttt ttttggtgca gatgattaaa cagtcttccc    3780
tatttggtgc aatgaagtat agcagataaa atggggagg ggtaaattat cccttcaag    3840
aaaattacat gttttatat atatttggaa ttgttaaatt ggttttgctg aaacatttca    3900
cccttgagat attatttgaa tgttggtttc aataaaggtt cttgaaattg ttaccagtga    3960
attcagttta taaatcttat tacaaaagac ttacccacgt acctgaaata gctgccgata    4020
gaccagtgag aggtaggttc tcctctgccc gttattaccg accaaaaaaa aaactggaca    4080
tcaattttt agtaaaccaa aaaataagtc tcaacaaatg cctttgccaa ataaggttt    4140
tatttgaaaa gtcatttgat gaaagtcatt tgaaagacac tgaggaggga aggaggccta    4200
agacccaaca gatgtaggat ccagatctgg attcgtgcca gccccaccaa tggtctgtca    4260
ggccaagaag gtgctttctt tggtaattca tgttttttaa cttcctggag aagagatctt    4320
ttcccacaag ccatcttcat ttttttgta gagtagggct ttatttccag aaaacagtgt    4380
gtgagctgga gatgggtgtt ttttaaaaa catcaaggta gatctaatat gttcaacaaa    4440
gtggggtggc tcagccagag gcgaagtgga aagattctga aaacacaaga tggtgggcat    4500
tagagaagcc aaccttactg tcccctgctg tgataaagat gtcaaagtat ctttgttctt    4560
ggacacaaat atatataata aaatacgtta agaaatga                            4598
```

<210> SEQ ID NO 16
<211> LENGTH: 788
<212> TYPE: PRT
<213> ORGANISM: Homo sapiens

<400> SEQUENCE: 16

Met Asp Ala Ser Leu Glu Lys Ile Ala Asp Pro Thr Leu Ala Glu Met
1               5                   10                  15

Gly Lys Asn Leu Lys Glu Ala Val Lys Met Leu Glu Asp Ser Gln Arg
            20                  25                  30

Arg Thr Glu Glu Glu Asn Gly Lys Lys Leu Ile Ser Gly Asp Ile Pro
        35                  40                  45

Gly Pro Leu Gln Gly Ser Gly Gln Asp Met Val Ser Ile Leu Gln Leu
    50                  55                  60

Val Gln Asn Leu Met His Gly Asp Glu Asp Glu Pro Gln Ser Pro
65                  70                  75                  80

Arg Ile Gln Asn Ile Gly Glu Gln Gly His Met Ala Leu Leu Gly His
                85                  90                  95

```
Ser Leu Gly Ala Tyr Ile Ser Thr Leu Asp Lys Glu Lys Leu Arg Lys
            100                 105                 110

Leu Thr Thr Arg Ile Leu Ser Asp Thr Thr Leu Trp Leu Cys Arg Ile
            115                 120                 125

Phe Arg Tyr Glu Asn Gly Cys Ala Tyr Phe His Glu Glu Arg Glu
    130                 135                 140

Gly Leu Ala Lys Ile Cys Arg Leu Ala Ile His Ser Arg Tyr Glu Asp
145                 150                 155                 160

Phe Val Val Asp Gly Phe Asn Val Leu Tyr Asn Lys Lys Pro Val Ile
                165                 170                 175

Tyr Leu Ser Ala Ala Arg Pro Gly Leu Gly Gln Tyr Leu Cys Asn
            180                 185                 190

Gln Leu Gly Leu Pro Phe Pro Cys Leu Cys Arg Val Pro Cys Asn Thr
            195                 200                 205

Val Phe Gly Ser Gln His Gln Met Asp Val Ala Phe Leu Glu Lys Leu
    210                 215                 220

Ile Lys Asp Asp Ile Glu Arg Gly Arg Leu Pro Leu Leu Leu Val Ala
225                 230                 235                 240

Asn Ala Gly Thr Ala Ala Val Gly His Thr Asp Lys Ile Gly Arg Leu
                245                 250                 255

Lys Glu Leu Cys Glu Gln Tyr Gly Ile Trp Leu His Val Glu Gly Val
            260                 265                 270

Asn Leu Ala Thr Leu Ala Leu Gly Tyr Val Ser Ser Val Leu Ala
            275                 280                 285

Ala Ala Lys Cys Asp Ser Met Thr Met Thr Pro Gly Pro Trp Leu Gly
            290                 295                 300

Leu Pro Ala Val Pro Ala Val Thr Leu Tyr Lys His Asp Asp Pro Ala
305                 310                 315                 320

Leu Thr Leu Val Ala Gly Leu Thr Ser Asn Lys Pro Thr Asp Lys Leu
                325                 330                 335

Arg Ala Leu Pro Leu Trp Leu Ser Leu Gln Tyr Leu Gly Leu Asp Gly
            340                 345                 350

Phe Val Glu Arg Ile Lys His Ala Cys Gln Leu Ser Gln Arg Leu Gln
            355                 360                 365

Glu Ser Leu Lys Lys Val Asn Tyr Ile Lys Ile Leu Val Glu Asp Glu
            370                 375                 380

Leu Ser Ser Pro Val Val Phe Arg Phe Phe Gln Glu Leu Pro Gly
385                 390                 395                 400

Ser Asp Pro Val Phe Lys Ala Val Pro Val Pro Asn Met Thr Pro Ser
                405                 410                 415

Gly Val Gly Arg Glu Arg His Ser Cys Asp Ala Leu Asn Arg Trp Leu
            420                 425                 430

Gly Glu Gln Leu Lys Gln Leu Val Pro Ala Ser Gly Leu Thr Val Met
            435                 440                 445

Asp Leu Glu Ala Glu Gly Thr Cys Leu Arg Phe Ser Pro Leu Met Thr
            450                 455                 460

Ala Ala Val Leu Gly Thr Arg Gly Glu Asp Val Asp Gln Leu Val Ala
465                 470                 475                 480

Cys Ile Glu Ser Lys Leu Pro Val Leu Cys Cys Thr Leu Gln Leu Arg
                485                 490                 495

Glu Glu Phe Lys Gln Glu Val Glu Ala Thr Ala Gly Leu Leu Tyr Val
            500                 505                 510
```

Asp Asp Pro Asn Trp Ser Gly Ile Gly Val Val Arg Tyr Glu His Ala
            515                 520                 525

Asn Asp Asp Lys Ser Ser Leu Lys Ser Asp Pro Glu Gly Glu Asn Ile
        530                 535                 540

His Ala Gly Leu Leu Lys Lys Leu Asn Glu Leu Glu Ser Asp Leu Thr
545                 550                 555                 560

Phe Lys Ile Gly Pro Glu Tyr Lys Ser Met Lys Ser Cys Leu Tyr Val
                565                 570                 575

Gly Met Ala Ser Asp Asn Val Asp Ala Ala Glu Leu Val Glu Thr Ile
            580                 585                 590

Ala Ala Thr Ala Arg Glu Ile Glu Asn Ser Arg Leu Leu Glu Asn
        595                 600                 605

Met Thr Glu Val Val Arg Lys Gly Ile Gln Glu Ala Gln Val Glu Leu
610                 615                 620

Gln Lys Ala Ser Glu Glu Arg Leu Leu Glu Glu Gly Val Leu Arg Gln
625                 630                 635                 640

Ile Pro Val Val Gly Ser Val Leu Asn Trp Phe Ser Pro Val Gln Ala
                645                 650                 655

Leu Gln Lys Gly Arg Thr Phe Asn Leu Thr Ala Gly Ser Leu Glu Ser
            660                 665                 670

Thr Glu Pro Ile Tyr Val Tyr Lys Ala Gln Gly Ala Gly Val Thr Leu
675                 680                 685

Pro Pro Thr Pro Ser Gly Ser Arg Thr Lys Gln Arg Leu Pro Gly Gln
        690                 695                 700

Lys Pro Phe Lys Arg Ser Leu Arg Gly Ser Asp Ala Leu Ser Glu Thr
705                 710                 715                 720

Ser Ser Val Ser His Ile Glu Asp Leu Glu Lys Val Glu Arg Leu Ser
                725                 730                 735

Ser Gly Pro Glu Gln Ile Thr Leu Glu Ala Ser Ser Thr Glu Gly His
            740                 745                 750

Pro Gly Ala Pro Ser Pro Gln His Thr Asp Gln Thr Glu Ala Phe Gln
        755                 760                 765

Lys Gly Val Pro His Pro Glu Asp Asp His Ser Gln Val Glu Gly Pro
770                 775                 780

Glu Ser Leu Arg
785

<210> SEQ ID NO 17
<211> LENGTH: 25
<212> TYPE: DNA
<213> ORGANISM: Artificial Sequence
<220> FEATURE:
<223> OTHER INFORMATION: Synthetic construct

<400> SEQUENCE: 17
ccattggagg gcaagtctgg tgcca                                              25

<210> SEQ ID NO 18
<211> LENGTH: 25
<212> TYPE: DNA
<213> ORGANISM: Artificial Sequence
<220> FEATURE:
<223> OTHER INFORMATION: Synthetic construct

<400> SEQUENCE: 18
ggaacacctt cccgctgctg gctcc                                              25

```
<210> SEQ ID NO 19
<211> LENGTH: 25
<212> TYPE: DNA
<213> ORGANISM: Artificial Sequence
<220> FEATURE:
<223> OTHER INFORMATION: Synthetic construct

<400> SEQUENCE: 19
gttcaagacg gctaagtcct tgttt                                              25

<210> SEQ ID NO 20
<211> LENGTH: 25
<212> TYPE: DNA
<213> ORGANISM: Artificial Sequence
<220> FEATURE:
<223> OTHER INFORMATION: Synthetic construct

<400> SEQUENCE: 20
tgaaagaggt tcaagcagtt cttct                                              25

<210> SEQ ID NO 21
<211> LENGTH: 25
<212> TYPE: DNA
<213> ORGANISM: Artificial Sequence
<220> FEATURE:
<223> OTHER INFORMATION: Synthetic construct

<400> SEQUENCE: 21
ctcagtattt agaccaggat ctcta                                              25

<210> SEQ ID NO 22
<211> LENGTH: 25
<212> TYPE: DNA
<213> ORGANISM: Artificial Sequence
<220> FEATURE:
<223> OTHER INFORMATION: Synthetic construct

<400> SEQUENCE: 22
cggataaaaa gggcctctcc acgtc                                              25

<210> SEQ ID NO 23
<211> LENGTH: 25
<212> TYPE: DNA
<213> ORGANISM: Artificial Sequence
<220> FEATURE:
<223> OTHER INFORMATION: Synthetic construct

<400> SEQUENCE: 23
gtggtggatt ggccacatcg aagga                                              25

<210> SEQ ID NO 24
<211> LENGTH: 25
<212> TYPE: DNA
<213> ORGANISM: Artificial Sequence
<220> FEATURE:
<223> OTHER INFORMATION: Synthetic construct

<400> SEQUENCE: 24
ctgcaccagc agcacgagtc tctgg                                              25

<210> SEQ ID NO 25
<211> LENGTH: 25
<212> TYPE: DNA
<213> ORGANISM: Artificial Sequence
<220> FEATURE:
<223> OTHER INFORMATION: Synthetic construct
```

```
<400> SEQUENCE: 25
caatctccag agccatcgcc tgtga                                    25

<210> SEQ ID NO 26
<211> LENGTH: 25
<212> TYPE: DNA
<213> ORGANISM: Artificial Sequence
<220> FEATURE:
<223> OTHER INFORMATION: Synthetic construct

<400> SEQUENCE: 26
tggacatatc aggtacatca ggaac                                    25

<210> SEQ ID NO 27
<211> LENGTH: 25
<212> TYPE: DNA
<213> ORGANISM: Artificial Sequence
<220> FEATURE:
<223> OTHER INFORMATION: Synthetic construct

<400> SEQUENCE: 27
tctggcgctc ctgcagcagg ccacc                                    25

<210> SEQ ID NO 28
<211> LENGTH: 25
<212> TYPE: DNA
<213> ORGANISM: Artificial Sequence
<220> FEATURE:
<223> OTHER INFORMATION: Synthetic construct

<400> SEQUENCE: 28
caagataagc aaggagaaga gtttc                                    25

<210> SEQ ID NO 29
<211> LENGTH: 25
<212> TYPE: DNA
<213> ORGANISM: Artificial Sequence
<220> FEATURE:
<223> OTHER INFORMATION: Synthetic construct

<400> SEQUENCE: 29
gcaacaggca agaacggaga tactc                                    25

<210> SEQ ID NO 30
<211> LENGTH: 25
<212> TYPE: DNA
<213> ORGANISM: Artificial Sequence
<220> FEATURE:
<223> OTHER INFORMATION: Synthetic construct

<400> SEQUENCE: 30
cagtatgctg tcttgccgac ggggc                                    25

<210> SEQ ID NO 31
<211> LENGTH: 25
<212> TYPE: DNA
<213> ORGANISM: Artificial Sequence
<220> FEATURE:
<223> OTHER INFORMATION: Synthetic construct

<400> SEQUENCE: 31
gacaaagtct ctgagcttct gggat                                    25

<210> SEQ ID NO 32
<211> LENGTH: 25
```

<210> SEQ ID NO 32
<211> LENGTH: 25
<212> TYPE: DNA
<213> ORGANISM: Artificial Sequence
<220> FEATURE:
<223> OTHER INFORMATION: Synthetic construct

<400> SEQUENCE: 32
acagatttgt tggatggatt tattg                                25

<210> SEQ ID NO 33
<211> LENGTH: 25
<212> TYPE: DNA
<213> ORGANISM: Artificial Sequence
<220> FEATURE:
<223> OTHER INFORMATION: Synthetic construct

<400> SEQUENCE: 33
gctggctgga cagcaccacg gtgtg                                25

<210> SEQ ID NO 34
<211> LENGTH: 25
<212> TYPE: DNA
<213> ORGANISM: Artificial Sequence
<220> FEATURE:
<223> OTHER INFORMATION: Synthetic construct

<400> SEQUENCE: 34
gagttgcgcg ggctgacgcg ccact                                25

<210> SEQ ID NO 35
<211> LENGTH: 25
<212> TYPE: DNA
<213> ORGANISM: Artificial Sequence
<220> FEATURE:
<223> OTHER INFORMATION: Synthetic construct

<400> SEQUENCE: 35
ctggtcaaga cctggaaaac aagat                                25

<210> SEQ ID NO 36
<211> LENGTH: 25
<212> TYPE: DNA
<213> ORGANISM: Artificial Sequence
<220> FEATURE:
<223> OTHER INFORMATION: Synthetic construct

<400> SEQUENCE: 36
agaacacctt tgaggtgttt cccat                                25

<210> SEQ ID NO 37
<211> LENGTH: 25
<212> TYPE: PRT
<213> ORGANISM: Artificial Sequence
<220> FEATURE:
<223> OTHER INFORMATION: Synthetic construct

<400> SEQUENCE: 37

Thr Ala Ala Gly Ala Gly Gly Ala Thr Ala Thr Gly Ala Ala Ala Gly
1               5                   10                  15

Gly Thr Gly Thr Ala Ala Ala Thr Thr
            20                  25

<210> SEQ ID NO 38
<211> LENGTH: 25
<212> TYPE: PRT
<213> ORGANISM: Artificial Sequence
<220> FEATURE:

-continued

```
<223> OTHER INFORMATION: Synthetic construct

<400> SEQUENCE: 38

Thr Gly Gly Thr Ala Cys Cys Cys Cys Ala Gly Gly Cys Gly Cys Ala
1               5                   10                  15

Gly Gly Thr Gly Thr Cys Cys Cys Cys
            20                  25

<210> SEQ ID NO 39
<211> LENGTH: 25
<212> TYPE: PRT
<213> ORGANISM: Artificial Sequence
<220> FEATURE:
<223> OTHER INFORMATION: Synthetic construct

<400> SEQUENCE: 39

Gly Cys Thr Gly Cys Gly Gly Cys Thr Gly Cys Ala Gly Ala Ala Gly
1               5                   10                  15

Gly Cys Cys Ala Gly Gly Cys Cys Cys
            20                  25

<210> SEQ ID NO 40
<211> LENGTH: 25
<212> TYPE: PRT
<213> ORGANISM: Artificial Sequence
<220> FEATURE:
<223> OTHER INFORMATION: Synthetic construct

<400> SEQUENCE: 40

Thr Ala Cys Thr Cys Ala Cys Ala Cys Ala Cys Cys Cys Thr Ala Thr
1               5                   10                  15

Thr Thr Thr Cys Ala Ala Gly Gly Cys
            20                  25

<210> SEQ ID NO 41
<211> LENGTH: 25
<212> TYPE: PRT
<213> ORGANISM: Artificial Sequence
<220> FEATURE:
<223> OTHER INFORMATION: Synthetic construct

<400> SEQUENCE: 41

Cys Gly Thr Ala Thr Cys Thr Thr Gly Ala Ala Gly Gly Thr Gly Cys
1               5                   10                  15

Thr Gly Thr Ala Thr Ala Thr Ala Thr
            20                  25

<210> SEQ ID NO 42
<211> LENGTH: 25
<212> TYPE: PRT
<213> ORGANISM: Artificial Sequence
<220> FEATURE:
<223> OTHER INFORMATION: Synthetic construct

<400> SEQUENCE: 42

Thr Cys Ala Cys Gly Cys Ala Cys Thr Cys Thr Gly Ala Thr Gly Gly
1               5                   10                  15

Thr Gly Cys Thr Gly Gly Ala Ala Ala
            20                  25

<210> SEQ ID NO 43
<211> LENGTH: 25
<212> TYPE: PRT
<213> ORGANISM: Artificial Sequence
```

<220> FEATURE:
<223> OTHER INFORMATION: Synthetic construct

<400> SEQUENCE: 43

```
Cys Gly Cys Thr Gly Cys Cys Ala Ala Gly Gly Cys Thr Gly Thr Gly
1               5                   10                  15

Gly Gly Cys Ala Ala Gly Gly Thr Cys
            20                  25
```

<210> SEQ ID NO 44
<211> LENGTH: 25
<212> TYPE: PRT
<213> ORGANISM: Artificial Sequence
<220> FEATURE:
<223> OTHER INFORMATION: Synthetic construct

<400> SEQUENCE: 44

```
Ala Gly Thr Cys Cys Ala Cys Ala Cys Ala Gly Gly Cys Thr Gly Gly
1               5                   10                  15

Ala Gly Ala Cys Gly Ala Cys Cys Thr
            20                  25
```

<210> SEQ ID NO 45
<211> LENGTH: 25
<212> TYPE: PRT
<213> ORGANISM: Artificial Sequence
<220> FEATURE:
<223> OTHER INFORMATION: Synthetic construct

<400> SEQUENCE: 45

```
Cys Ala Ala Cys Cys Ala Cys Thr Thr Cys Ala Gly Cys Thr Thr Gly
1               5                   10                  15

Ala Cys Cys Cys Thr Cys Ala Ala Cys
            20                  25
```

<210> SEQ ID NO 46
<211> LENGTH: 25
<212> TYPE: PRT
<213> ORGANISM: Artificial Sequence
<220> FEATURE:
<223> OTHER INFORMATION: Synthetic construct

<400> SEQUENCE: 46

```
Ala Gly Thr Ala Ala Gly Ala Ala Gly Thr Thr Cys Cys Ala Ala Gly
1               5                   10                  15

Cys Thr Cys Gly Cys Thr Thr Cys Cys
            20                  25
```

<210> SEQ ID NO 47
<211> LENGTH: 25
<212> TYPE: PRT
<213> ORGANISM: Artificial Sequence
<220> FEATURE:
<223> OTHER INFORMATION: Synthetic construct

<400> SEQUENCE: 47

```
Gly Gly Gly Cys Thr Gly Cys Gly Gly Ala Gly Ala Ala Gly Cys Cys
1               5                   10                  15

Cys Ala Ala Gly Ala Ala Ala Gly Ala
            20                  25
```

<210> SEQ ID NO 48
<211> LENGTH: 25
<212> TYPE: PRT

```
<213> ORGANISM: Artificial Sequence
<220> FEATURE:
<223> OTHER INFORMATION: Synthetic construct

<400> SEQUENCE: 48

Gly Thr Thr Thr Gly Cys Thr Gly Cys Thr Gly Ala Ala Cys Ala Thr
1               5                   10                  15

Ala Cys Ala Ala Thr Cys Thr Thr Thr
                20                  25

<210> SEQ ID NO 49
<211> LENGTH: 25
<212> TYPE: PRT
<213> ORGANISM: Artificial Sequence
<220> FEATURE:
<223> OTHER INFORMATION: Synthetic construct

<400> SEQUENCE: 49

Cys Thr Ala Cys Thr Thr Ala Cys Ala Ala Gly Gly Thr Cys Cys Thr
1               5                   10                  15

Cys Ala Gly Ala Ala Gly Thr Gly Gly
                20                  25

<210> SEQ ID NO 50
<211> LENGTH: 25
<212> TYPE: PRT
<213> ORGANISM: Artificial Sequence
<220> FEATURE:
<223> OTHER INFORMATION: Synthetic construct

<400> SEQUENCE: 50

Ala Cys Cys Thr Thr Cys Ala Ala Gly Gly Gly Ala Gly Ala Cys Thr
1               5                   10                  15

Cys Ala Thr Gly Cys Ala Thr Cys Thr
                20                  25

<210> SEQ ID NO 51
<211> LENGTH: 25
<212> TYPE: PRT
<213> ORGANISM: Artificial Sequence
<220> FEATURE:
<223> OTHER INFORMATION: Synthetic construct

<400> SEQUENCE: 51

Gly Cys Thr Thr Cys Ala Cys Cys Thr Gly Gly Ala Gly Cys Cys Cys
1               5                   10                  15

Cys Cys Ala Ala Ala Gly Ala Cys Ala
                20                  25

<210> SEQ ID NO 52
<211> LENGTH: 25
<212> TYPE: PRT
<213> ORGANISM: Artificial Sequence
<220> FEATURE:
<223> OTHER INFORMATION: Synthetic construct

<400> SEQUENCE: 52

Thr Gly Gly Thr Cys Ala Ala Gly Gly Thr Cys Gly Cys Ala Ala Gly
1               5                   10                  15

Cys Thr Thr Gly Cys Thr Gly Gly Thr
                20                  25

<210> SEQ ID NO 53
<211> LENGTH: 25
```

```
<212> TYPE: PRT
<213> ORGANISM: Artificial Sequence
<220> FEATURE:
<223> OTHER INFORMATION: Synthetic construct

<400> SEQUENCE: 53

Cys Cys Gly Cys Gly Cys Cys Ala Cys Cys Gly Gly Cys Thr Gly
1               5                   10                  15

Ala Gly Thr Cys Ala Gly Cys Cys Cys
            20                  25

<210> SEQ ID NO 54
<211> LENGTH: 25
<212> TYPE: PRT
<213> ORGANISM: Artificial Sequence
<220> FEATURE:
<223> OTHER INFORMATION: Synthetic construct

<400> SEQUENCE: 54

Thr Thr Cys Ala Thr Ala Thr Gly Ala Thr Cys Gly Cys Cys Thr
1               5                   10                  15

Gly Ala Thr Thr Ala Cys Ala Cys Ala
            20                  25

<210> SEQ ID NO 55
<211> LENGTH: 25
<212> TYPE: PRT
<213> ORGANISM: Artificial Sequence
<220> FEATURE:
<223> OTHER INFORMATION: Synthetic construct

<400> SEQUENCE: 55

Ala Ala Cys Ala Ala Cys Cys Cys Ala Thr Gly Ala Cys Gly Ala
1               5                   10                  15

Ala Cys Gly Gly Thr Cys Cys Cys Cys
            20                  25

<210> SEQ ID NO 56
<211> LENGTH: 25
<212> TYPE: PRT
<213> ORGANISM: Artificial Sequence
<220> FEATURE:
<223> OTHER INFORMATION: Synthetic construct

<400> SEQUENCE: 56

Thr Gly Thr Cys Cys Ala Gly Gly Cys Ala Gly Gly Ala Thr Gly
1               5                   10                  15

Cys Cys Cys Ala Ala Gly Ala Cys Ala
            20                  25

<210> SEQ ID NO 57
<211> LENGTH: 25
<212> TYPE: PRT
<213> ORGANISM: Artificial Sequence
<220> FEATURE:
<223> OTHER INFORMATION: Synthetic construct

<400> SEQUENCE: 57

Ala Thr Cys Thr Ala Cys Cys Cys Thr Thr Ala Ala Cys Ala Gly Ala
1               5                   10                  15

Gly Cys Thr Thr Thr Thr Cys Thr Thr
            20                  25

<210> SEQ ID NO 58
```

```
<211> LENGTH: 25
<212> TYPE: PRT
<213> ORGANISM: Artificial Sequence
<220> FEATURE:
<223> OTHER INFORMATION: Synthetic construct

<400> SEQUENCE: 58

Gly Gly Thr Gly Gly Ala Ala Gly Thr Gly Thr Thr Gly Gly Gly Thr
1               5                   10                  15

Gly Gly Thr Gly Ala Ala Thr Thr Cys
            20                  25

<210> SEQ ID NO 59
<211> LENGTH: 25
<212> TYPE: PRT
<213> ORGANISM: Artificial Sequence
<220> FEATURE:
<223> OTHER INFORMATION: Synthetic construct

<400> SEQUENCE: 59

Thr Gly Gly Thr Gly Gly Thr Gly Ala Cys Ala Gly Gly Ala Gly Cys
1               5                   10                  15

Cys Thr Ala Cys Ala Gly Cys Ala Ala
            20                  25

<210> SEQ ID NO 60
<211> LENGTH: 25
<212> TYPE: PRT
<213> ORGANISM: Artificial Sequence
<220> FEATURE:
<223> OTHER INFORMATION: Synthetic construct

<400> SEQUENCE: 60

Thr Gly Cys Thr Gly Gly Cys Thr Ala Cys Ala Ala Cys Ala Gly Ala
1               5                   10                  15

Thr Thr Thr Gly Thr Thr Cys Thr Gly
            20                  25

<210> SEQ ID NO 61
<211> LENGTH: 25
<212> TYPE: PRT
<213> ORGANISM: Artificial Sequence
<220> FEATURE:
<223> OTHER INFORMATION: Synthetic construct

<400> SEQUENCE: 61

Ala Gly Gly Gly Cys Cys Gly Cys Cys Thr Cys Cys Ala Cys Ala Ala
1               5                   10                  15

Cys Cys Thr Gly Gly Thr Cys Thr Gly
            20                  25

<210> SEQ ID NO 62
<211> LENGTH: 25
<212> TYPE: PRT
<213> ORGANISM: Artificial Sequence
<220> FEATURE:
<223> OTHER INFORMATION: Synthetic construct

<400> SEQUENCE: 62

Thr Thr Cys Thr Cys Thr Thr Cys Ala Ala Cys Gly Gly Ala Gly Cys
1               5                   10                  15

Thr Ala Ala Gly Gly Thr Thr Gly Gly
            20                  25
```

-continued

```
<210> SEQ ID NO 63
<211> LENGTH: 25
<212> TYPE: PRT
<213> ORGANISM: Artificial Sequence
<220> FEATURE:
<223> OTHER INFORMATION: Synthetic construct

<400> SEQUENCE: 63

Cys Cys Thr Cys Cys Thr Ala Cys Cys Thr Gly Thr Ala Cys Ala Thr
1               5                   10                  15

Ala Ala Thr Cys Cys Ala Cys Ala Ala
            20                  25

<210> SEQ ID NO 64
<211> LENGTH: 25
<212> TYPE: PRT
<213> ORGANISM: Artificial Sequence
<220> FEATURE:
<223> OTHER INFORMATION: Synthetic construct

<400> SEQUENCE: 64

Gly Gly Ala Gly Ala Ala Gly Ala Ala Cys Cys Gly Gly Gly Thr Cys
1               5                   10                  15

Cys Ala Cys Ala Thr Thr Cys Ala Gly
            20                  25

<210> SEQ ID NO 65
<211> LENGTH: 25
<212> TYPE: PRT
<213> ORGANISM: Artificial Sequence
<220> FEATURE:
<223> OTHER INFORMATION: Synthetic construct

<400> SEQUENCE: 65

Thr Ala Ala Ala Cys Ala Ala Ala Gly Ala Gly Gly Cys Thr Gly Gly
1               5                   10                  15

Gly Ala Thr Gly Gly Gly Thr Thr Thr
            20                  25

<210> SEQ ID NO 66
<211> LENGTH: 25
<212> TYPE: PRT
<213> ORGANISM: Artificial Sequence
<220> FEATURE:
<223> OTHER INFORMATION: Synthetic construct

<400> SEQUENCE: 66

Thr Ala Ala Cys Ala Gly Cys Ala Cys Thr Gly Gly Ala Gly Gly Gly
1               5                   10                  15

Thr Gly Thr Ala Gly Thr Gly Thr Thr
            20                  25

<210> SEQ ID NO 67
<211> LENGTH: 25
<212> TYPE: PRT
<213> ORGANISM: Artificial Sequence
<220> FEATURE:
<223> OTHER INFORMATION: Synthetic construct

<400> SEQUENCE: 67

Thr Thr Thr Cys Cys Cys Ala Cys Gly Cys Gly Thr Gly Thr Thr Gly
1               5                   10                  15

Gly Ala Gly Thr Thr Cys Cys Cys Thr
            20                  25
```

<210> SEQ ID NO 68
<211> LENGTH: 25
<212> TYPE: PRT
<213> ORGANISM: Artificial Sequence
<220> FEATURE:
<223> OTHER INFORMATION: Synthetic construct

<400> SEQUENCE: 68

Ala Ala Cys Cys Ala Ala Gly Cys Thr Thr Thr Thr Gly Gly Thr Gly
1               5                   10                  15

Cys Ala Thr Ala Gly Cys Ala Gly Cys
            20                  25

<210> SEQ ID NO 69
<211> LENGTH: 25
<212> TYPE: PRT
<213> ORGANISM: Artificial Sequence
<220> FEATURE:
<223> OTHER INFORMATION: Synthetic construct

<400> SEQUENCE: 69

Gly Ala Gly Gly Ala Gly Ala Gly Cys Ala Ala Cys Thr Thr Cys Cys
1               5                   10                  15

Cys Cys Cys Ala Cys Gly Cys Cys Ala
            20                  25

<210> SEQ ID NO 70
<211> LENGTH: 25
<212> TYPE: PRT
<213> ORGANISM: Artificial Sequence
<220> FEATURE:
<223> OTHER INFORMATION: Synthetic construct

<400> SEQUENCE: 70

Gly Ala Ala Cys Ala Thr Cys Ala Thr Cys Ala Gly Cys Thr Gly Ala
1               5                   10                  15

Gly Cys Cys Ala Gly Thr Thr Cys Cys
            20                  25

<210> SEQ ID NO 71
<211> LENGTH: 25
<212> TYPE: PRT
<213> ORGANISM: Artificial Sequence
<220> FEATURE:
<223> OTHER INFORMATION: Synthetic construct

<400> SEQUENCE: 71

Thr Gly Thr Cys Ala Ala Thr Gly Cys Thr Cys Ala Gly Gly Ala Gly
1               5                   10                  15

Cys Cys Cys Thr Gly Thr Ala Ala Thr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Synthetic construct

<400> SEQUENCE: 72

Gly Gly Cys Thr Thr Cys Thr Cys Ala Gly Gly Ala Ala Ala Ala Gly
1               5                   10                  15

Gly Thr Thr Cys Ala Gly Ala Ala Thr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Synthetic construct

<400> SEQUENCE: 73

Thr Thr Thr Cys Cys Gly Gly Ala Cys Ala Cys Thr Cys Gly Ala Gly
1               5                   10                  15

Ala Ala Thr Gly Ala Thr Gly Ala Gly
            20                  25

<210> SEQ ID NO 74
<211> LENGTH: 25
<212> TYPE: PRT
<213> ORGANISM: Artificial Sequence
<220> FEATURE:
<223> OTHER INFORMATION: Synthetic construct

<400> SEQUENCE: 74

Cys Thr Ala Cys Ala Ala Cys Gly Thr Gly Gly Ala Thr Cys Ala Gly
1               5                   10                  15

Cys Ala Cys Cys Gly Gly Ala Ala Gly
            20                  25

<210> SEQ ID NO 75
<211> LENGTH: 25
<212> TYPE: PRT
<213> ORGANISM: Artificial Sequence
<220> FEATURE:
<223> OTHER INFORMATION: Synthetic construct

<400> SEQUENCE: 75

Thr Thr Gly Gly Ala Gly Ala Thr Ala Thr Ala Thr Ala Ala Gly Gly
1               5                   10                  15

Cys Thr Thr Thr Cys Ala Gly Thr Thr
            20                  25

<210> SEQ ID NO 76
<211> LENGTH: 25
<212> TYPE: PRT
<213> ORGANISM: Artificial Sequence
<220> FEATURE:
<223> OTHER INFORMATION: Synthetic construct

<400> SEQUENCE: 76

Cys Cys Ala Gly Gly Cys Thr Cys Ala Gly Ala Thr Cys Cys Gly Gly
1               5                   10                  15

Thr Gly Thr Thr Thr Ala Ala Ala Gly
            20                  25

<210> SEQ ID NO 77
<211> LENGTH: 25
<212> TYPE: PRT
<213> ORGANISM: Artificial Sequence
<220> FEATURE:
<223> OTHER INFORMATION: Synthetic construct

<400> SEQUENCE: 77

Gly Ala Gly Gly Ala Ala Ala Ala Ala Thr Gly Gly Thr Gly Gly Ala
1               5                   10                  15

Ala Ala Thr Thr Gly Ala Ala Ala Cys
            20                  25

<210> SEQ ID NO 78
<211> LENGTH: 25
<212> TYPE: PRT
<213> ORGANISM: Artificial Sequence
<220> FEATURE:
<223> OTHER INFORMATION: Synthetic construct

<400> SEQUENCE: 78

Gly Gly Gly Gly Gly Ala Cys Ala Thr Gly Thr Gly Gly Cys Gly Gly
1               5                   10                  15

Thr Thr Thr Thr Thr Gly Ala Thr Gly
            20                  25

<210> SEQ ID NO 79
<211> LENGTH: 25
<212> TYPE: PRT
<213> ORGANISM: Artificial Sequence
<220> FEATURE:
<223> OTHER INFORMATION: Synthetic construct

<400> SEQUENCE: 79

Ala Gly Cys Cys Cys Ala Cys Ala Gly Cys Thr Cys Cys Ala Thr Gly
1               5                   10                  15

Gly Thr Ala Gly Gly Ala Gly Thr Cys
            20                  25

<210> SEQ ID NO 80
<211> LENGTH: 25
<212> TYPE: PRT
<213> ORGANISM: Artificial Sequence
<220> FEATURE:
<223> OTHER INFORMATION: Synthetic construct

<400> SEQUENCE: 80

Thr Thr Cys Ala Ala Cys Gly Cys Thr Thr Cys Gly Gly Ala Ala
1               5                   10                  15

Thr Gly Ala Gly Thr Thr Thr Gly Ala
            20                  25

<210> SEQ ID NO 81
<211> LENGTH: 25
<212> TYPE: PRT
<213> ORGANISM: Artificial Sequence
<220> FEATURE:
<223> OTHER INFORMATION: Synthetic construct

<400> SEQUENCE: 81

Gly Ala Gly Gly Ala Ala Gly Ala Ala Gly Ala Cys Cys Ala Thr Cys
1               5                   10                  15

Thr Gly Thr Gly Gly Cys Ala Cys Cys
            20                  25

<210> SEQ ID NO 82
<211> LENGTH: 25
<212> TYPE: PRT
<213> ORGANISM: Artificial Sequence
<220> FEATURE:
<223> OTHER INFORMATION: Synthetic construct

<400> SEQUENCE: 82

Thr Thr Cys Cys Thr Cys Ala Thr Cys Ala Cys Cys Ala Gly Ala
1               5                   10                  15

Thr Cys Cys Thr Gly Gly Thr Gly Gly
            20                  25

<210> SEQ ID NO 83
<211> LENGTH: 25
<212> TYPE: PRT
<213> ORGANISM: Artificial Sequence
<220> FEATURE:
<223> OTHER INFORMATION: Synthetic construct

<400> SEQUENCE: 83

Gly Gly Cys Gly Gly Cys Cys Gly Cys Gly Gly Gly Ala Thr Cys Thr
1               5                   10                  15

Cys Cys Cys Ala Gly Cys Cys Ala Thr
            20                  25

<210> SEQ ID NO 84
<211> LENGTH: 25
<212> TYPE: PRT
<213> ORGANISM: Artificial Sequence
<220> FEATURE:
<223> OTHER INFORMATION: Synthetic construct

<400> SEQUENCE: 84

Gly Ala Ala Thr Cys Ala Gly Cys Gly Cys Cys Ala Gly Ala Thr
1               5                   10                  15

Cys Cys Cys Ala Cys Cys Cys Thr Thr
            20                  25

<210> SEQ ID NO 85
<211> LENGTH: 25
<212> TYPE: PRT
<213> ORGANISM: Artificial Sequence
<220> FEATURE:
<223> OTHER INFORMATION: Synthetic construct

<400> SEQUENCE: 85

Gly Ala Gly Ala Thr Cys Gly Ala Thr Gly Ala Gly Cys Ala Thr Gly
1               5                   10                  15

Cys Cys Cys Cys Cys Gly Gly Ala Gly
            20                  25

<210> SEQ ID NO 86
<211> LENGTH: 25
<212> TYPE: PRT
<213> ORGANISM: Artificial Sequence
<220> FEATURE:
<223> OTHER INFORMATION: Synthetic construct

<400> SEQUENCE: 86

Gly Cys Ala Cys Thr Cys Cys Cys Ala Ala Gly Ala Thr Thr Gly Ala
1               5                   10                  15

Thr Ala Ala Thr Thr Ala Gly Gly Ala
            20                  25

<210> SEQ ID NO 87
<211> LENGTH: 25
<212> TYPE: PRT
<213> ORGANISM: Artificial Sequence
<220> FEATURE:

<223> OTHER INFORMATION: Synthetic construct

<400> SEQUENCE: 87

Gly Gly Cys Thr Gly Cys Thr Thr Cys Thr Cys Ala Thr Ala Gly Gly
1               5                   10                  15

Gly Cys Ala Cys Thr Thr Gly Ala Thr
            20                  25

<210> SEQ ID NO 88
<211> LENGTH: 25
<212> TYPE: PRT
<213> ORGANISM: Artificial Sequence
<220> FEATURE:
<223> OTHER INFORMATION: Synthetic construct

<400> SEQUENCE: 88

Ala Gly Cys Cys Gly Cys Thr Thr Cys Thr Gly Gly Ala Ala Gly Cys
1               5                   10                  15

Ala Thr Gly Ala Gly Thr Gly Gly Gly
            20                  25

<210> SEQ ID NO 89
<211> LENGTH: 25
<212> TYPE: PRT
<213> ORGANISM: Artificial Sequence
<220> FEATURE:
<223> OTHER INFORMATION: Synthetic construct

<400> SEQUENCE: 89

Ala Thr Ala Cys Cys Thr Cys Ala Gly Ala Gly Cys Thr Gly Gly Cys
1               5                   10                  15

Gly Gly Cys Thr Gly Thr Ala Cys Cys
            20                  25

<210> SEQ ID NO 90
<211> LENGTH: 25
<212> TYPE: PRT
<213> ORGANISM: Artificial Sequence
<220> FEATURE:
<223> OTHER INFORMATION: Synthetic construct

<400> SEQUENCE: 90

Gly Cys Cys Cys Thr Gly Ala Ala Thr Gly Ala Thr Thr Thr Thr Thr
1               5                   10                  15

Gly Cys Thr Gly Cys Ala Ala Thr Thr
            20                  25

<210> SEQ ID NO 91
<211> LENGTH: 25
<212> TYPE: PRT
<213> ORGANISM: Artificial Sequence
<220> FEATURE:
<223> OTHER INFORMATION: Synthetic construct

<400> SEQUENCE: 91

Gly Ala Gly Cys Ala Thr Ala Gly Thr Cys Thr Ala Gly Gly Gly Gly
1               5                   10                  15

Thr Gly Gly Gly Gly Thr Ala Thr Cys
            20                  25

<210> SEQ ID NO 92
<211> LENGTH: 25
<212> TYPE: PRT
<213> ORGANISM: Artificial Sequence

```
<220> FEATURE:
<223> OTHER INFORMATION: Synthetic construct

<400> SEQUENCE: 92

Gly Cys Thr Cys Gly Gly Gly Cys Thr Ala Cys Thr Thr Cys Gly Ala
1               5                   10                  15
Gly Cys Ala Gly Gly Ala Gly Thr Cys
            20                  25

<210> SEQ ID NO 93
<211> LENGTH: 25
<212> TYPE: PRT
<213> ORGANISM: Artificial Sequence
<220> FEATURE:
<223> OTHER INFORMATION: Synthetic construct

<400> SEQUENCE: 93

Thr Cys Thr Thr Cys Thr Thr Thr Ala Ala Ala Gly Gly Cys Ala Ala
1               5                   10                  15
Ala Thr Gly Gly Gly Ala Gly Ala Gly
            20                  25

<210> SEQ ID NO 94
<211> LENGTH: 25
<212> TYPE: PRT
<213> ORGANISM: Artificial Sequence
<220> FEATURE:
<223> OTHER INFORMATION: Synthetic construct

<400> SEQUENCE: 94

Ala Gly Cys Cys Thr Gly Ala Ala Ala Gly Thr Gly Ala Ala Ala Gly
1               5                   10                  15
Cys Ala Ala Ala Ala Thr Cys Thr Ala
            20                  25

<210> SEQ ID NO 95
<211> LENGTH: 25
<212> TYPE: PRT
<213> ORGANISM: Artificial Sequence
<220> FEATURE:
<223> OTHER INFORMATION: Synthetic construct

<400> SEQUENCE: 95

Gly Gly Ala Ala Cys Ala Ala Cys Ala Gly Gly Cys Cys Thr Thr Ala
1               5                   10                  15
Thr Thr Cys Cys Ala Cys Thr Gly Cys
            20                  25

<210> SEQ ID NO 96
<211> LENGTH: 25
<212> TYPE: PRT
<213> ORGANISM: Artificial Sequence
<220> FEATURE:
<223> OTHER INFORMATION: Synthetic construct

<400> SEQUENCE: 96

Ala Thr Gly Ala Ala Gly Ala Ala Ala Gly Cys Cys Cys Ala Gly Ala
1               5                   10                  15
Gly Gly Cys Ala Gly Ala Gly Cys Thr
            20                  25

<210> SEQ ID NO 97
<211> LENGTH: 25
<212> TYPE: PRT
```

```
<213> ORGANISM: Artificial Sequence
<220> FEATURE:
<223> OTHER INFORMATION: Synthetic construct

<400> SEQUENCE: 97

Thr Ala Thr Thr Cys Ala Cys Cys Gly Ala Ala Gly Ala Gly Ala
1               5                   10                  15

Ala Ala Ala Cys Cys Cys Ala Ala Ala
            20                  25

<210> SEQ ID NO 98
<211> LENGTH: 25
<212> TYPE: PRT
<213> ORGANISM: Artificial Sequence
<220> FEATURE:
<223> OTHER INFORMATION: Synthetic construct

<400> SEQUENCE: 98

Ala Gly Gly Ala Cys Ala Ala Gly Gly Ala Gly Ala Thr Gly Gly
1               5                   10                  15

Ala Ala Thr Gly Gly Ala Ala Ala Thr
            20                  25

<210> SEQ ID NO 99
<211> LENGTH: 25
<212> TYPE: PRT
<213> ORGANISM: Artificial Sequence
<220> FEATURE:
<223> OTHER INFORMATION: Synthetic construct

<400> SEQUENCE: 99

Ala Ala Cys Cys Cys Thr Gly Gly Ala Gly Ala Ala Ala Gly Thr
1               5                   10                  15

Cys Ala Gly Cys Gly Gly Ala Cys Ala
            20                  25

<210> SEQ ID NO 100
<211> LENGTH: 25
<212> TYPE: PRT
<213> ORGANISM: Artificial Sequence
<220> FEATURE:
<223> OTHER INFORMATION: Synthetic construct

<400> SEQUENCE: 100

Cys Thr Cys Ala Gly Cys Thr Cys Thr Gly Cys Ala Gly Cys Ala
1               5                   10                  15

Cys Cys Cys Ala Thr Thr Thr Gly Thr
            20                  25

<210> SEQ ID NO 101
<211> LENGTH: 25
<212> TYPE: PRT
<213> ORGANISM: Artificial Sequence
<220> FEATURE:
<223> OTHER INFORMATION: Synthetic construct

<400> SEQUENCE: 101

Thr Ala Thr Ala Ala Ala Ala Gly Ala Cys Cys Thr Ala Thr Cys Cys
1               5                   10                  15

Cys Thr Cys Thr Thr Thr Gly Thr Thr
            20                  25

<210> SEQ ID NO 102
<211> LENGTH: 25
```

```
<212> TYPE: PRT
<213> ORGANISM: Artificial Sequence
<220> FEATURE:
<223> OTHER INFORMATION: Synthetic construct

<400> SEQUENCE: 102

Thr Cys Thr Cys Ala Thr Thr Gly Cys Ala Gly Gly Ala Ala Ala Gly
1               5                   10                  15

Gly Cys Cys Gly Ala Gly Gly Gly
            20                  25

<210> SEQ ID NO 103
<211> LENGTH: 25
<212> TYPE: PRT
<213> ORGANISM: Artificial Sequence
<220> FEATURE:
<223> OTHER INFORMATION: Synthetic construct

<400> SEQUENCE: 103

Ala Ala Cys Gly Thr Thr Thr Gly Gly Gly Thr Thr Thr Thr Cys Cys
1               5                   10                  15

Thr Ala Gly Cys Thr Ala Cys Ala Thr
            20                  25

<210> SEQ ID NO 104
<211> LENGTH: 25
<212> TYPE: PRT
<213> ORGANISM: Artificial Sequence
<220> FEATURE:
<223> OTHER INFORMATION: Synthetic construct

<400> SEQUENCE: 104

Cys Thr Cys Cys Thr Gly Thr Ala Gly Thr Ala Ala Cys Thr Gly Thr
1               5                   10                  15

Ala Ala Gly Ala Ala Ala Ala Gly Cys
            20                  25

<210> SEQ ID NO 105
<211> LENGTH: 25
<212> TYPE: PRT
<213> ORGANISM: Artificial Sequence
<220> FEATURE:
<223> OTHER INFORMATION: Synthetic construct

<400> SEQUENCE: 105

Thr Thr Thr Cys Cys Cys Ala Thr Gly Ala Thr Thr Cys Cys Thr
1               5                   10                  15

Thr Gly Gly Cys Ala Gly Cys Ala Gly
            20                  25

<210> SEQ ID NO 106
<211> LENGTH: 25
<212> TYPE: PRT
<213> ORGANISM: Artificial Sequence
<220> FEATURE:
<223> OTHER INFORMATION: Synthetic construct

<400> SEQUENCE: 106

Cys Ala Gly Gly Thr Cys Cys Ala Cys Thr Cys Ala Gly Gly Ala
1               5                   10                  15

Ala Thr Cys Cys Thr Cys Ala Ala Thr
            20                  25

<210> SEQ ID NO 107
```

```
<211> LENGTH: 25
<212> TYPE: PRT
<213> ORGANISM: Artificial Sequence
<220> FEATURE:
<223> OTHER INFORMATION: Synthetic construct

<400> SEQUENCE: 107

Gly Ala Gly Gly Thr Gly Gly Thr Cys Cys Ala Ala Gly Cys Cys Cys
1               5                   10                  15

Ala Gly Gly Ala Ala Gly Cys Gly Cys
            20                  25

<210> SEQ ID NO 108
<211> LENGTH: 25
<212> TYPE: PRT
<213> ORGANISM: Artificial Sequence
<220> FEATURE:
<223> OTHER INFORMATION: Synthetic construct

<400> SEQUENCE: 108

Ala Cys Thr Gly Thr Gly Gly Cys Thr Gly Ala Gly Cys Ala Thr Cys
1               5                   10                  15

Thr Cys Thr Gly Gly Ala Ala Gly Thr
            20                  25

<210> SEQ ID NO 109
<211> LENGTH: 25
<212> TYPE: PRT
<213> ORGANISM: Artificial Sequence
<220> FEATURE:
<223> OTHER INFORMATION: Synthetic construct

<400> SEQUENCE: 109

Cys Gly Gly Cys Cys Thr Cys Cys Ala Ala Gly Cys Gly Gly Cys Cys
1               5                   10                  15

Gly Thr Gly Gly Thr Gly Thr Gly Thr
            20                  25

<210> SEQ ID NO 110
<211> LENGTH: 25
<212> TYPE: PRT
<213> ORGANISM: Artificial Sequence
<220> FEATURE:
<223> OTHER INFORMATION: Synthetic construct

<400> SEQUENCE: 110

Ala Cys Gly Cys Gly Gly Gly Gly Cys Gly Cys Ala Gly Thr Gly Gly
1               5                   10                  15

Thr Ala Thr Cys Thr Thr Ala Thr Thr
            20                  25

<210> SEQ ID NO 111
<211> LENGTH: 25
<212> TYPE: PRT
<213> ORGANISM: Artificial Sequence
<220> FEATURE:
<223> OTHER INFORMATION: Synthetic construct

<400> SEQUENCE: 111

Cys Cys Thr Ala Cys Cys Thr Cys Cys Ala Gly Cys Cys Thr Ala
1               5                   10                  15

Ala Thr Thr Gly Ala Cys Cys Gly Gly
            20                  25
```

```
<210> SEQ ID NO 112
<211> LENGTH: 25
<212> TYPE: PRT
<213> ORGANISM: Artificial Sequence
<220> FEATURE:
<223> OTHER INFORMATION: Synthetic construct

<400> SEQUENCE: 112

Gly Thr Thr Ala Cys Ala Ala Gly Thr Gly Thr Gly Ala Gly Gly Ala
1               5                   10                  15

Cys Thr Gly Cys Gly Gly Gly Ala Ala
            20                  25
```